(12) United States Patent
Akama et al.

(10) Patent No.: US 10,669,291 B2
(45) Date of Patent: *Jun. 2, 2020

(54) BORON-CONTAINING SMALL MOLECULES AS ANTIPROTOZOAL AGENTS

(71) Applicant: Anacor Pharmaceuticals, Inc., New York, NY (US)

(72) Inventors: Tsutomu Akama, Sunnyvale, CA (US); Eric Easom, Menlo Park, CA (US); Yvonne Freund, Los Altos, CA (US); Jacob J. Plattner, Berkeley, CA (US); Jessica Sligar, Cary, NC (US); Daitao Chen, Raleigh, NC (US); Jennifer Freeman, Durham, NC (US); Joe Perales, Durham, NC (US)

(73) Assignee: Anacor Pharmaceuticals, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/241,841

(22) Filed: Jan. 7, 2019

(65) Prior Publication Data
US 2019/0135837 A1   May 9, 2019

Related U.S. Application Data

(60) Continuation of application No. 15/801,127, filed on Nov. 1, 2017, now Pat. No. 10,214,548, which is a division of application No. 15/439,634, filed on Feb. 22, 2017, now Pat. No. 9,815,857, which is a continuation of application No. 14/765,152, filed as application No. PCT/US2014/014266 on Jan. 31, 2014, now Pat. No. 9,598,443.

(60) Provisional application No. 61/759,981, filed on Feb. 1, 2013.

(51) Int. Cl.
*A61K 31/69* (2006.01)
*C07F 5/02* (2006.01)

(52) U.S. Cl.
CPC .............. *C07F 5/025* (2013.01); *A61K 31/69* (2013.01)

(58) Field of Classification Search
CPC .................................. A61K 31/69; C07F 5/02
See application file for complete search history.

(56) References Cited

U.S. PATENT DOCUMENTS

| | | | |
|---|---|---|---|
| 815,857 A | 3/1906 | North | |
| 9,598,443 B2 * | 3/2017 | Akama | ............. A61K 31/69 |
| 9,815,857 B2 * | 11/2017 | Akama | ............. A61K 31/69 |
| 10,214,548 B2 * | 2/2019 | Akama | ............. A61K 31/69 |
| 2011/0190235 A1 | 8/2011 | Chen | |

FOREIGN PATENT DOCUMENTS

| | | |
|---|---|---|
| WO | WO 2010/045503 A1 | 4/2010 |
| WO | WO 2011/019618 A1 | 2/2011 |
| WO | WO 2011/116348 A1 | 9/2011 |

OTHER PUBLICATIONS

U.S. Appl. No. 13/861,846, filed Apr. 12, 2013, now abandoned.
U.S. Appl. No. 13/673,860, filed Nov. 9, 2012, now abandoned.
U.S. Appl. No. 13/607,321, filed Sep. 7, 2012, now abandoned.
U.S. Appl. No. 13/607,405, filed Sep. 7, 2012, now abandoned.
U.S. Appl. No. 13/607,250, filed Sep. 7, 2012, now abandoned.
U.S. Appl. No. 15/718,422, filed Sep. 28, 2017.
U.S. Appl. No. 15/562,099, filed Sep. 27, 2017.
U.S. Appl. No. 15/685,846, filed Aug. 24, 2017.
U.S. Appl. No. 15/599,203, filed May 18, 2017.
U.S. Appl. No. 15/439,634, filed Feb. 22, 2017, now allowed.
U.S. Appl. No. 15/309,408, filed Nov. 7, 2016.
U.S. Appl. No. 15/355,393, filed Nov. 18, 2016.
U.S. Appl. No. 15/355,813, filed Nov. 18, 2016.
U.S. Appl. No. 15/134,286, filed Apr. 20, 2016; now U.S. Pat. No. 9,566,290.
U.S. Appl. No. 15/091,394, filed Apr. 5, 2016; now U.S. Pat. No. 9,572,823.
U.S. Appl. No. 15/068,352, filed Mar. 11, 2016; now U.S. Pat. No. 9,549,938.
U.S. Appl. No. 15/046,322, filed Feb. 17, 2016; now U.S. Pat. No. 9,566,289.
U.S. Appl. No. 14/977,052, filed Dec. 21, 2015; now abandoned.
U.S. Appl. No. 14/910,996, filed Feb. 8, 2016.
U.S. Appl. No. 14/537,771, filed Nov. 10, 2014; now abandoned.
U.S. Appl. No. 14/537,694, filed Nov. 10, 2014, now abandoned.
U.S. Appl. No. 14/201,459, filed Mar. 7, 2014, now U.S. Pat. No. 9,353,133.
U.S. Appl. No. 14/165,428, filed Mar. 7, 2014, now abandoned.
U.S. Appl. No. 13/874,329, filed Apr. 30, 2013, now U.S. Pat. No. 8,889,656.
U.S. Appl. No. 13/224,252, filed Sep. 1, 2011, now U.S. Pat. No. 8,440,642.
U.S. Appl. No. 13/356,488, filed Jan. 23, 2012, now U.S. Pat. No. 8,722,917.
U.S. Appl. No. 12/629,753, filed Dec. 2, 2009, now U.S. Pat. No. 8,115,026.
U.S. Appl. No. 11/357,687, filed Feb. 16, 2006, now U.S. Pat. No. 7,582,621.
U.S. Appl. No. 11/505,591, filed Aug. 16, 2006, now U.S. Pat. No. 7,767,657.
U.S. Appl. No. 12/507,010, filed Jul. 21, 2009, now U.S. Pat. No. 8,039,451.
U.S. Appl. No. 11/676,120, filed Feb. 16, 2007, now U.S. Pat. No. 8,168,614.
U.S. Appl. No. 13/453,682, filed Apr. 23, 2012, now U.S. Pat. No. 8,501,712.
U.S. Appl. No. 13/954,770, filed Jul. 30, 2013, now U.S. Pat. No. 9,029,353.
U.S. Appl. No. 14/688,581, filed Apr. 16, 2015; now U.S. Pat. No. 9,682,092.

(Continued)

*Primary Examiner* — D Margaret M Seaman
(74) *Attorney, Agent, or Firm* — Morgan, Lewis & Bockius LLP

(57) ABSTRACT

This invention provides, among other things, novel compounds useful for treating protozoal infections, pharmaceutical compositions containing such compounds, as well as combinations of these compounds with at least one additional therapeutically effective agent.

3 Claims, 3 Drawing Sheets

(56) References Cited

OTHER PUBLICATIONS

U.S. Appl. No. 11/762,038, filed Jun. 12, 2007, now abandoned.
U.S. Appl. No. 11/865,725, filed Oct. 1, 2007, now abandoned.
U.S. Appl. No. 12/142,692, filed Jun. 19, 2008, now U.S. Pat. No. 7,816,344.
U.S. Appl. No. 12/752,789, filed Apr. 1, 2010, now abandoned.
U.S. Appl. No. 12/848,051, filed Jul. 30, 2010, now U.S. Pat. No. 8,895,534.
U.S. Appl. No. 12/399,015, filed Mar. 5, 2009, now U.S. Pat. No. 8,039,450.
U.S. Appl. No. 13/236,543, filed Sep. 19, 2011, now U.S. Pat. No. 8,461,135.
U.S. Appl. No. 14/536,483, filed Nov. 7, 2014, now allowed.
U.S. Appl. No. 13/915,494, filed Jun. 11, 2013, now U.S. Pat. No. 9,012,431.
U.S. Appl. No. 14/666,075, filed Mar. 23, 2015, now U.S. Pat. No. 9,416,146.
U.S. Appl. No. 13/062,450, filed Mar. 4, 2011; now U.S. Pat. No. 9,493,489.
U.S. Appl. No. 12/464,829, filed May 12, 2009, now abandoned.
U.S. Appl. No. 13/062,466, filed Mar. 4, 2011, now U.S. Pat. No. 8,470,803.
U.S. Appl. No. 12/641,318, filed Dec. 17, 2009, now U.S. Pat. No. 8,461,364.
U.S. Appl. No. 12/873,036, filed Aug. 31, 2010, now abandoned.
U.S. Appl. No. 12/844,748, filed Jul. 27, 2010, now U.S. Pat. No. 8,343,944.
U.S. Appl. No. 13/062,491, filed Mar. 4, 2011, now U.S. Pat. No. 8,461,336.
U.S. Appl. No. 13/503,016, filed Jun. 25, 2012, now allowed.
U.S. Appl. No. 12/857,305, filed Aug. 16, 2010, now abandoned.
U.S. Appl. No. 12/852,351, filed Aug. 6, 2010; now U.S. Pat. No. 9,440,994.
U.S. Appl. No. 12/944,690, filed Nov. 11, 2010, now U.S. Pat. No. 8,461,134.
U.S. Appl. No. 13/015,487, filed Jan. 27, 2011, now U.S. Pat. No. 8,716,478.
U.S. Appl. No. 14/133,537, filed Dec. 18, 2013, now U.S. Pat. No. 9,145,429.
U.S. Appl. No. 14/852,122, filed Sep. 11, 2015; now U.S. Pat. No. 9,499,570.
U.S. Appl. No. 12/944,699, filed Nov. 11, 2010, now abandoned.
U.S. Appl. No. 13/639,594, filed Sep. 7, 2012, now U.S. Pat. No. 9,243,003.
U.S. Appl. No. 14/969,467, filed Dec. 15, 2015.
U.S. Appl. No. 13/227,444, filed Sep. 7, 2011, now U.S. Pat. No. 8,703,742.
U.S. Appl. No. 14/221,637, filed Mar. 21, 2014, now U.S. Pat. No. 9,751,898.
U.S. Appl. No. 13/678,576, filed Nov. 16, 2012, now U.S. Pat. No. 8,853,186.
U.S. Appl. No. 14/507,453, filed Oct. 14, 2014, now U.S. Pat. No. 9,156,860.
U.S. Appl. No. 14/852,220, filed Sep. 11, 2015; now abandoned.
U.S. Appl. No. 13/678,578, filed Nov. 16, 2012, now U.S. Pat. No. 8,546,357.
U.S. Appl. No. 14/760,208, filed Jul. 10, 2015; now U.S. Pat. No. 9,617,285.
U.S. Appl. No. 14/394,427, filed Oct. 14, 2014; now abandoned.
U.S. Appl. No. 14/765,152, filed Jul. 31, 2015; now U.S. Pat. No. 9,598,443.
U.S. Appl. No. 14/906,849, filed Jan. 21, 2016; now U.S. Pat. No. 9,493,490.

\* cited by examiner

FIG. 1A

| Compound # | T.brucei IC50 (mg/mL) | T.cruzi IC50 (mg/mL) | T.congo IC50 (mg/mL) | L. donovani axenic IC50 (ug/mL) | L. donovani macrophage IC50 (ug/mL) | L929 IC50 (ug/mL) |
|---|---|---|---|---|---|---|
| 1 | 0.037 | 0.214 | 0.04 | | | |
| 2 | 0.01 | 0.012 | | | | |
| 3 | 0.035 | 0.047 | 0.0952 | | | |
| 4 | 0.045 | 0.07 | 0.116 | | | |
| 5 | 0.019 | 0.108 | 0.045 | | | |
| 6 | 0.023 | 0.052 | | | | |
| 7 | 0.04 | 0.013 | 0.0724 | | | |
| 8 | 0.118 | | 0.118 | | | |
| 9 | 0.136 | | 0.136 | | | |
| 10 | 0.085 | | | | | |
| 11 | 0.142 | | | | | |
| 12 | 0.097 | 1.28 | 0.199 | | | |
| 13 | 0.29 | 0.947 | 0.671 | | | |
| 14 | 0.126 | 0.263 | 0.303 | | | |
| 15 | 0.276 | 0.86 | 0.276 | | | |
| 16 | 0.086 | 0.313 | 0.317 | | | |
| 17 | 0.077 | 0.216 | 0.185 | | | |
| 18 | 0.175 | 0.283 | 0.459 | | | |
| 19 | 0.401 | 2.55 | 0.401 | | | |
| 20 | 0.875 | | | | | |
| 21 | | | | | | |

FIG. 1B

| Compound # | T.brucei IC50 (mg/mL) | T.cruzi IC50 (mg/mL) | T.congo IC50 (mg/mL) | L.donovani axenic IC50 (ug/mL) | L.donovani macrophage IC50 (ug/mL) | L929 IC50 (ug/mL) |
|---|---|---|---|---|---|---|
| 22 | 0.168 | | | | | |
| 23 | 0.169 | 0.39 | 0.454 | | | |
| 24 | 0.075 | 0.13 | 0.188 | | | |
| 25 | 0.578 | 0.148 | 1.35 | | | |
| 26 | 0.177 | 1.77 | 0.393 | | | |
| 27 | 0.073 | 0.38 | 0.058 | | | |
| 28 | 0.159 | 0.068 | 0.366 | | | |
| 29 | 0.214 | 0.719 | 0.214 | | | |
| 30 | 0.133 | 0.301 | 0.133 | | | |
| 31 | 0.171 | 1.19 | 0.386 | | | |
| 32 | 0.0369 | 0.0818 | 0.0537 | 0.14 | | 8.03 |
| 33 | 0.011 | 0.129 | 0.019 | 0.1 | | 1.27 |
| 34 | 0.0275 | 0.07 | 0.0655 | 0.27 | 2.39 | 5.17 |
| 35 | 0.03 | 0.123 | 0.0746 | 0.2 | | 4 |
| 36 | 0.0101 | 0.112 | 0.226 | 0.72 | | 10 |
| 37 | 0.038 | 0.341 | 0.091 | | | |
| 38 | 0.0296 | 0.0879 | 0.014 | 0.05 | 0.33 | 10 |
| 39 | 0.0639 | 0.432 | 0.0878 | 0.23 | | 9.05 |

FIG. 2

| Compound # | Dose (mg/kg, IP) | Days | Survived/infected at Day 60 |
|---|---|---|---|
| 1 | 10 | 4 | 5/5 |
| 1 | 10 | 1 | 5/5 |
| 1 | 3 | 4 | 5/5 |
| 1 | 1 | 4 | 0/5 |
| 28 | 10 | 4 | 4/5 |
| 28 | 3 | 4 | 0/5 |
| 34 | 10 | 4 | 5/5 |
| 34 | 3 | 4 | 3/5 |
| 39 | 10 | 4 | 5/5 |
| 39 | 3 | 4 | 0/5 |

BORON-CONTAINING SMALL MOLECULES AS ANTIPROTOZOAL AGENTS

CROSS-REFERENCE TO RELATED APPLICATIONS

This application is a continuation of U.S. patent application Ser. No. 15/801,127, filed Nov. 1, 2017, now U.S. Pat. No. 10,214,548, which is a divisional of U.S. patent application Ser. No. 15/439,634, filed Feb. 22, 2017, now U.S. Pat. No. 9,815,857, which is a continuation of U.S. patent application Ser. No. 14/765,152, filed Jul. 31, 2015, now U.S. Pat. No. 9,598,443, which is National Stage of International Patent Application No. PCT/US2014/014266, filed Jan. 31, 2014 and published as WO 2014/121124 A1, which claims priority under 35 U.S.C. § 119(e) to U.S. Provisional Patent Application No. 61/759,981, filed Feb. 1, 2013, the entire content of which applications is incorporated herein in its entirety for all purposes.

BACKGROUND OF THE INVENTION

The global rise of protozoa resistant to antimicrobials in general, poses a major threat. Deployment of massive quantities of antimicrobial agents into the ecosphere during the past 60 years has introduced a powerful selective pressure for the emergence and spread of antimicrobial-resistant pathogens. Thus, there is a need to discover new broad spectrum antimicrobials, such as antiprotozoals, useful in combating microorganisms, especially those with multi-drug-resistance.

Boron-containing molecules, such as oxaboroles, useful as antimicrobials have been described previously, such as in U.S. Pat. Pubs. US20060234981 and US20070155699. Generally speaking, an oxaborole has the following structure and substituent numbering system:

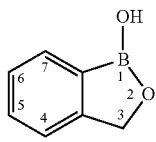

It has now been discovered that certain classes of oxaboroles which are surprisingly effective antiprotozoals. This, and other uses of these oxaboroles are described herein.

SUMMARY OF THE INVENTION

This invention provides, among other things, novel compounds useful for treating protozoa infections, pharmaceutical compositions containing such compounds, as well as combinations of these compounds with at least one additional therapeutically effective agent.

BRIEF DESCRIPTION OF THE DRAWINGS

FIG. 1A-FIG. 1B Biological data for exemplary compounds of the invention is provided in FIG. 1A-FIG. 1B.

FIG. 2 Biological data for exemplary compounds of the invention is provided in FIG. 2.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino) pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2(pddf)$ is 1,1'-Bis (diphenylphosphino) ferrocene]dichloropalladium(II); Pd/C is the catalyst known as palladium on carbon; $Pd_2(dba)_3$ is an organometallic catalyst known as tris(dibenzylideneacetone) dipalladium(0); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr. or Pyr or Py as used herein means Pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TFA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride; 3-F-4-$NO_2$-$PhSO_2Cl$ is 3-fluoro-4-nitrophenylsulfonyl chloride; 2-MeO-4-NO$_2$-PhSO$_2$Cl is 2-methoxy-4-nitrophenyl-sulfonyl chloride; and (EtO)$_2$POCH$_2$COOEt is a triethyl-ester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

"Combination of the invention," as used herein refers to the compounds and antiprotozoals discussed herein as well as acids, bases, salt forms (such as pharmaceutically acceptable salts), prodrugs, solvates and hydrates of these compounds and antiprotozoals.

"Boron containing compounds", as used herein, refers to the compounds of the invention that contain boron as part of their chemical formula.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "poly" as used herein means at least 2. For example, a polyvalent metal ion is a metal ion having a valency of at least 2.

"Moiety" refers to a radical of a molecule that is attached to the remainder of the molecule.

The symbol ∼∼∼, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkane.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —CH$_2$—CH═N—OCH$_3$, and —CH═CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to (2m'+1), where m' is the total number of carbon atoms in such radical. R', R", R'", R"" and R""' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted $C_1$ or $C_2$ or $C_3$ or $C_4$ or $C_5$ or $C_6$ alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, *J. Chem. Ed.* 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). The compounds may also be labeled with stable isotopes such as deuterium. All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the animal. Representative carriers include water, oils, both vegetable and mineral, cream bases, lotion bases, ointment bases and the like. These bases include suspending agents, thickeners, penetration enhancers, and the like. Their formulation is well known to those in the pharmaceutical arts. Additional information concerning carriers can be found in *Remington: The Science and Practice of Pharmacy*, 21st Ed., Lippincott, Williams & Wilkins (2005) which is incorporated herein by reference.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the animal. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal skin, nail, hair, claw or hoof using a diffusion cell apparatus. A diffusion cell is described by Merritt et al. Diffusion Apparatus for Skin Penetration, *J of Controlled Release*, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical composition administered to a subject via the oral cavity. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

The term, "prodrug", as defined herein, is a derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more amenable to the animal, by minimizing the frequency (e.g., once daily) or route of dosing (e.g., oral), or to improve the taste or odor if given orally, or to minimize pain if given parenterally.

In some embodiments, the prodrugs are chemically more stable than the active drug, thereby improving formulation and delivery of the parent drug, compared to the drug alone.

Prodrugs for carboxylic acid analogs of the invention may include a variety of esters. In an exemplary embodiment, the pharmaceutical compositions of the invention include a carboxylic acid ester. In an exemplary embodiment, the prodrug is suitable for treatment/prevention of those diseases and conditions that require the drug molecule to cross the blood brain barrier. In an exemplary embodiment, the prodrug enters the brain, where it is converted into the active form of the drug molecule. In one embodiment, a prodrug is used to enable an active drug molecule to reach the inside of the eye after topical application of the prodrug to the eye. Additionally, a prodrug can be converted to its parent compound by chemical or biochemical methods in an ex vivo environment. For example, a prodrug can be slowly converted to its parent compound when placed in a transdermal patch reservoir with a suitable enzyme or chemical reagent.

"Antibiotic", as used herein, is a compound which can kill or inhibit the growth of bacteria. The term antibiotic is broad enough to encompass acids, bases, salt forms (such as pharmaceutically acceptable salts), prodrugs, solvates and hydrates of the antibiotic compound.

"Antiprotozoal" or "antiprotozoa", as used herein, is a compound which can kill or inhibit the growth of protozoa. The term antiprotozoal or antiprotozoa is broad enough to encompass acids, bases, salt forms (such as pharmaceutically acceptable salts), prodrugs, solvates and hydrates of the antiprotozoal or antiprotozoa compound.

The term "microbial infection" or "infection by a microorganism" refers to any infection of a host by an infectious agent including, but not limited to, viruses, bacteria, mycobacteria, fungus and parasites (see, e.g., Harrison's Principles of Internal Medicine, pp. 93-98 (Wilson et al., eds., 12th ed. 1991); Williams et al., *J. of Medicinal Chem.* 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of an enzyme, such as a beta-lactamase or a leucyl t-RNA synthetase.

Boron is able to form additional covalent or dative bonds with oxygen, sulfur or nitrogen under some circumstances in this invention.

Embodiments of the invention also encompass compounds that are poly- or multi-valent species, including, for example, species such as dimers, trimers, tetramers and higher homologs of the compounds of use in the invention or reactive analogues thereof.

"Salt counterion", as used herein, refers to positively charged ions that associate with a compound of the invention when the boron is fully negatively or partially negatively charged. Examples of salt counterions include $H^+$, $H_3O^+$, ammonium, potassium, calcium, magnesium, organic amino (such as choline or diethylamine or amino acids such as d-arginine, l-arginine, d-lysine, l-lysine), and sodium.

The compounds comprising a boron bonded to a carbon and three heteroatoms (such as three oxygens described in this section) can optionally contain a fully negatively charged boron or partially negatively charged boron. Due to the negative charge, a positively charged counterion may associate with this compound, thus forming a salt. Examples of positively charged counterions include $H^+$, $H_3O^+$, ammonium, potassium, calcium, magnesium, organic amino (such as choline or diethylamine or amino acids such as d-arginine, l-arginine, d-lysine, l-lysine), and sodium. These salts of the compounds are implicitly contained in descriptions of these compounds.

II. Introduction

The invention provides novel boron compounds. The novel compounds, as well as pharmaceutical compositions containing such compounds or combinations of these compounds with at least one additional therapeutically effective agent, can be used for, among other things, treating protozoal infections.

III. The Compounds

III.a) Cyclic Boronic Esters

In one aspect, the invention provides a compound of the invention. In an exemplary embodiment, the invention is a compound described herein. In an exemplary embodiment, the invention is a compound according to a formula described herein.

In another aspect, the invention provides a compound, or a salt thereof, having a structure according to the following formula:

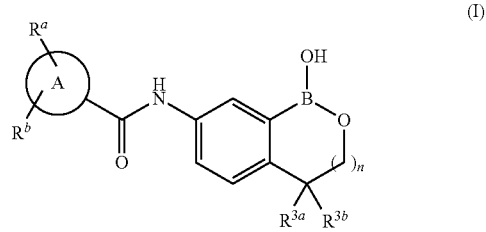

(I)

wherein A is phenyl or pyridinyl; $R^a$ is substituted or unsubstituted heteroaryl or substituted or unsubstituted heterocycloalkyl; $R^b$ is halogen or substituted or unsubstituted alkyl; n is 0 or 1; when n is 0, then $R^{3a}$ is H or unsubstituted $C_1$ or $C_2$ or $C_3$ or $C_4$ or $C_5$ or $C_6$ alkyl; $R^{3b}$ is H or unsubstituted $C_1$ or $C_2$ or $C_3$ or $C_4$ or $C_5$ or $C_6$ alkyl; with the proviso that $R^{3a}$ and $R^{3b}$, along with the atom to which they are attached, are optionally joined to form a 3 or 4 or 5 or 6 membered ring with the proviso that $R^{3a}$ and $R^{3b}$ cannot both be H; when n is 1, then $R^3$ is H and $R^{3b}$ is H.

In another aspect, the invention provides a compound, or a salt thereof, having a structure according to the following formula:

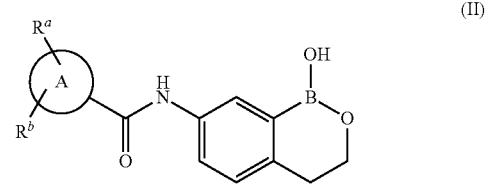

(II)

wherein A is phenyl or pyridinyl; $R^a$ is substituted or unsubstituted heteroaryl or substituted or unsubstituted heterocycloalkyl; $R^b$ is halogen or substituted or unsubstituted alkyl.

In another aspect, the invention provides a compound, or a salt thereof, having a structure according to the following formula:

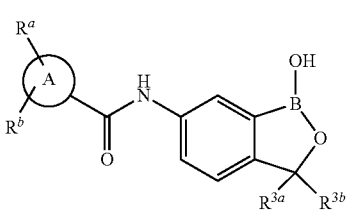
(III)

wherein A is phenyl or pyridinyl; $R^a$ is substituted or unsubstituted heteroaryl or substituted or unsubstituted heterocycloalkyl; $R^b$ is halogen or substituted or unsubstituted alkyl; $R^{3a}$ is H or unsubstituted $C_1$ or $C_2$ or $C_3$ or $C_4$ or $C_5$ or $C_6$ alkyl; $R^{3b}$ is H or unsubstituted $C_1$ or $C_2$ or $C_3$ or $C_4$ or $C_5$ or $C_6$ alkyl; with the proviso that $R^{3a}$ and $R^{3b}$, along with the atom to which they are attached, are optionally joined to form a 3 or 4 or 5 or 6 membered ring.

In another aspect, the invention provides a compound, or a salt thereof, having a structure according to the following formula:

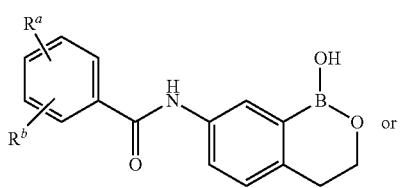

or

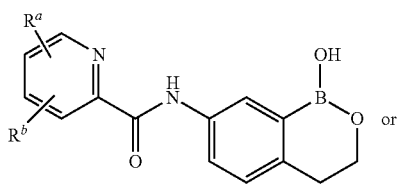

wherein $R^a$ is substituted or unsubstituted heteroaryl or substituted or unsubstituted heterocycloalkyl; $R^b$ is halogen or substituted or unsubstituted alkyl. In an exemplary embodiment, $R^b$ is halogen or unsubstituted alkyl or alkyl substituted with one, two or three halogens, and $R^a$ is substituted or unsubstituted morpholinyl or substituted or unsubstituted pyrazolyl or substituted or unsubstituted pyrrolopyridinyl or substituted or unsubstituted pyrrolidinyl or substituted or unsubstituted piperizinyl or substituted or unsubstituted pyridazinyl or substituted or unsubstituted piperidinyl or substituted or unsubstituted imidazolyl or substituted or unsubstituted azetidinyl or substituted or unsubstituted triazolyl.

In another aspect, the invention provides a compound, or a salt thereof, having a structure according to the following formula:

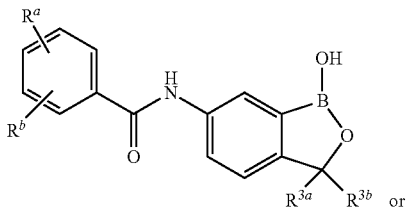

or

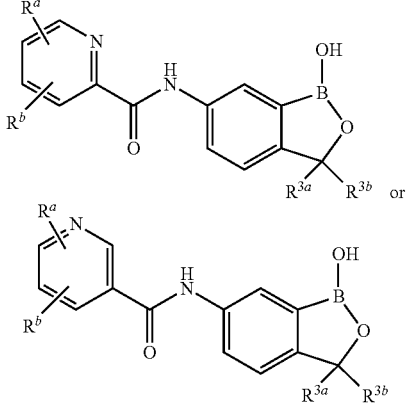

wherein $R^a$ is substituted or unsubstituted heteroaryl or substituted or unsubstituted heterocycloalkyl; $R^b$ is halogen or substituted or unsubstituted alkyl; $R^{3a}$ is H or unsubstituted $C_1$ or $C_2$ or $C_3$ or $C_4$ or $C_5$ or $C_6$ alkyl; $R^{3b}$ is H or unsubstituted $C_1$ or $C_2$ or $C_3$ or $C_4$ or $C_5$ or $C_6$ alkyl; with the proviso that $R^{3a}$ and $R^{3b}$, along with the atom to which they are attached, are optionally joined to form a 3 or 4 or 5 or 6 membered ring.

In another aspect, the invention provides a compound, or a salt thereof, having a structure according to the following formula:

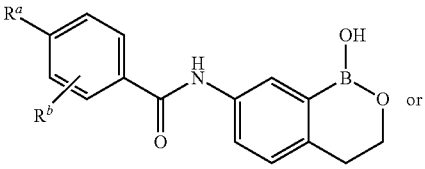

or

or

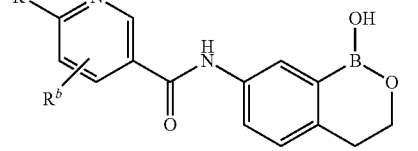

wherein $R^a$ and $R^b$ are as described herein. In an exemplary embodiment, $R^b$ is halogen or unsubstituted alkyl or alkyl substituted with one, two or three halogens, and $R^a$ is substituted or unsubstituted morpholinyl or substituted or unsubstituted pyrazolyl or substituted or unsubstituted pyrrolopyridinyl or substituted or unsubstituted pyrrolidinyl or substituted or unsubstituted piperizinyl or substituted or unsubstituted pyridazinyl or substituted or unsubstituted piperidinyl or substituted or unsubstituted imidazolyl or substituted or unsubstituted azetidinyl or substituted or unsubstituted triazolyl.

In another aspect, the invention provides a compound, or a salt thereof, having a structure according to the following formula:

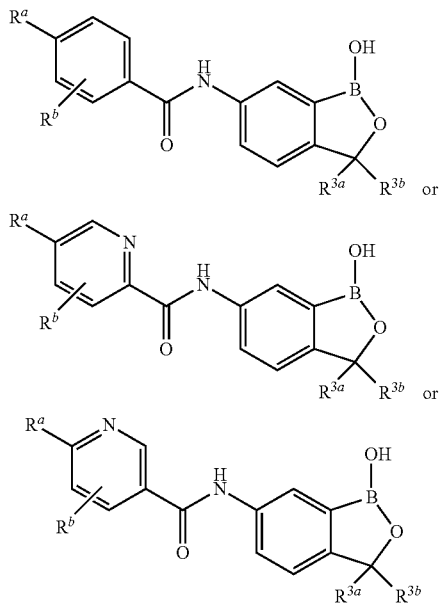

wherein $R^a$, $R^b$, $R^{3a}$, and $R^{3b}$ are as described herein.

In another aspect, the invention provides a compound, or a salt thereof, having a structure according to the following formula:

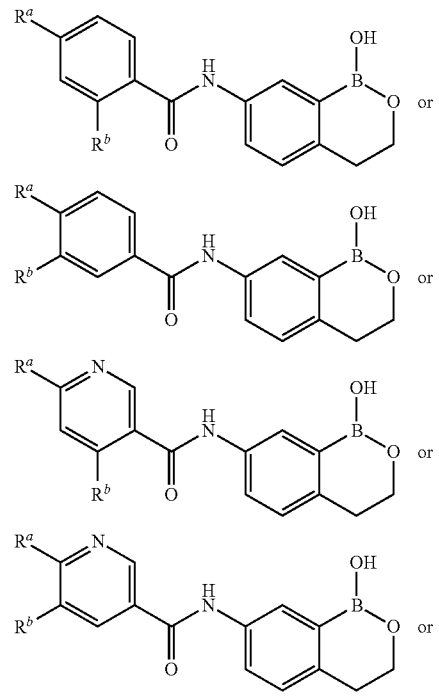

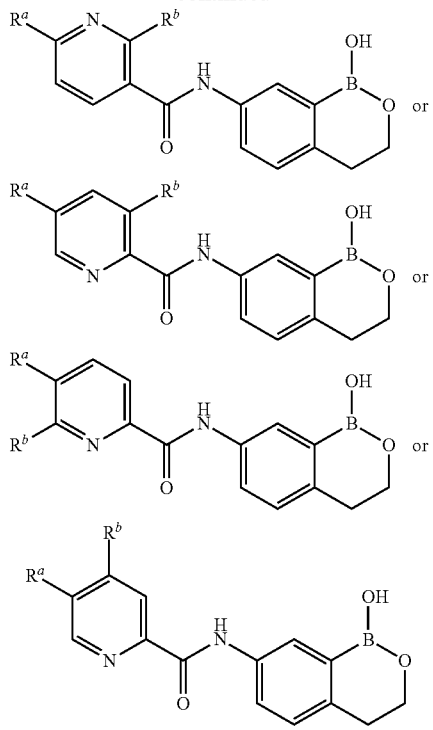

wherein $R^a$ and $R^b$ are as described herein. In an exemplary embodiment, $R^b$ is halogen or unsubstituted alkyl or alkyl substituted with one, two or three halogens, and $R^a$ is substituted or unsubstituted morpholinyl or substituted or unsubstituted pyrazolyl or substituted or unsubstituted pyrrolopyridinyl or substituted or unsubstituted pyrrolidinyl or substituted or unsubstituted piperizinyl or substituted or unsubstituted pyridazinyl or substituted or unsubstituted piperidinyl or substituted or unsubstituted imidazolyl or substituted or unsubstituted azetidinyl or substituted or unsubstituted triazolyl. In an exemplary embodiment, $R^b$ is halogen or unsubstituted $C_1$ or $C_2$ or $C_3$ alkyl or $C_1$ or $C_2$ or $C_3$ alkyl substituted with one, two or three halogens, and $R^a$ is substituted or unsubstituted morpholinyl or substituted or unsubstituted pyrazolyl or substituted or unsubstituted pyrrolopyridinyl or substituted or unsubstituted piperizinyl or substituted or unsubstituted azetidinyl. In an exemplary embodiment, $R^b$ is F or Cl or $CF_3$ or $CH_3$, and $R^a$ is substituted or unsubstituted morpholinyl or substituted or unsubstituted pyrazolyl or substituted or unsubstituted pyrrolopyridinyl or substituted or unsubstituted piperizinyl or substituted or unsubstituted azetidinyl.

In an exemplary embodiment, the compound, or a salt thereof, has a structure according to the following formula which is:

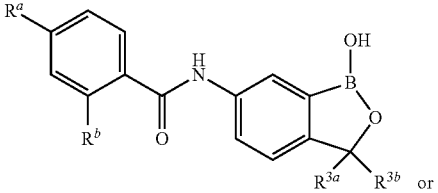

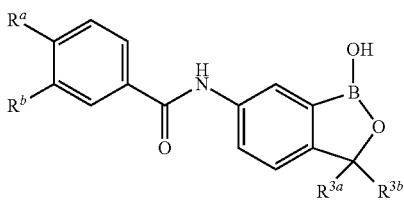

wherein $R^a$, $R^b$, $R^{3a}$, and $R^{3b}$ are as described herein.

In an exemplary embodiment, the invention provides a compound, or a salt thereof, having a structure according to the following formula:

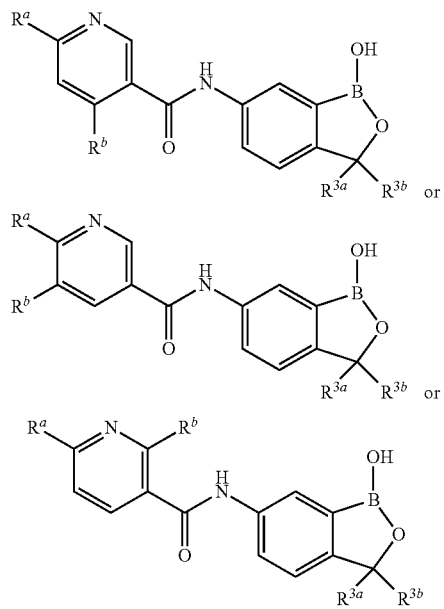

wherein $R^a$, $R^b$, $R^3$, and $R^{3b}$ are as described herein.

In an exemplary embodiment, the invention provides a compound, or a salt thereof, having a structure according to the following formula:

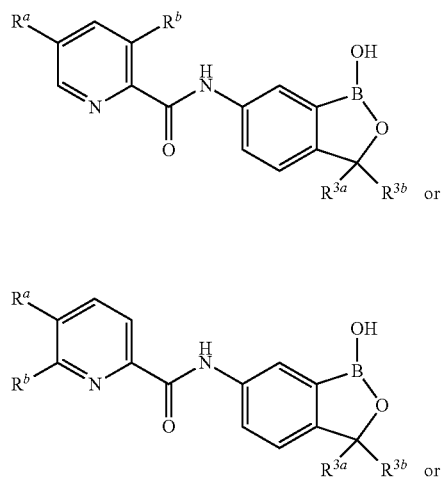

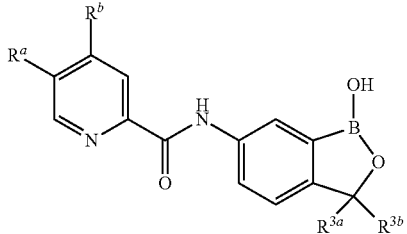

wherein $R^a$, $R^b$, $R^{3a}$, and $R^{3b}$ are as described herein.

In an exemplary embodiment, for any of the boron-containing compound formulas described herein, $R^b$, $R^{3a}$, and $R^{3b}$ are as described herein, and $R^a$ is substituted or unsubstituted morpholinyl or substituted or unsubstituted pyrazolyl or substituted or unsubstituted pyrrolopyridinyl or substituted or unsubstituted pyrrolidinyl or substituted or unsubstituted piperizinyl or substituted or unsubstituted pyridazinyl or substituted or unsubstituted piperidinyl or substituted or unsubstituted imidazolyl or substituted or unsubstituted azetidinyl or substituted or unsubstituted triazolyl.

In an exemplary embodiment, for any of the boron-containing compound formulas described herein, $R^a$, $R^{3a}$, and $R^{3b}$ are as described herein, and $R^b$ is halogen. In an exemplary embodiment, for any of the boron-containing compound formulas described herein, $R^a$, $R^{3a}$, and $R^{3b}$ are as described herein, and $R^b$ is fluorine. In an exemplary embodiment, for any of the boron-containing compound formulas described herein, $R^a$, $R^{3a}$, and $R^{3b}$ are as described herein, and $R^b$ is chlorine. In an exemplary embodiment, for any of the boron-containing compound formulas described herein, $R^a$, $R^{3a}$, and $R^{3b}$ are as described herein, and $R^b$ is bromine. In an exemplary embodiment, for any of the boron-containing compound formulas described herein, $R^a$, $R^{3a}$, and $R^{3b}$ are as described herein, and $R^b$ is iodine. In an exemplary embodiment, for any of the boron-containing compound formulas described herein, $R^a$, $R^{3a}$, and $R^{3b}$ are as described herein, and $R^b$ is unsubstituted $C_1$-$C_6$ alkyl. In an exemplary embodiment, for any of the boron-containing compound formulas described herein, $R^a$, $R^{3a}$, and $R^{3b}$ are as described herein, and $R^b$ is methyl or ethyl or propyl or isopropyl. In an exemplary embodiment, for any of the boron-containing compound formulas described herein, $R^a$, $R^{3a}$, and $R^{3b}$ are as described herein, and $R^b$ is methyl. In an exemplary embodiment, for any of the boron-containing compound formulas described herein, $R^a$, $R^{3a}$, and $R^{3b}$ are as described herein, and $R^b$ is alkyl substituted with at least one halogen. In an exemplary embodiment, for any of the boron-containing compound formulas described herein, $R^a$, $R^{3a}$, and $R^{3b}$ are as described herein, and $R^b$ is alkyl substituted with at least two, or at least three, halogens. In an exemplary embodiment, for any of the boron-containing compound formulas described herein, $R^a$, $R^{3a}$, and $R^{3b}$ are as described herein, and $R^b$ is alkyl substituted with at least one fluorine. In an exemplary embodiment, for any of the boron-containing compound formulas described herein, $R^a$, $R^{3a}$, and $R^{3b}$ are as described herein, and $R^b$ is alkyl substituted with at least one chlorine. In an exemplary embodiment, for any of the boron-containing compound formulas described herein, $R^a$, $R^{3a}$, and $R^{3b}$ are as described herein, and $R^b$ is alkyl substituted with at least two, or at least three, fluorines. In an exemplary embodiment, for any of the boron-containing compound formulas described herein, $R^a$, $R^{3a}$, and $R^{3b}$ are as described herein, and $R^b$ is alkyl substituted with at least two, or at least three, chlorines. In an exemplary embodiment, for any of the boron-containing compound formulas described herein, $R^a$, $R^{3a}$, and $R^{3b}$ are as described herein, and $R^b$ is trifluoromethyl. In an exemplary embodiment, for a formula described herein, $R^a$, $R^{3a}$, and $R^{3b}$ are as described herein, and $R^b$ is $CH_2F$ or $CHF_2$.

In an exemplary embodiment, for any of the boron-containing compound formulas described herein, $R^a$, $R^b$, and $R^{3b}$ are as described herein, $R^{3a}$ is methyl. In an exemplary embodiment, for any of the boron-containing compound formulas described herein, $R^a$, $R^b$, and $R^{3b}$ are as described herein, $R^{3a}$ is ethyl. In an exemplary embodiment, for any of the boron-containing compound formulas described herein, $R^a$, $R^b$, and $R^{3b}$ are as described herein, $R^{3a}$ is unsubstituted $C_3$ alkyl. In an exemplary embodiment, for any of the boron-containing compound formulas described herein, $R^a$, $R^b$, and $R^{3b}$ are as described herein, $R^{3a}$ is unsubstituted $C_4$ alkyl. In an exemplary embodiment, for any of the boron-containing compound formulas described herein, $R^a$, $R^b$, and $R^{3b}$ are as described herein, $R^{3a}$ is unsubstituted $C_5$ alkyl. In an exemplary embodiment, for any of the boron-containing compound formulas described herein, $R^a$, $R^b$, and $R^{3b}$ are as described herein, $R^{3a}$ is unsubstituted $C_6$ alkyl.

In an exemplary embodiment, for any of the boron-containing compound formulas described herein, $R^a$, $R^b$, and $R^{3b}$ are as described herein, $R^{3b}$ is methyl. In an exemplary embodiment, for any of the boron-containing compound formulas described herein, $R^a$, $R^b$, and $R^{3b}$ are as described herein, $R^{3b}$ is ethyl. In an exemplary embodiment, for any of the boron-containing compound formulas described herein, $R^a$, $R^b$, and $R^{3b}$ are as described herein, $R^{3b}$ is unsubstituted $C_3$ alkyl. In an exemplary embodiment, for any of the boron-containing compound formulas described herein, $R^a$, $R^b$, and $R^{3b}$ are as described herein, $R^{3b}$ is unsubstituted $C_4$ alkyl. In an exemplary embodiment, for any of the boron-containing compound formulas described herein, $R^a$, $R^b$, and $R^{3b}$ are as described herein, $R^{3b}$ is unsubstituted $C_5$ alkyl. In an exemplary embodiment, for any of the boron-containing compound formulas described herein, $R^a$, $R^b$, and $R^{3b}$ are as described herein, $R^{3b}$ is unsubstituted $C_6$ alkyl.

In an exemplary embodiment, for any of the boron-containing compound formulas described herein, $R^a$ and $R^b$ are as described herein, $R^{3a}$ is methyl and $R^{3b}$ is H. In an exemplary embodiment, for any of the boron-containing compound formulas described herein, $R^a$ and $R^b$ are as described herein, $R^{3a}$ is ethyl and $R^{3b}$ is H. In an exemplary embodiment, for any of the boron-containing compound formulas described herein, $R^a$ and $R^b$ are as described herein, $R^{3a}$ is unsubstituted $C_3$ alkyl and $R^{3b}$ is H. In an exemplary embodiment, for any of the boron-containing compound formulas described herein, $R^a$ and $R^b$ are as described herein, $R^{3a}$ is unsubstituted $C_4$ alkyl and $R^{3b}$ is H. In an exemplary embodiment, for any of the boron-containing compound formulas described herein, $R^a$ and $R^b$ are as described herein, $R^{3a}$ is unsubstituted $C_5$ alkyl and $R^{3b}$ is H. In an exemplary embodiment, for any of the boron-containing compound formulas described herein, $R^a$ and $R^b$ are as described herein, $R^{3a}$ is unsubstituted $C_6$ alkyl and $R^{3b}$ is H.

In an exemplary embodiment, for any of the boron-containing compound formulas described herein, $R^a$ and $R^b$ are as described herein, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the boron-containing compound formulas described herein, $R^a$ and $R^b$ are as described herein, $R^{3a}$ is methyl and $R^{3b}$ is methyl. In an exemplary embodiment, for any of the boron-containing compound formulas described herein, $R^a$ and $R^b$ are as described herein, $R^{3a}$ is methyl and $R^{3b}$ is ethyl. In an exemplary embodiment, for any of the boron-containing compound formulas described herein, $R^a$ and $R^b$ are as described herein, $R^{3a}$ is methyl and $R^{3b}$ is unsubstituted $C_3$ alkyl. In an exemplary embodiment, for any of the boron-containing compound formulas described herein, $R^a$ and $R^b$ are as described herein, $R^{3a}$ is methyl and $R^{3b}$ is unsubstituted $C_4$ alkyl. In an exemplary embodiment, for any of the boron-containing compound formulas described herein, $R^a$ and $R^b$ are as described herein, $R^{3a}$ is methyl and $R^{3b}$ is unsubstituted $C_5$ alkyl. In an exemplary embodiment, for any of the boron-containing compound formulas described herein, $R^a$ and $R^b$ are as described herein, $R^{3a}$ is methyl and $R^{3b}$ is unsubstituted $C_6$ alkyl.

In an exemplary embodiment, for any of the boron-containing compound formulas described herein, $R^a$ and $R^b$ are as described herein, $R^{3a}$ is H and $R^{3b}$ is H. In an exemplary embodiment, for any of the boron-containing compound formulas described herein, $R^a$ and $R^b$ are as described herein, $R^{3a}$ is methyl and $R^{3b}$ is methyl. In an exemplary embodiment, for any of the boron-containing compound formulas described herein, $R^a$ is as described herein, $R^b$ is fluorine, $R^{3a}$ is H and $R^{3b}$ is H. In an exemplary embodiment, $R^a$ is as described herein, $R^b$ is fluorine, $R^{3a}$ is methyl and $R^{3b}$ is methyl. In an exemplary embodiment, for any of the boron-containing compound formulas described herein, $R^a$ is as described herein, $R^b$ is chlorine, $R^{3a}$ is H and $R^{3b}$ is H. In an exemplary embodiment, for any of the boron-containing compound formulas described herein, $R^a$ is as described herein, $R^b$ is chlorine, $R^{3a}$ is methyl and $R^{3b}$ is methyl. In an exemplary embodiment, for any of the boron-containing compound formulas described herein, $R^a$ is as described herein, $R^b$ is bromine, $R^{3a}$ is H and $R^{3b}$ is H. In an exemplary embodiment, for any of the boron-containing compound formulas described herein, $R^a$ is as described herein, $R^b$ is bromine, $R^{3a}$ is methyl and $R^{3b}$ is methyl.

In an exemplary embodiment, for any of the boron-containing compound formulas described herein, $R^a$ is as described herein, $R^b$ is $CH_3$, $R^{3a}$ is H and $R^{3b}$ is H. In an exemplary embodiment, for any of the boron-containing compound formulas described herein, $R^a$ is as described herein, $R^b$ is $CH_3$, $R^3$ is methyl and $R^{3b}$ is methyl. In an exemplary embodiment, for any of the boron-containing compound formulas described herein, $R^a$ is as described herein, $R^b$ is $CH_2F$, $R^{3a}$ is H and $R^{3b}$ is H. In an exemplary embodiment, for any of the boron-containing compound formulas described herein, $R^a$ is as described herein, $R^b$ is $CH_2F$, $R^{3a}$ is methyl and $R^{3b}$ is methyl. In an exemplary embodiment, for any of the boron-containing compound formulas described herein, $R^a$ is as described herein, $R^b$ is $CHF_2$, $R^{3a}$ is H and $R^{3b}$ is H. In an exemplary embodiment, for any of the boron-containing compound formulas described herein, $R^a$ is as described herein, $R^b$ is $CHF_2$, $R^{3a}$ is methyl and $R^{3b}$ is methyl. In an exemplary embodiment, for any of the boron-containing compound formulas described herein, $R^a$ is as described herein, $R^b$ is $CF_3$, $R^{3a}$ is H and $R^{3b}$ is H. In an exemplary embodiment, for any of the boron-containing compound formulas described herein, $R^a$ is as described herein, $R^b$ is $CF_3$, $R^{3a}$ is methyl and $R^{3b}$ is methyl.

In an exemplary embodiment, the compound, or a salt thereof, has a structure according to formulae (I) or (II) or (III), wherein A is phenyl or pyridinyl; $R^a$ is unsubstituted azetidinyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is unsubstituted pyrrolidinyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is unsubstituted oxopyrrolidinyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is unsubstituted 2-oxopyrrolidinyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is unsubstituted pyrazolyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is pyrazolyl substituted with unsubstituted $C_1$ or $C_2$ or $C_3$ or $C_4$ or $C_5$ or $C_6$ alkyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is pyrazolyl substituted with halogen; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is unsubstituted imidazolyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is unsubstituted triazolyl; and $R^b$ is F or Cl or $CF_3$. In an exemplary embodiment, the compound, or a salt thereof, has a structure according to formulae (I) or (II) or (III), wherein A is phenyl or pyridinyl; $R^a$ is unsubstituted [1,2,4]triazolyl; and $R^b$ is F or Cl or $CF_3$. In an exemplary embodiment, the compound, or a salt thereof, has a structure according to formulae (I) or (II) or (III), wherein A is phenyl or pyridinyl; $R^a$ is unsubstituted [4H-1,2,4]triazolyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is unsubstituted piperidinyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is piperidinyl substituted with unsubstituted $C_1$ or $C_2$ or $C_3$ or $C_4$ or $C_5$ or $C_6$ alkyl; and $R^b$ is F or Cl or $CF_3$. In an exemplary embodiment, the compound, or a salt thereof, has a structure according to formulae (I) or (II) or (III), wherein A is phenyl or pyridinyl; $R^a$ is methylpiperidinyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is piperidinyl disubstituted with unsubstituted $C_1$ or $C_2$ or $C_3$ or $C_4$ or $C_5$ or $C_6$ alkyl; and $R^b$ is F or Cl or $CF_3$. In an exemplary embodiment, the compound, or a salt thereof, has a structure according to formulae (I) or (II) or (III), wherein A is phenyl or pyridinyl; $R^a$ is dimethylpiperidinyl; and $R^b$ is F or Cl or $CF_3$. In an exemplary embodiment, the compound, or a salt thereof, has a structure according to formulae (I) or (II) or (III), wherein A is phenyl or pyridinyl; $R^a$ is 4,4-dimethyl-piperidinyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is unsubstituted piperazinyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is piperazinyl substituted with unsubstituted $C_1$ or $C_2$ or $C_3$ or $C_4$ or $C_5$ or $C_6$ alkyl; and $R^b$ is F or Cl or $CF_3$. In an exemplary embodiment, the compound, or a salt thereof, has a structure according to formulae (I) or (II) or (III), wherein A is phenyl or pyridinyl; $R^a$ is methylpiperazinyl; and $R^b$ is F or Cl or $CF_3$. In an exemplary embodiment, the compound, or a salt thereof, has a structure according to formulae (I) or (II) or (III), wherein A is phenyl or pyridinyl; $R^a$ is 4-methylpiperazinyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is unsubstituted morpholinyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is unsubstituted pyrrolo[2,3-b]pyridinyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is pyrrolo[2,3-b]pyridinyl substituted with halogen; and $R^b$ is F or Cl or $CF_3$. In an exemplary embodiment, the compound, or a salt thereof, has a structure according to formulae (I) or (II) or (III), wherein A is phenyl or pyridinyl; $R^a$ is pyrrolo[2,3-b]pyridinyl substituted with chlorine; and $R^b$ is F or Cl or $CF_3$. In an exemplary embodiment, the compound, or a salt thereof, has a structure according to formulae (I) or (II) or (III), wherein A is phenyl or pyridinyl; $R^a$ is 3-chloro pyrrolo[2,3-b]pyridinyl; and $R^b$ is F or Cl or $CF_3$.

In an exemplary embodiment, the compound, or a salt thereof, has a structure according to formulae (I) or (II) or (III), wherein A is phenyl or pyridinyl; $R^a$ is unsubstituted pyridazinyl; and $R^b$ is F or Cl or $CF_3$. In an exemplary embodiment, the compound, or a salt thereof, has a structure according to formulae (I) or (II) or (III), wherein A is phenyl or pyridinyl; $R^a$ is 6-oxo-pyridazinyl; and $R^b$ is F or Cl or $CF_3$. In an exemplary embodiment, the compound, or a salt thereof, has a structure according to formulae (I) or (II) or (III), wherein A is phenyl or pyridinyl; $R^a$ is 6-oxo-6H-pyridazinyl; and $R^b$ is F or Cl or $CF_3$.

In another aspect, the invention provides a compound, or a salt thereof, having a structure according to the following formula:

-continued
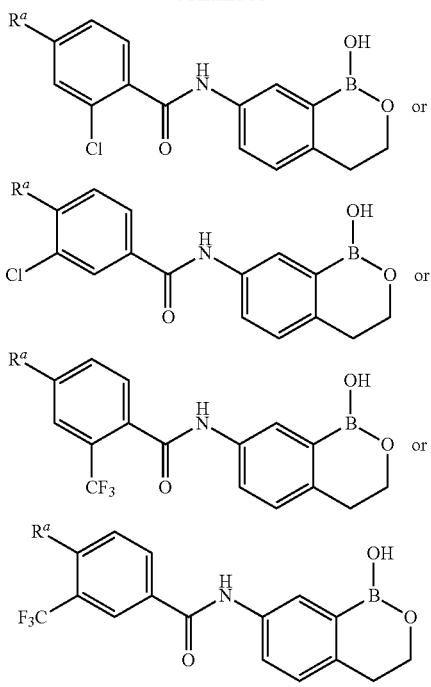
wherein R$^a$ is as described herein.
In another aspect, the invention provides a compound, or a salt thereof, having a structure according to the following formula:
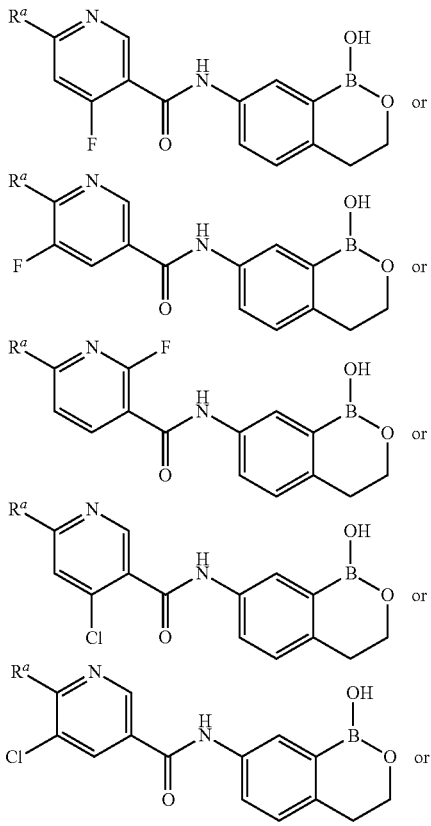
-continued
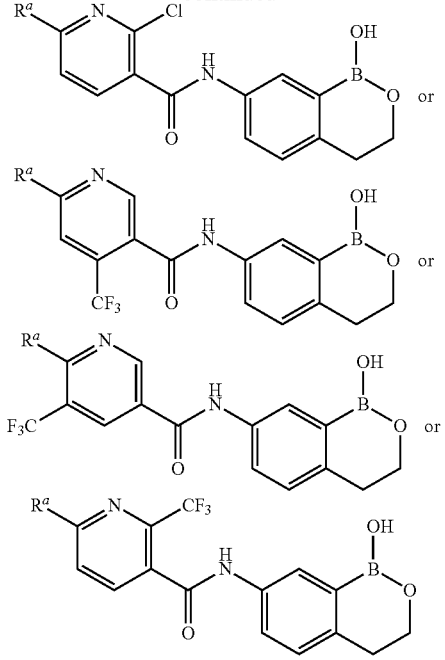
wherein R$^a$ is as described herein.
In another aspect, the invention provides a compound, or a salt thereof, having a structure according to the following formula:
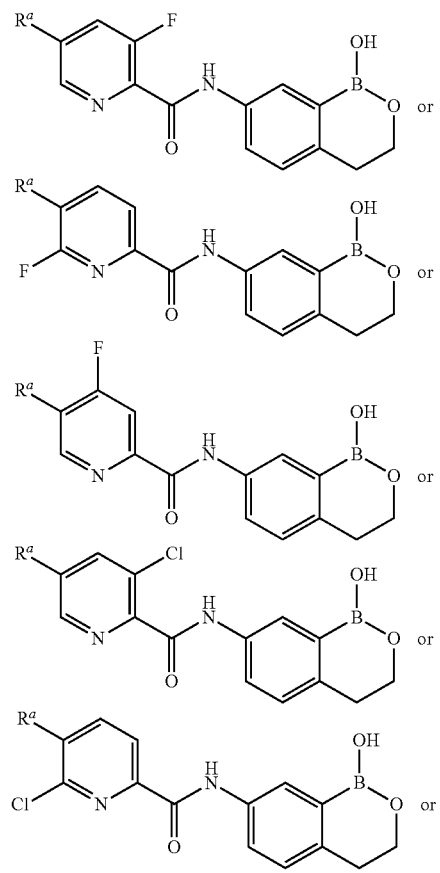

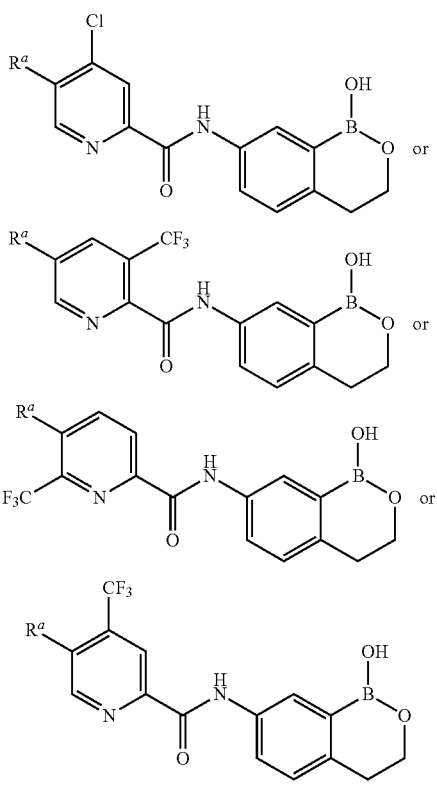

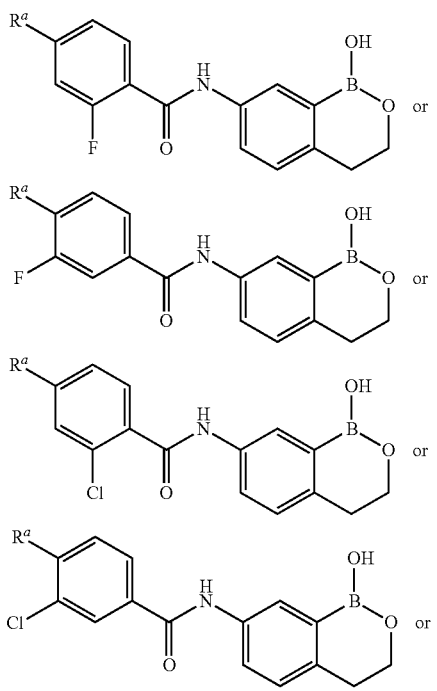

wherein $R^a$ is as described herein.

In another aspect, the invention provides a compound, or a salt thereof, having a structure according to the following formula:

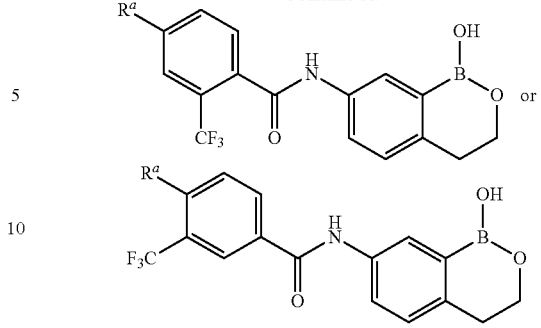

wherein $R^a$ is as described herein.

In another aspect, the invention provides a compound, or a salt thereof, having a structure according to the following formula:

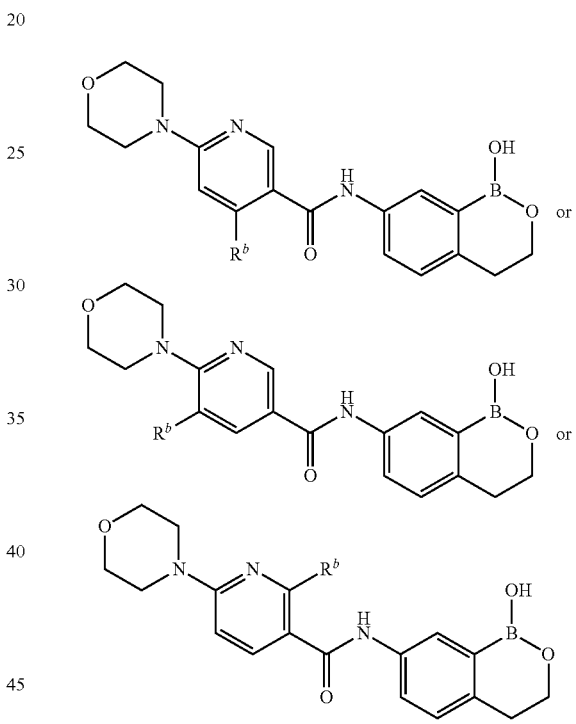

wherein $R^b$ is as described herein. In an exemplary embodiment, for any of the boron-containing compound formulas described in this paragraph, $R^b$ is halogen. In an exemplary embodiment, for any of the boron-containing compound formulas described in this paragraph, $R^b$ is unsubstituted $C_1$ or $C_2$ or $C_3$ or $C_4$ or $C_5$ or $C_6$ alkyl. In an exemplary embodiment, for any of the boron-containing compound formulas described in this paragraph, $R^b$ is alkyl substituted with at least one halogen. In an exemplary embodiment, for any of the boron-containing compound formulas described in this paragraph, $R^b$ is alkyl substituted with at least two, or at least three, halogens. In an exemplary embodiment, for any of the boron-containing compound formulas described in this paragraph, $R^b$ is alkyl substituted with at least one fluorine. In an exemplary embodiment, for any of the boron-containing compound formulas described in this paragraph, $R^b$ is alkyl substituted with at least one chlorine. In an exemplary embodiment, for any of the boron-containing compound formulas described in this paragraph, $R^b$ is alkyl substituted with at least two, or at least three, fluorines. In an exemplary embodiment, for any of the boron-containing compound formulas described in this paragraph, $R^b$ is alkyl substituted with at least two, or at least three, chlorines. In an exemplary embodiment, for any of the boron-containing compound formulas described in this paragraph, $R^b$ is $CH_2F$ or $CHF_2$. In an exemplary embodiment, for any of the boron-containing compound formulas described in this paragraph, $R^b$ is fluorine. In an exemplary embodiment, for any of the boron-containing compound formulas described in this paragraph, $R^b$ is chlorine. In an exemplary embodiment, for any of the boron-containing compound formulas described in this paragraph, $R^b$ is bromine. In an exemplary embodiment, for any of the boron-containing compound formulas described in this paragraph, $R^b$ is $CF_3$.

In another aspect, the invention provides a compound, or a salt thereof, having a structure according to the following formula:

wherein $R^b$ is as described herein. In an exemplary embodiment, for any of the boron-containing compound formulas described in this paragraph, $R^b$ is halogen. In an exemplary embodiment, for any of the boron-containing compound formulas described in this paragraph, $R^b$ is unsubstituted $C_1$ or $C_2$ or $C_3$ or $C_4$ or $C_5$ or $C_6$ alkyl. In an exemplary embodiment, for any of the boron-containing compound formulas described in this paragraph, $R^b$ is alkyl substituted with at least one halogen. In an exemplary embodiment, for any of the boron-containing compound formulas described in this paragraph, $R^b$ is alkyl substituted with at least two, or at least three, halogens. In an exemplary embodiment, for any of the boron-containing compound formulas described in this paragraph, $R^b$ is alkyl substituted with at least one fluorine. In an exemplary embodiment, for any of the boron-containing compound formulas described in this paragraph, $R^b$ is alkyl substituted with at least one chlorine. In an exemplary embodiment, for any of the boron-containing compound formulas described in this paragraph, $R^b$ is alkyl substituted with at least two, or at least three, fluorines. In an exemplary embodiment, for any of the boron-containing compound formulas described in this paragraph, $R^b$ is alkyl substituted with at least two, or at least three, chlorines. In an exemplary embodiment, for any of the boron-containing compound formulas described in this paragraph, $R^b$ is $CH_2F$ or $CHF_2$. In an exemplary embodiment, for any of the boron-containing compound formulas described in this paragraph, $R^b$ is fluorine. In an exemplary embodiment, for any of the boron-containing compound formulas described in this paragraph, $R^b$ is chlorine. In an exemplary embodiment, for any of the boron-containing compound formulas described in this paragraph, $R^b$ is bromine. In an exemplary embodiment, for any of the boron-containing compound formulas described in this paragraph, $R^b$ is $CF_3$.

In another aspect, the invention provides a compound, or a salt thereof, having a structure according to the following formula:

wherein $R^b$ is as described herein. In an exemplary embodiment, for any of the boron-containing compound formulas described in this paragraph, $R^b$ is halogen. In an exemplary embodiment, for any of the boron-containing compound formulas described in this paragraph, $R^b$ is unsubstituted $C_1$ or $C_2$ or $C_3$ or $C_4$ or $C_5$ or $C_6$ alkyl. In an exemplary embodiment, for any of the boron-containing compound formulas described in this paragraph, $R^b$ is alkyl substituted with at least one halogen. In an exemplary embodiment, for any of the boron-containing compound formulas described in this paragraph, $R^b$ is alkyl substituted with at least two, or at least three, halogens. In an exemplary embodiment, for any of the boron-containing compound formulas described in this paragraph, $R^b$ is alkyl substituted with at least one fluorine. In an exemplary embodiment, for any of the boron-containing compound formulas described in this paragraph, $R^b$ is alkyl substituted with at least one chlorine. In an exemplary embodiment, for any of the boron-containing compound formulas described in this paragraph, $R^b$ is alkyl substituted with at least two, or at least three, fluorines. In an exemplary embodiment, for any of the boron-containing compound formulas described in this paragraph, $R^b$ is alkyl substituted with at least two, or at least three, chlorines. In an exemplary embodiment, for any of the boron-containing compound formulas described in this paragraph, $R^b$ is $CH_2F$ or $CHF_2$. In an exemplary embodiment, for any of the boron-containing compound formulas described in this paragraph, $R^b$ is fluorine. In an exemplary embodiment, for any of the boron-containing compound formulas described in this paragraph, $R^b$ is chlorine. In an exemplary embodiment, for any of the boron-containing compound formulas described in this paragraph, $R^b$ is bromine. In an exemplary embodiment, for any of the boron-containing compound formulas described in this paragraph, $R^b$ is $CF_3$.

In an exemplary embodiment, the compound, or a salt thereof, has a structure according to the following formula which is:

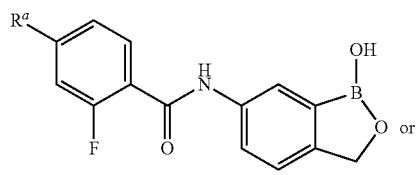

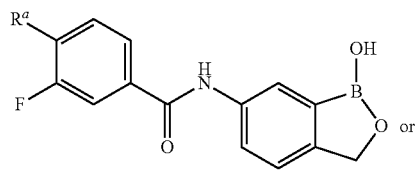

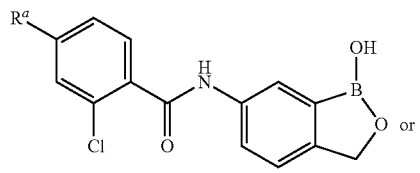

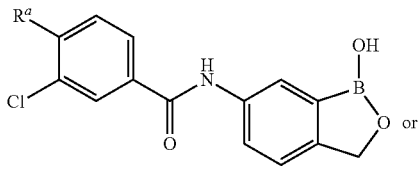

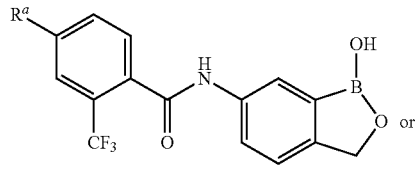

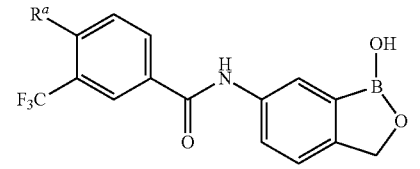

wherein $R^a$ is as described herein.

In an exemplary embodiment, the compound, or a salt thereof, has a structure according to the following formula which is:

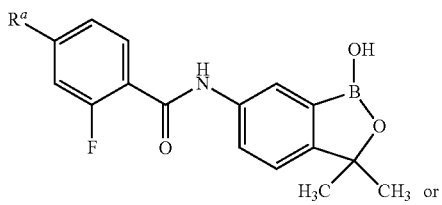

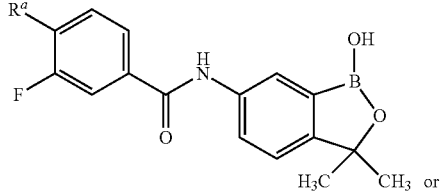

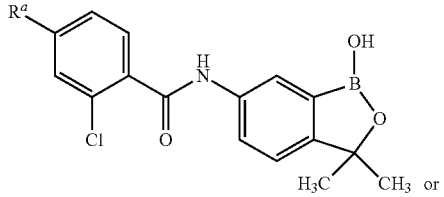

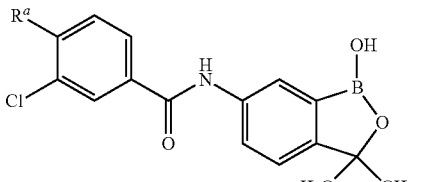

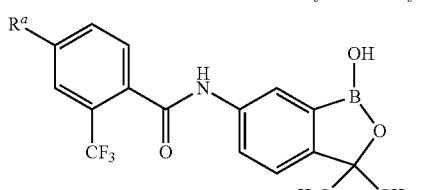

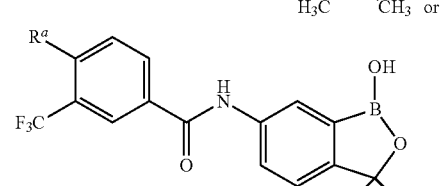

wherein $R^a$ is as described herein.

In an exemplary embodiment, the invention provides a compound, or a salt thereof, having a structure according to the following formula:

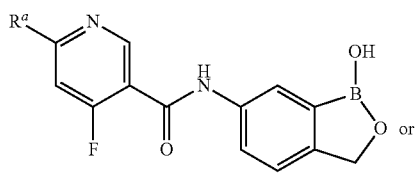

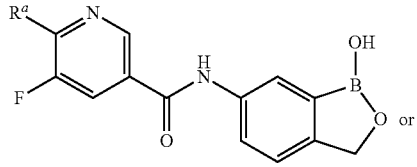

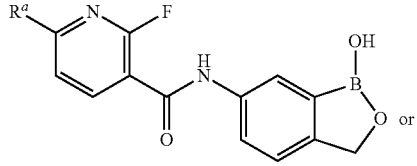

-continued

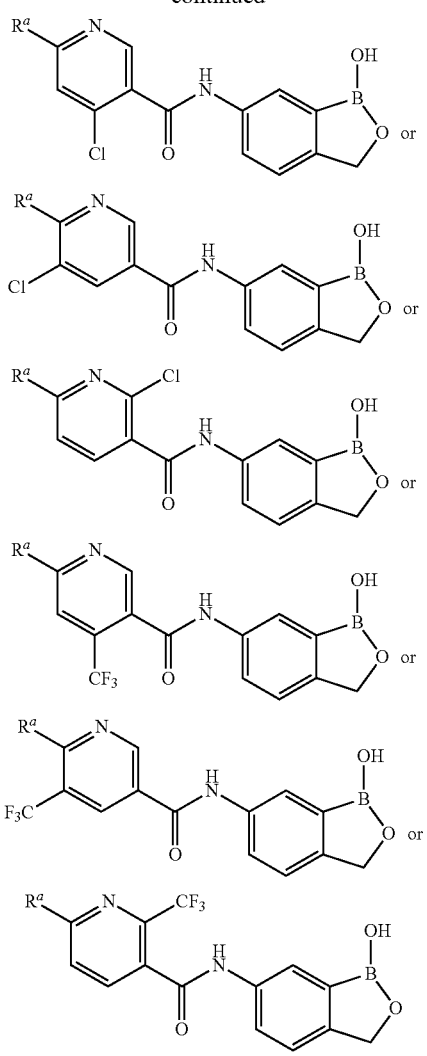

wherein $R^a$ is as described herein.

In an exemplary embodiment, the invention provides a compound, or a salt thereof, having a structure according to the following formula:

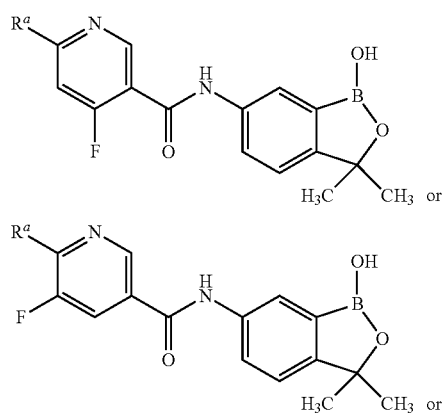

-continued

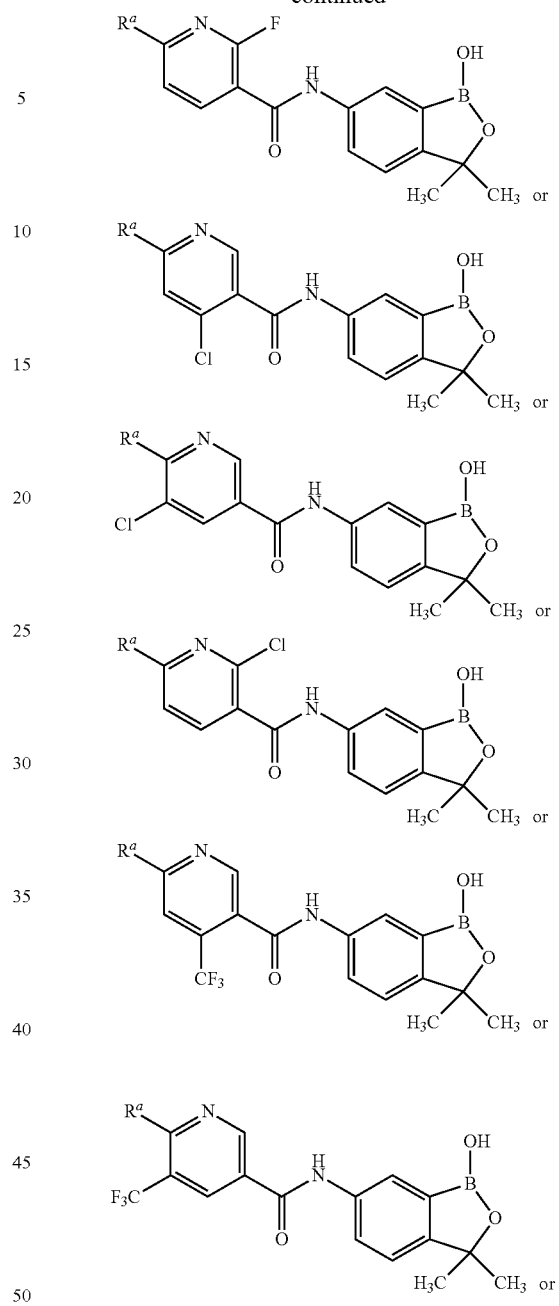

wherein $R^a$ is as described herein.

In an exemplary embodiment, the invention provides a compound, or a salt thereof, having a structure according to the following formula:

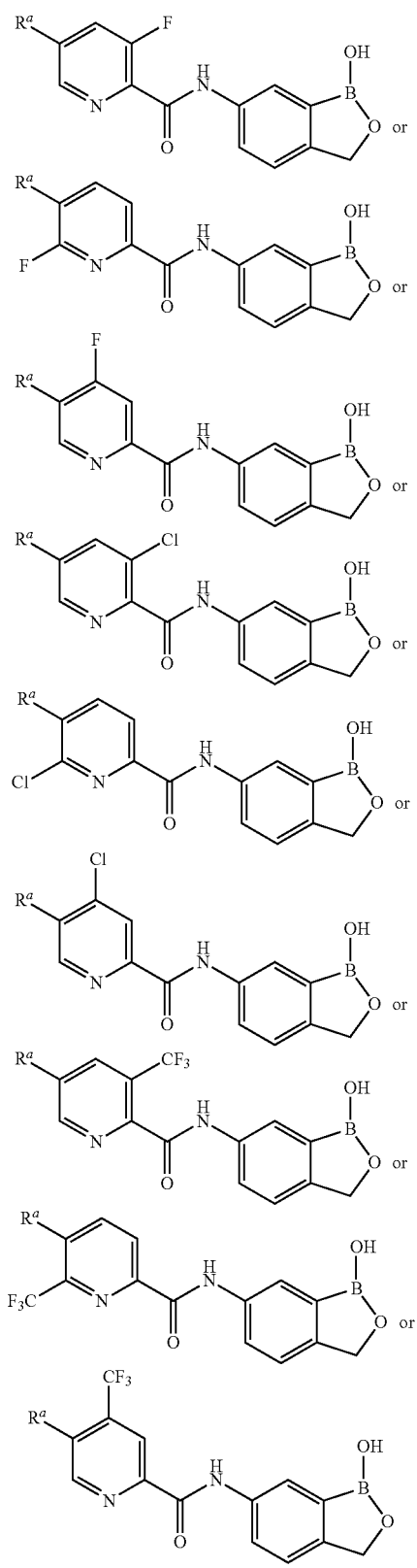
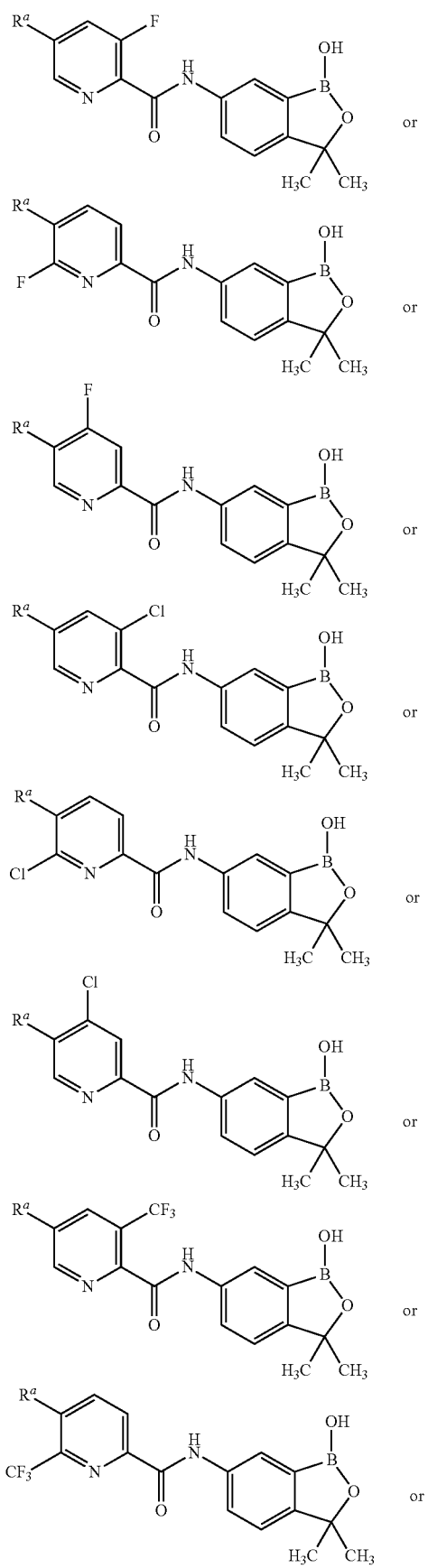
wherein R$^a$ is as described herein.
In an exemplary embodiment, the invention provides a compound, or a salt thereof, having a structure according to the following formula:

-continued

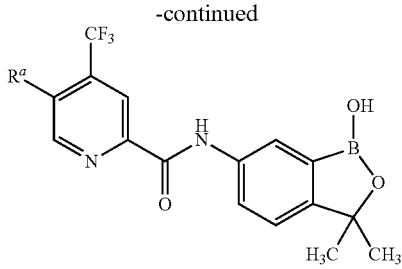

wherein $R^a$ is as described herein.

In an exemplary embodiment, a compound of the invention essentially does not inhibit a cytochrome P450 enzyme. In an exemplary embodiment, a compound of the invention does not inhibit a cytochrome P450 enzyme. In an exemplary embodiment, the cytochrome P450 enzyme is selected from CP1 A2, 2C9, 2D6 and 3A4. In an exemplary embodiment, the cytochrome P450 enzyme is CYP2C19.

In an exemplary embodiment, a compound of the invention is essentially not a substrate for the P-gp transporter. In an exemplary embodiment, a compound of the invention is not a substrate for the P-gp transporter.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

III.b) Combinations Comprising Additional Therapeutic Agents

The compounds of the invention may also be used in combination with additional therapeutic agents. The invention thus provides, in a further aspect, a combination comprising a compound described herein or a pharmaceutically acceptable salt thereof together with at least one additional therapeutic agent. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom.

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the animal (such as a human) and will be ultimately at the discretion of the attendant physician or veterinarian. In an exemplary embodiment, the additional therapeutic agent is berenil. In an exemplary embodiment, the additional therapeutic agent is diminazene. In an exemplary embodiment, the additional therapeutic agent is an antiprotozoa. In an exemplary embodiment, the additional therapeutic agent is selected from the group consisting of benznidazole, buparvaquone, carbarsone, clioquinol, disulfiram, eflornithine, emetine, etofamide, furazolidone, meglumine antimoniate, melarsoprol, metronidazole, miltefosine, nifurtimox, nimorazole, nitazoxanide, omidazole, paromomycin sulfate, pentamidine, pyrimethamine, secnidazole and tinidazole. In an exemplary embodiment, the additional therapeutic agent is pentamidine. In an exemplary embodiment, the additional therapeutic agent is suramin. In an exemplary embodiment, the additional therapeutic agent is eflornithine. In an exemplary embodiment, the additional therapeutic agent is melarsoprol. In an exemplary embodiment, the additional therapeutic agent is nifurtimox. In an exemplary embodiment, the additional therapeutic agent contains a 5-nitrofuran moiety. In an exemplary embodiment, the additional therapeutic agent contains a 5-nitroimidazolyl moiety. In an exemplary embodiment, the additional therapeutic agent is fexinidazole. In an exemplary embodiment, the additional therapeutic agent is an antiparasitic. In an exemplary embodiment, the additional therapeutic agent is selected from the group consisting of amitraz, avermectin, carbadox, diethylcarbamazine, dimetridazole, diminazene, ivermectin, macrofilaricide, malathion, mitaban, organophosphate, oxamniquine, permethrin, praziquantel, pyrantel pamoate, selamectin, sodium stibogluconate and thiabendazole. In an exemplary embodiment, the additional therapeutic agent is selected from the group consisting of antimony, meglumine antimoniate, sodium stibogluconate, amphotericin, miltefosine and paromomycin.

The compounds of the invention, or pharmaceutical formulations thereof may also be used in combination with other therapeutic agents, for example immune therapies [e.g. interferon, such as interferon alfa-2a (ROFERON®-A; Hoffmann-La Roche), interferon alpha-2b (INTRON®-A; Schering-Plough), interferon alfacon-1 (INFERGEN®; Intermune), peginterferon alpha-2b (PEGINTRON™; Schering-Plough) or peginterferon alpha-2a (PEGASYS®; Hoffmann-La Roche)], therapeutic vaccines, antifibrotic agents, anti-inflammatory agents [such as corticosteroids or NSAIDs], bronchodilators [such as beta-2 adrenergic agonists and xanthines (e.g. theophylline)], mucolytic agents, anti-muscarinics, anti-leukotrienes, inhibitors of cell adhesion [e.g. ICAM antagonists], anti-oxidants [e.g. N-acetylcysteine], cytokine agonists, cytokine antagonists, lung surfactants and/or antimicrobial. The compositions according to the invention may also be used in combination with gene replacement therapy.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the animal (such as a human) ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

It is to be understood that the invention covers all combinations of aspects and/or embodiments, as well as suitable, convenient and preferred groups described herein.

III.c) Preparation of Boron-Containing Compounds

Compounds of use in the invention can be prepared using commercially available starting materials, known intermediates, or by using the synthetic methods described herein, or published in references described and incorporated by reference herein, such as PCT Pub. No. WO2008157726 and U.S. Pat. Pubs. US20060234981, US20070155699 and US20070293457.

In one embodiment, the compound of the invention can be synthesized according to the following scheme:

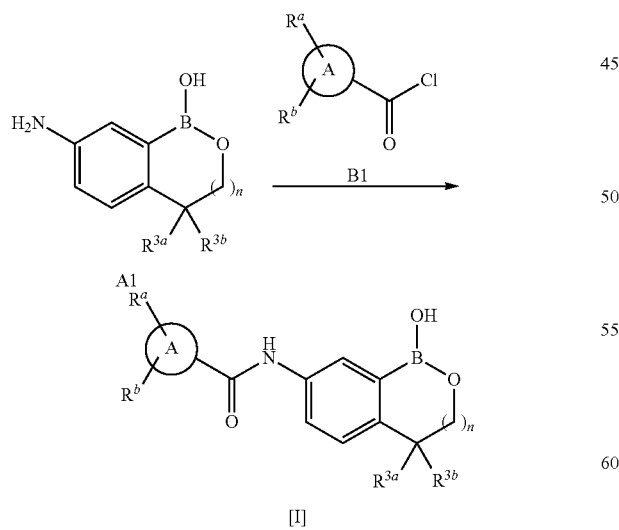

wherein A1 is known in references, such as WO2010045503, WO2011019616, WO2011019618, and WO2011116348. B1 can be purchased commerically or prepared by methods known in the art. An example of a synthesis of B1 involves reacting 4-fluoro-2-chlorobenzoic acid, or an ester thereof, with pyrazole to form a compound such as 2-chloro-4-(1H-pyrazol-1-yl)benzoic acid or an ester thereof which is hydrolyzed to the corresponding acid—compound C utilized in the synthesis Compound 1 in the Examples. Compound [I] is prepared in the same way as or a similar manner to what is described in the references above or other literature, such as ACS Med. Chem. Lett. 2010, 1, 165 and Future Med. Chem. 2011, 3(10), 1259. Compounds described herein can be converted into hydrates and solvates by methods similar to those described herein.

In one embodiment, the compound of the invention can be synthesized according to the following scheme:

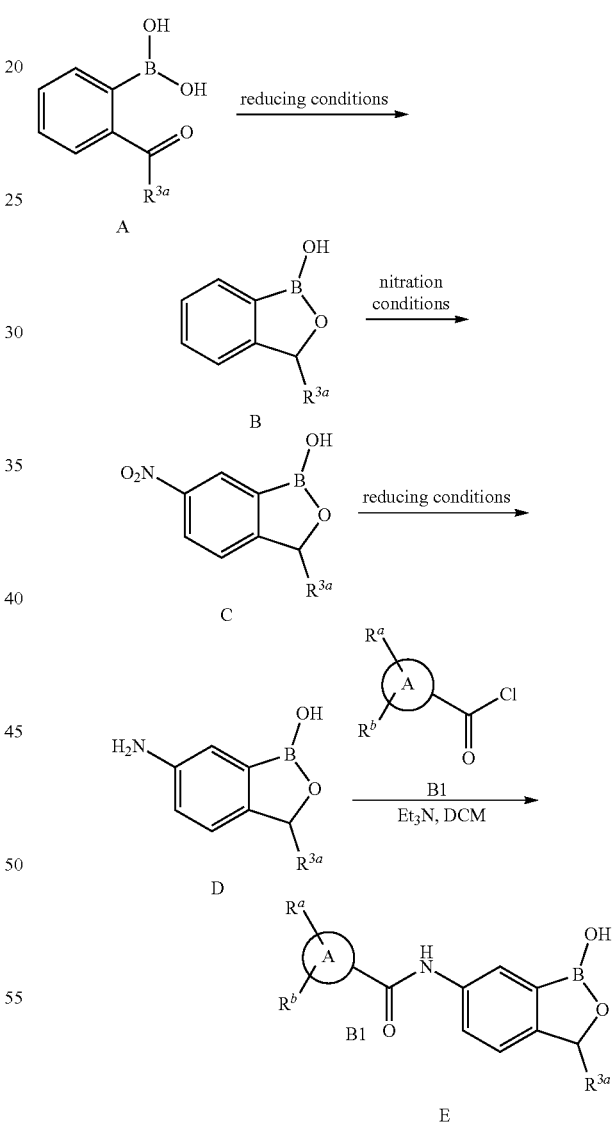

wherein A is commercially available from, for example, Sigma-Aldrich. A can be converted to B through subjecting it to reducing conditions, such as those involving sodium borohydride. B can be converted to C through subjecting it to nitration conditions, such as those involving fuming nitric acid. C can be converted to D through subjecting it to reducing conditions, such as those involving catalytic hydrogenation. D can be converted to E through subjecting it to acid chloride addition conditions.

In one embodiment, the compound of the invention can be synthesized according to the following scheme:

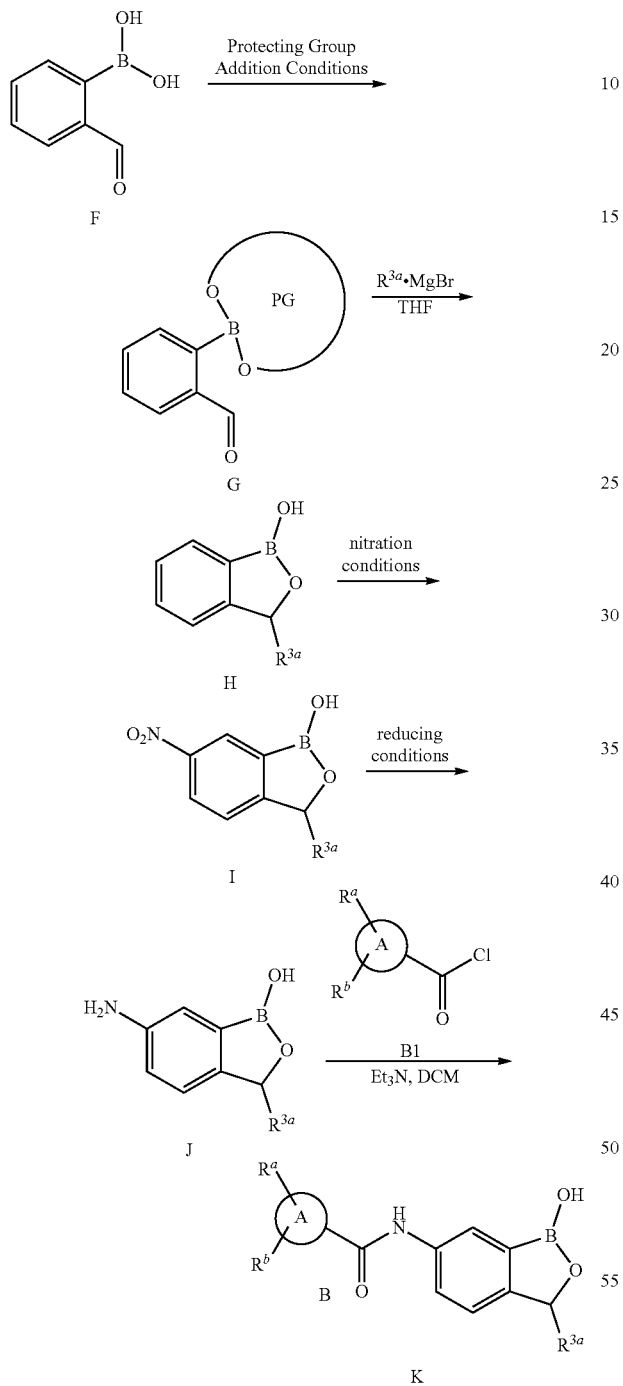

converted to J through subjecting it to reducing conditions, such as those involving catalytic hydrogenation. J can be converted to K through subjecting it to acid chloride addition conditions.

In one embodiment, the compound of the invention can be synthesized according to the following scheme:

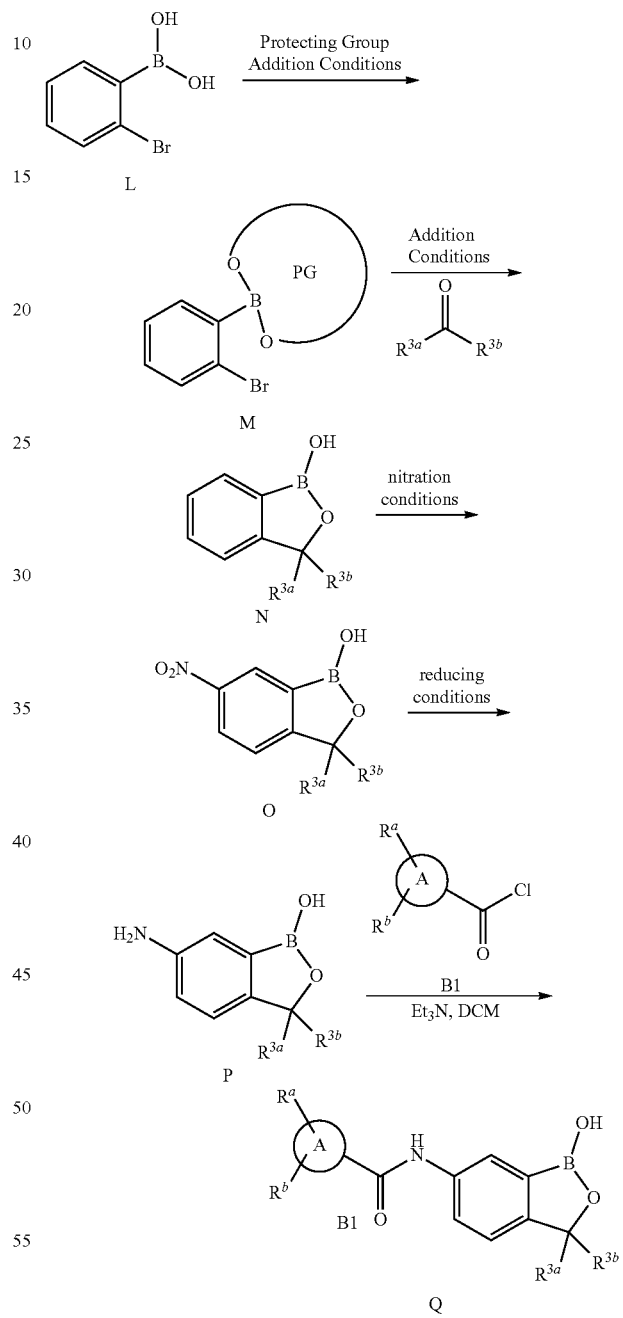

wherein F is commercially available from, for example, Sigma-Aldrich. F can be converted to G through subjecting it to protecting group addition conditions, such as those involving N-butyldiethanolamine. G can be converted to H through subjecting it to Grignard addition conditions. H can be converted to I through subjecting it to nitration conditions, such as those involving fuming nitric acid. I can be wherein L is commercially available from, for example, Sigma-Aldrich. L can be converted to M through subjecting it to protecting group addition conditions, such as those involving N-butyldiethanolamine. M can be converted to N through subjecting it to addition conditions, such as those involving an organolithium agent such as n-butyl lithium. N can be converted to O through subjecting it to nitration conditions, such as those involving fuming nitric acid. O can be converted to P through subjecting it to reducing conditions, such as those involving catalytic hydrogenation. P can be converted to Q through subjecting it to acid chloride addition conditions.

Compounds described herein can be converted into hydrates and solvates by methods similar to those described herein.

IV. Methods of Inhibiting Microorganism Growth or Killing Microorganisms

The compounds of the invention exhibit potency against microorganisms, such as protozoa, and therefore have the potential to kill and/or inhibit the growth of microorganisms.

In a further aspect, the invention provides a method of killing and/or inhibiting the growth of a microorganism, said method comprising: contacting said microorganism with an effective amount of a compound of the invention, thereby killing and/or inhibiting the growth of the microorganism. In an exemplary embodiment, the microorganism is a protozoa. In an exemplary embodiment, the microorganism is a kinetoplastid. In another exemplary embodiment, the protozoa is a *Trypanosoma*. In an exemplary embodiment, the *Trypanosoma* is selected from the group consisting of *T. avium, T. boissoni, T. brucei, T. carassii, T. cruzi, T. congolense, T. equinum, T. equiperdum, T. evansi, T. hosei, T. levisi, T. melophagium, T. parroti, T. percae, T. rangeli, T. rotatorium, T. rugosae, T. sergenti, T. simiae, T. sinipercae, T. suis, T. theileri, T. triglae* and *T. vivax*. In another exemplary embodiment, the protozoa is a *Trypanosoma brucei*. In another exemplary embodiment, the protozoa is *Trypanosoma brucei brucei*. In another exemplary embodiment, the protozoa is *Trypanosoma brucei rhodesiense*. In another exemplary embodiment, the protozoa is *Trypanosoma brucei gambiense*. In another exemplary embodiment, the protozoa is *Trypanosoma cruzi*. In another exemplary embodiment, the protozoa is *Trypanosoma congolense*. In another exemplary embodiment, the protozoa is a member of the genus *Leishmania*. In another exemplary embodiment, the protozoa is a member of *Leishmania Viannia*. In an exemplary embodiment, the protozoa is selected from the group consisting of *L. donovani. L. infantum, L. chagasi; L. mexicana. L. amazonensis, L. venezuelensis, L. tropica. L. major. L. aethiopica, L. (V.) braziliensis. L. (V.) guyanensis. L. (V.) panamensis*, and *L. (V.) peruviana*. In an exemplary embodiment, the protozoa is *L. donovani*. In an exemplary embodiment, the protozoa is *L. infantum*. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another aspect, the microorganism is inside, or on the surface of an animal. In an exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism is killed or its growth is inhibited through oral administration of the compound of the invention. In an exemplary embodiment, the microorganism is killed or its growth is inhibited through intravenous administration of the compound of the invention. In an exemplary embodiment, the microorganism is killed or its growth is inhibited through topical administration of the compound of the invention. In an exemplary embodiment, the microorganism is killed or its growth is inhibited through intraperitoneal administration of the compound of the invention. In an exemplary embodiment, the compound is administered in a topically effective amount. In an exemplary embodiment, the pharmaceutical formulation is administered in an orally effective amount.

V. Methods of Treating and/or Preventing Disease

The compounds of the invention exhibit potency against microorganisms, such as protozoa, and therefore have the potential to achieve therapeutic efficacy in the animals described herein.

In another aspect, the invention provides a method of treating and/or preventing a disease. The method includes administering to the animal a therapeutically effective amount of the compound of the invention, sufficient to treat and/or prevent the disease. In an exemplary embodiment, the compound of the invention can be used in human or veterinary medical therapy, particularly in the treatment or prophylaxis of protozoa-associated disease. In an exemplary embodiment, the compound of the invention can be used in human or veterinary medical therapy, particularly in the treatment or prophylaxis of kinetoplastid-associated disease. In an exemplary embodiment, the disease is associated with a *Trypanosoma*. In an exemplary embodiment, the *Trypanosoma* is selected from the group consisting of *T. avium, T. boissoni, T. brucei, T. carassii, T. cruzi, T. congolense, T. equinum, T. equiperdum, T. evansi, T. hosei, T. levisi, T. melophagium, T. parroti, T. percae, T. rangeli, T. rotatorium, T. rugosae, T. sergenti, T. simiae, T. sinipercae, T. suis, T. theileri, T. triglae* and *T. vivax*. In an exemplary embodiment, the disease is associated with a *Trypanosoma brucei*. In an exemplary embodiment, the disease is associated with a member selected from the group consisting of *Trypanosoma brucei brucei. Trypanosoma brucei rhodesiense* and *Trypanosoma brucei gambiense*. In an exemplary embodiment, the disease is associated with *Trypanosoma brucei rhodesiense*. In an exemplary embodiment, the disease is associated with *Trypanosoma brucei gambiense*. In an exemplary embodiment, the disease is associated with *Trypanosoma cruzi*. In an exemplary embodiment, the disease is associated with *Trypanosoma congolense*. In an exemplary embodiment, the disease is a trypanosomiasis. In an exemplary embodiment, the disease is a human trypanosomiasis. In an exemplary embodiment, the disease is an animal trypanosomiasis. In an exemplary embodiment, the disease is African animal trypanosomiasis, or AAT. In an exemplary embodiment, the disease is selected from the group consisting of nagana, surra, mal de caderas, murrina de caderas, dourine, cachexial fevers, Gambian horse sickness, baleri, kaodzera, tahaga, galziekte or galzietzke and peste-boba. In an exemplary embodiment, the disease is selected from the group consisting of Chagas disease (or Human American trypanosomiasis), nagana, surra, Covering sickness (or dourine) and sleeping sickness (or African sleeping sickness or Human African trypanosomiasis). In an exemplary embodiment, the disease is Chagas disease. In an exemplary embodiment, the disease is sleeping sickness (or African sleeping sickness). In an exemplary embodiment, the disease is acute phase sleeping sickness. In an exemplary embodiment, the disease is chronic phase sleeping sickness. In an exemplary embodiment, the disease is an acute phase of a trypanosomiasis. In an exemplary embodiment, the disease is a chronic phase of a trypanosomiasis. In an exemplary embodiment, the disease is the non-CNS form of a trypanosomiasis. In an exemplary embodiment, the disease is the CNS form of a trypanosomiasis. In an exemplary embodiment, the disease is the non-CNS form of sleeping sickness. In an exemplary embodiment, the disease is the CNS form of sleeping sickness. In an exemplary embodiment, the disease is early stage Human African trypanosomiasis. In an exemplary embodiment, the disease is late stage Human African trypanosomiasis. In another exemplary embodiment, the disease is associated with a member of the genus *Leishmania*. In another exemplary embodiment, the disease is associated with a member of *Leishmania Viannia*. In an exemplary embodiment, the disease is associated with a member selected from the group consisting of *L. donovani. L. infantum, L. chagasi; L. mexicana. L. amazonensis, L. venezuelensis, L. tropica. L. major. L. aethiopica, L. (V.) braziliensis. L. (V.) guyanensis. L. (V.) panamensis*, and *L. (V.) peruviana*. In an exemplary embodiment, the disease is associated with *L. donovani*. In an exemplary embodiment, the disease is associated with *L. infantum*. In an exemplary embodiment, the disease is leishmaniasis. In an exemplary embodiment, the disease is visceral leishmaniasis. In an exemplary embodiment, the disease is cutaneous leishmaniasis. In an exemplary embodiment, the disease is diffuse cutaneous leishmaniasis and/or mucocutaneous leishmaniasis. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a mouse. In another exemplary embodiment, the animal is selected from the group consisting of a human, cattle, goat, pig, sheep, horse, cow, bull, dog, guinea pig, gerbil, rabbit, cat, chicken and turkey. In another exemplary embodiment, the animal is a human. In another exemplary embodiment, the animal is cattle. In another exemplary embodiment, the animal is a cow. In another exemplary embodiment, the animal is a bull.

In an exemplary embodiment, the disease is treated through oral administration of the compound of the invention. In an exemplary embodiment, the disease is treated through intravenous administration of the compound of the invention. In an exemplary embodiment, the disease is treated through topical administration of the compound of the invention. In an exemplary embodiment, the disease is treated through intraperitoneal administration of the compound of the invention. In an exemplary embodiment, the compound is administered in a topically effective amount. In an exemplary embodiment, the pharmaceutical formulation is administered in an orally effective amount.

In an exemplary embodiment, the disease is associated with an infection by a microorganism described herein. In an exemplary embodiment, the disease is associated with an infection by a protozoa described herein.

VI. Pharmaceutical Formulations

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another aspect, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered intramuscularly. In an exemplary embodiment, the pharmaceutical formulation is administered subcutaneously. In an exemplary embodiment, the pharmaceutical formulation is administered in an orally effective dose.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also be added as a food or drink supplement for humans.

Dosage levels of the order of from about 1 mg to about 250 mg per kilogram of body weight per day and more preferably from about 5 mg to about 150 mg per kilogram of body weight per day, and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 5000 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular animal (such as a human) will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 7000 mg of a compound of the invention. In an exemplary embodiment, the unit dosage form contains from about 1 mg to about 5000 mg of an active ingredient. In an exemplary embodiment, the unit dosage form contains from about 100 mg to about 2000 mg of a compound of the invention. In an exemplary embodiment, the unit dosage form contains from about 200 mg to about 1000 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention.

Preferred compounds of the invention will have desirable pharmacological properties that include, but are not limited to, bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the animal (such as a human) and will ultimately be at the discretion of the attendant physician or clinician.

VI. a) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat. B*677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosages for use in humans or animals. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the human's condition. (See, e.g. Fingl et al., 1975, in "The Pharmacological Basis of Therapeutics", Ch. 1, p. 1).

VI. b) Administration

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of protozoa cell growth. Such information can be used to more accurately determine useful doses in humans or animals.

In general, the compounds prepared by the methods, and from the intermediates, described herein will be administered in a therapeutically effective amount by any of the accepted modes of administration for agents that serve similar utilities. It will be understood, however, that the specific dose level for any particular animal (such as a human) will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain protozoa cell growth inhibitory effects. Usual animal (such as a human) dosages for systemic administration range from 0.1 to 1000 mg/day, preferably, 1-500 mg/day, more preferably 10-200 mg/day, even more preferably 100-200 mg/day. Stated in terms of animal (such as a human) body surface areas, usual dosages range from 50-91 mg/m²/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

Exemplary embodiments are summarized herein below.

In an exemplary embodiment, the invention provides a compound having a structure according to the following formula:

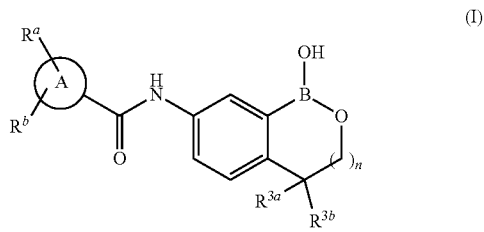

wherein A is phenyl or pyridinyl; $R^a$ is substituted or unsubstituted heteroaryl or substituted or unsubstituted heterocycloalkyl; $R^b$ is halogen or substituted or unsubstituted alkyl; n is 0 or 1; when n is 0, then $R^{3a}$ is H or unsubstituted $C_1$ or $C_2$ or $C_3$ or $C_4$ or $C_5$ or $C_6$ alkyl; $R^{3b}$ is H or unsubstituted $C_1$ or $C_2$ or $C_3$ or $C_4$ or $C_5$ or $C_6$ alkyl; with the proviso that $R^{3a}$ and $R^{3b}$, along with the atom to which they are attached, are optionally joined to form a 3 or 4 or 5 or 6 membered ring with the proviso that $R^{3a}$ and $R^{3b}$ cannot both be H; when n is 1, then $R^3$ is H and $R^{3b}$ is H; or a salt thereof.

In an exemplary embodiment, according to the above paragraph, the compound, or a salt thereof, wherein $R^a$ is substituted or unsubstituted morpholinyl or substituted or unsubstituted pyrazolyl or substituted or unsubstituted pyrrolopyridinyl or substituted or unsubstituted pyrrolidinyl or substituted or unsubstituted piperizinyl or substituted or unsubstituted pyridazinyl or substituted or unsubstituted piperidinyl or substituted or unsubstituted imidazolyl or substituted or unsubstituted azetidinyl or substituted or unsubstituted triazolyl.

In an exemplary embodiment, according to any of the above paragraphs, the compound, or a salt thereof, having a structure according to the following formula:

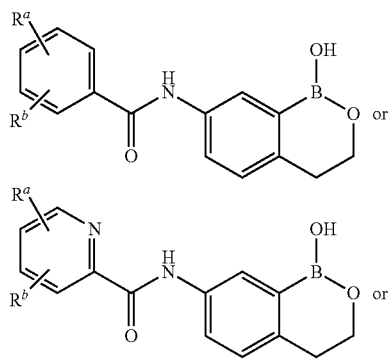

-continued

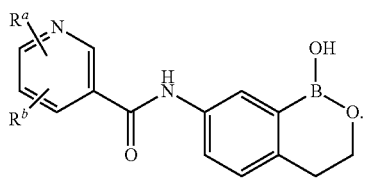

In an exemplary embodiment, according to any of the above paragraphs, the compound, or a salt thereof, having a structure according to the following formula:

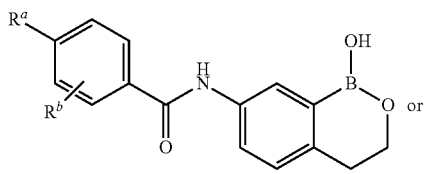

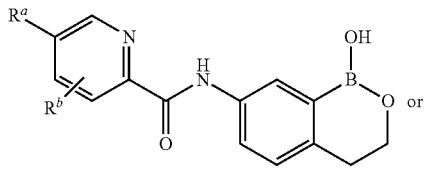

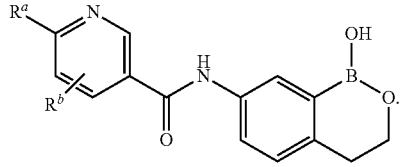

In an exemplary embodiment, according to any of the above paragraphs, the compound, or a salt thereof, having a structure according to the following formula:

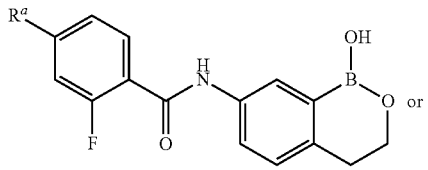

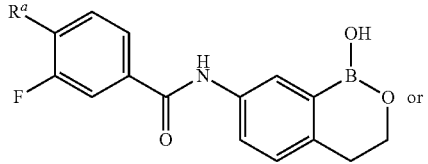

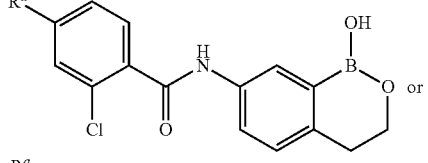

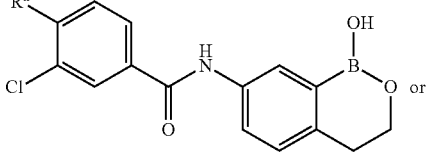

-continued

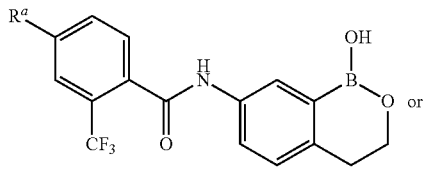

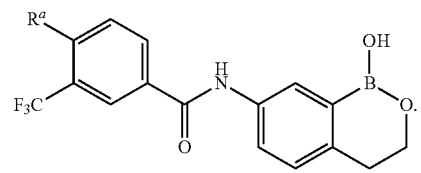

In an exemplary embodiment, according to any of the above paragraphs, the compound, or a salt thereof, having a structure according to the following formula:

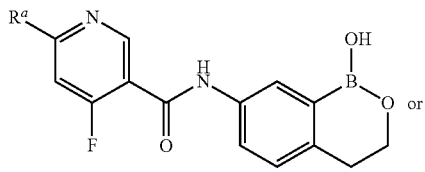

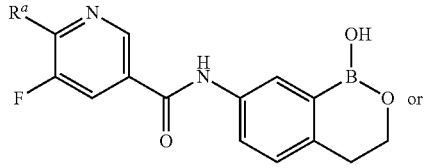

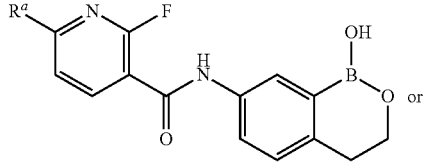

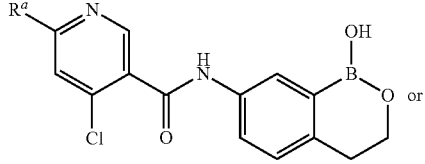

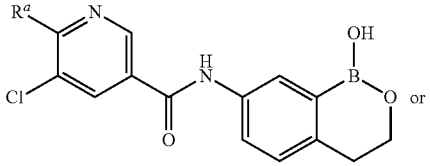

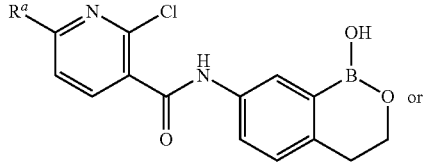

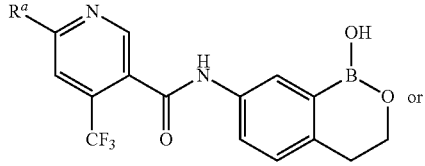

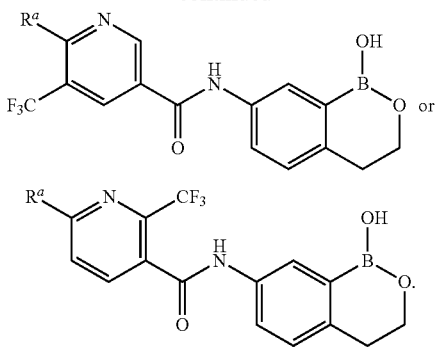
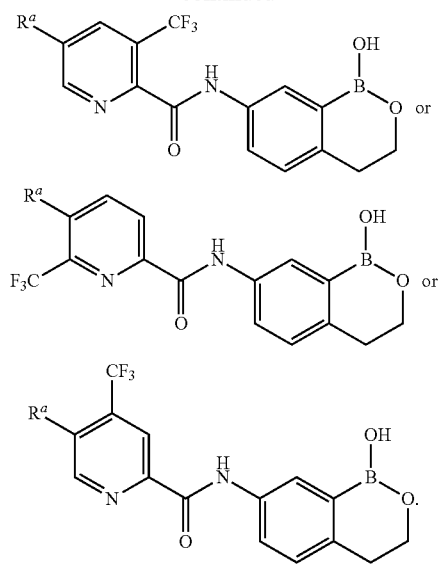
In an exemplary embodiment, according to any of the above paragraphs, the compound, or a salt thereof, having a structure according to the following formula:
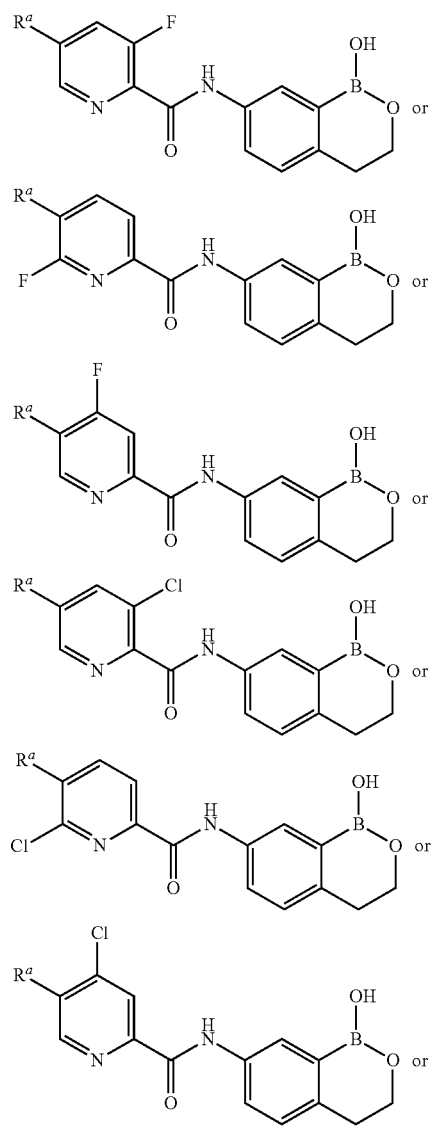
In an exemplary embodiment, according to any of the above paragraphs, the compound, or a salt thereof, having a structure according to the following formula:
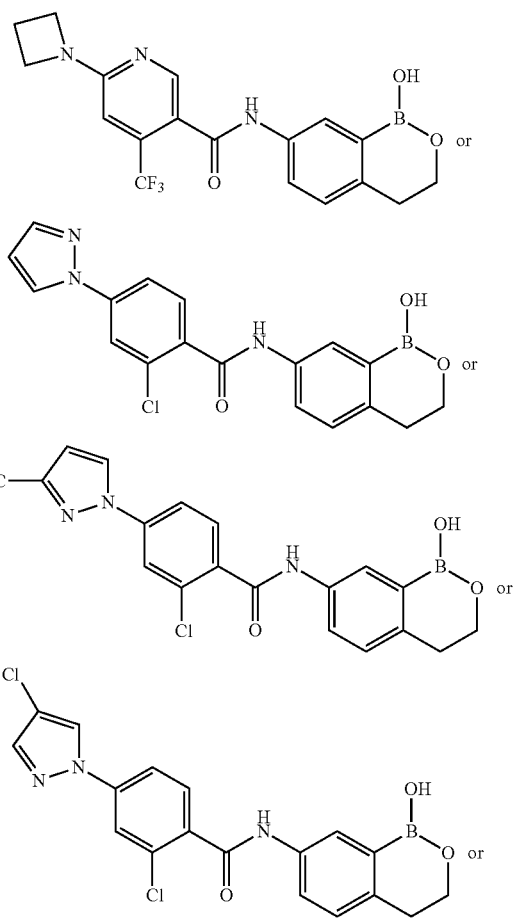

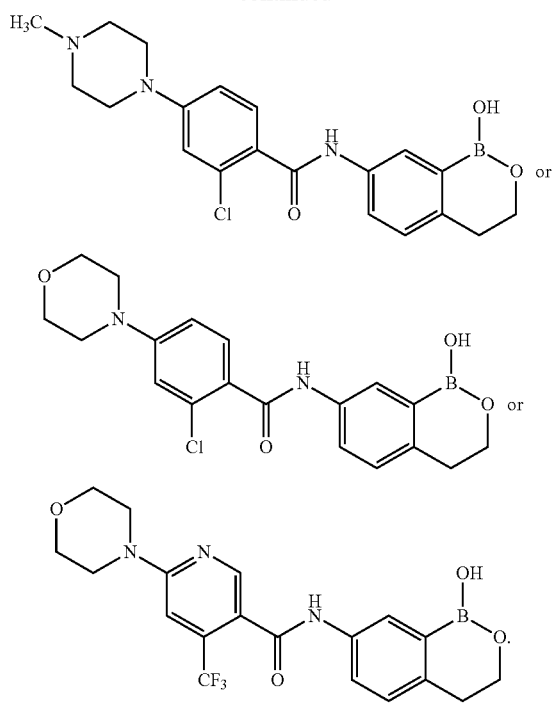

In an exemplary embodiment, according to any of the above paragraphs, the compound, or a salt thereof, having a structure according to the following formula:

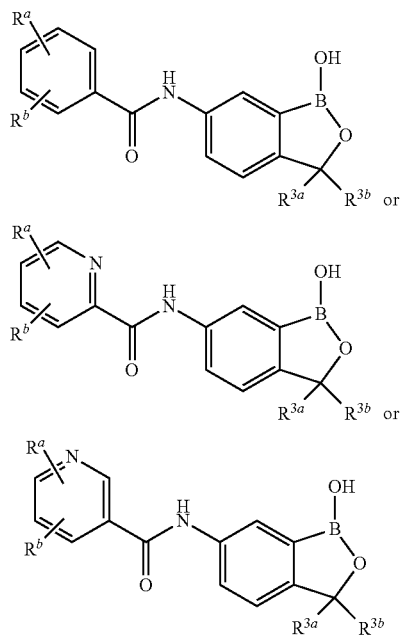

In an exemplary embodiment, according to any of the above paragraphs, the compound, or a salt thereof, having a structure according to the following formula:

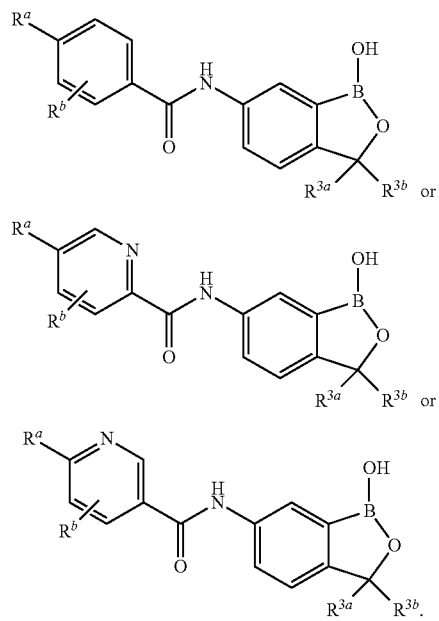

In an exemplary embodiment, according to any of the above paragraphs, the compound, or a salt thereof, having a structure according to the following formula:

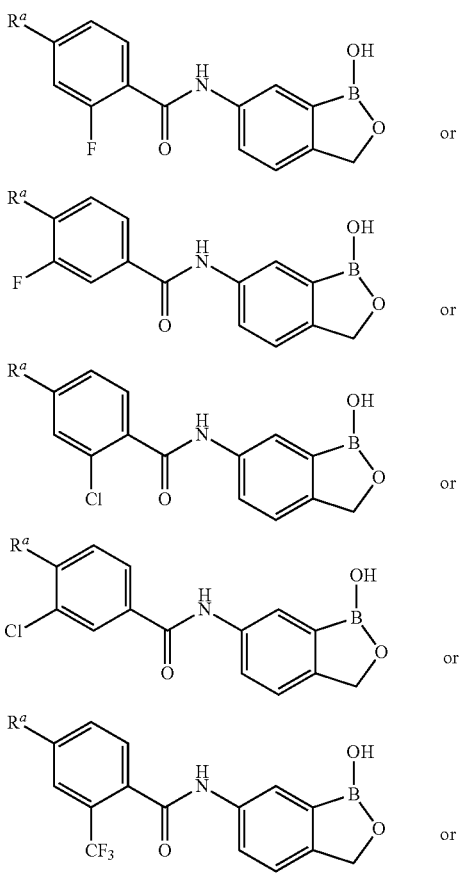

-continued

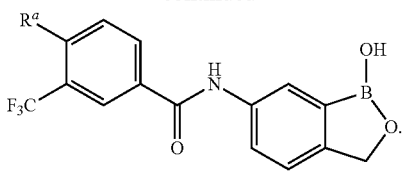

In an exemplary embodiment, according to any of the above paragraphs, the compound, or a salt thereof, having a structure according to the following formula:

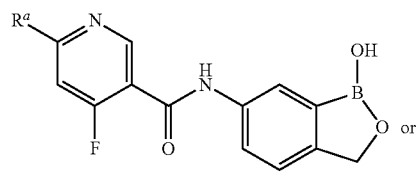 or

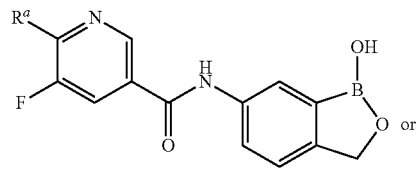 or

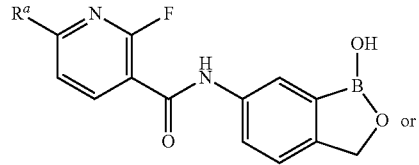 or

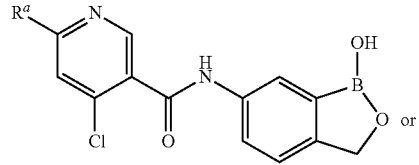 or

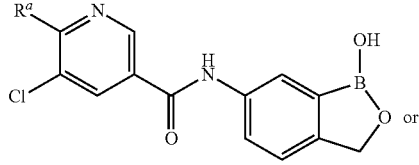 or

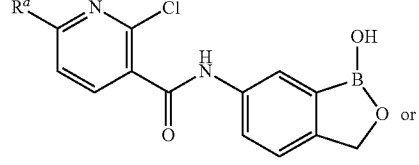 or

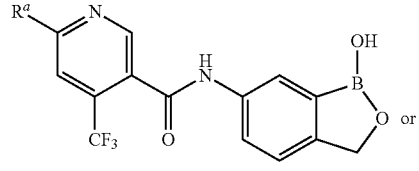 or

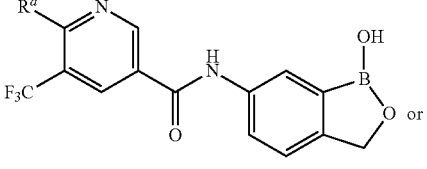 or

-continued

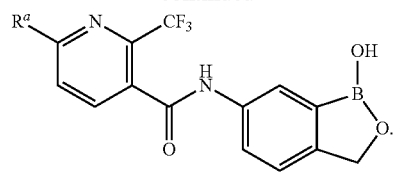

In an exemplary embodiment, according to any of the above paragraphs, the compound, or a salt thereof, having a structure according to the following formula:

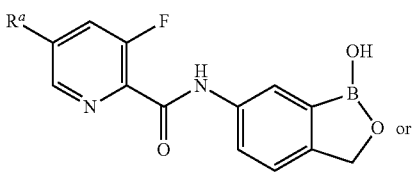 or

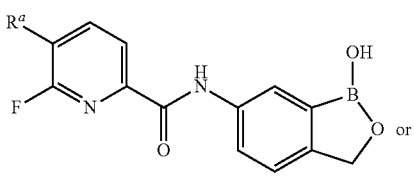 or

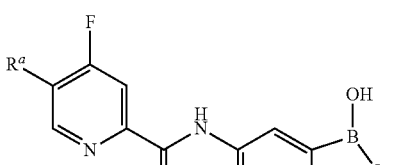 or

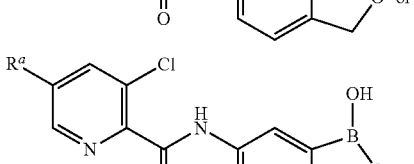 or

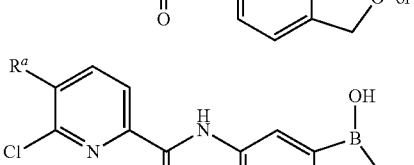 or

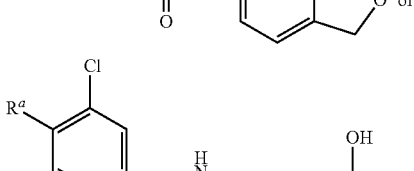 or

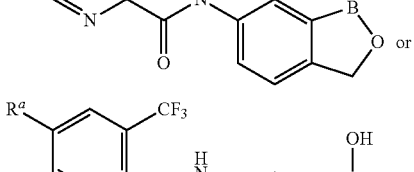 or

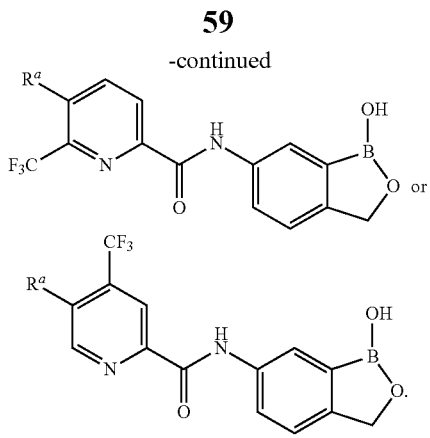

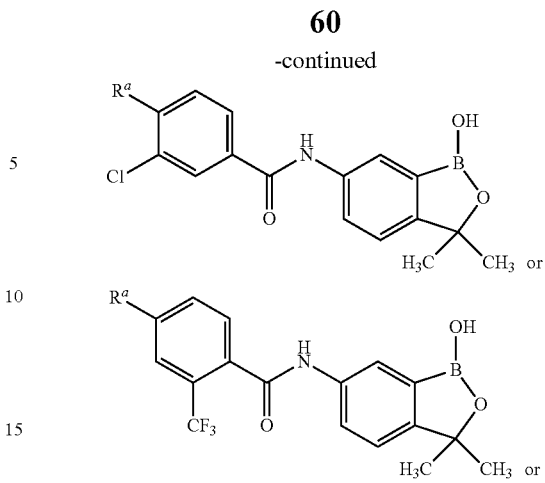

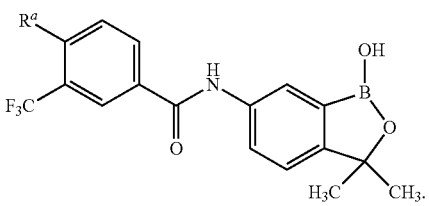

In an exemplary embodiment, according to any of the above paragraphs, the compound, or a salt thereof, which is:

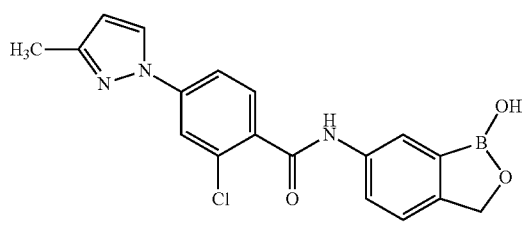

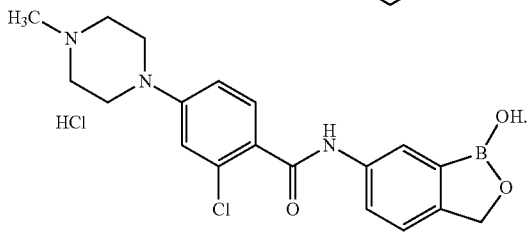

In an exemplary embodiment, according to any of the above paragraphs, the compound, or a salt thereof, having a structure according to the following formula:

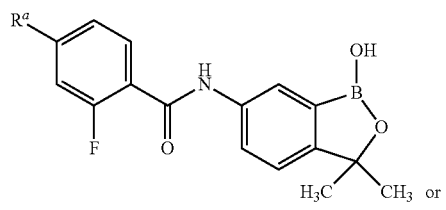

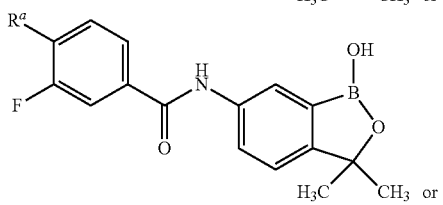

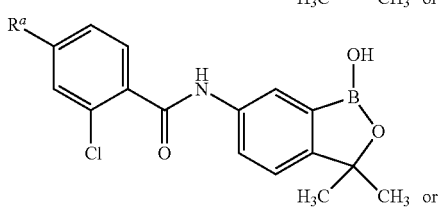

In an exemplary embodiment, according to any of the above paragraphs, the compound, or a salt thereof, having a structure according to the following formula:

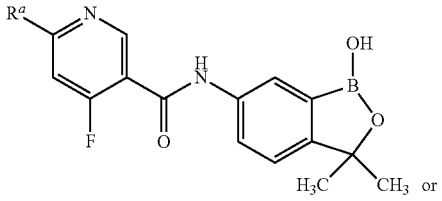

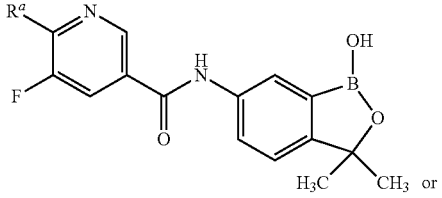

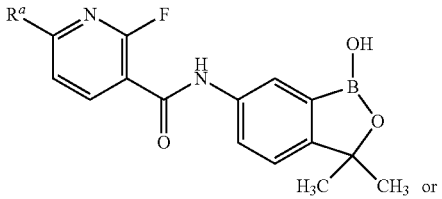

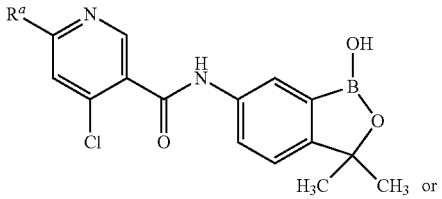

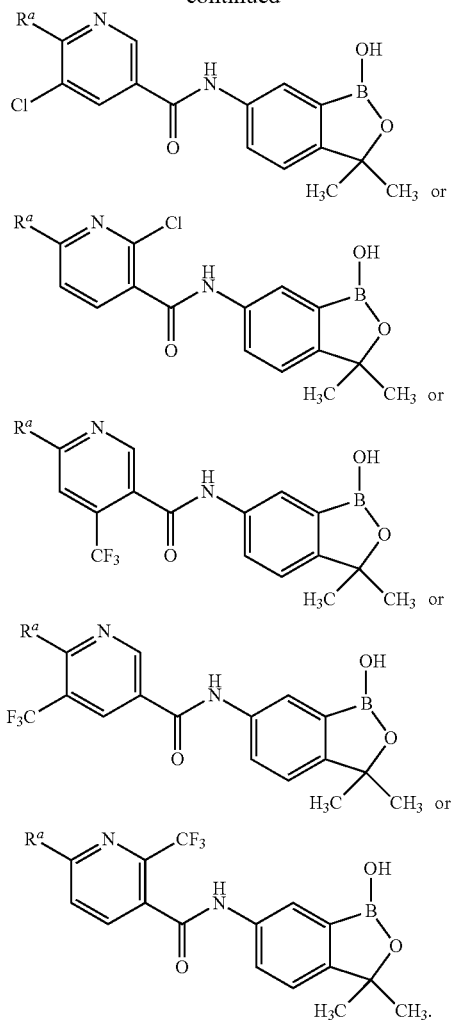
In an exemplary embodiment, according to any of the above paragraphs, the compound, or a salt thereof, having a structure according to the following formula:
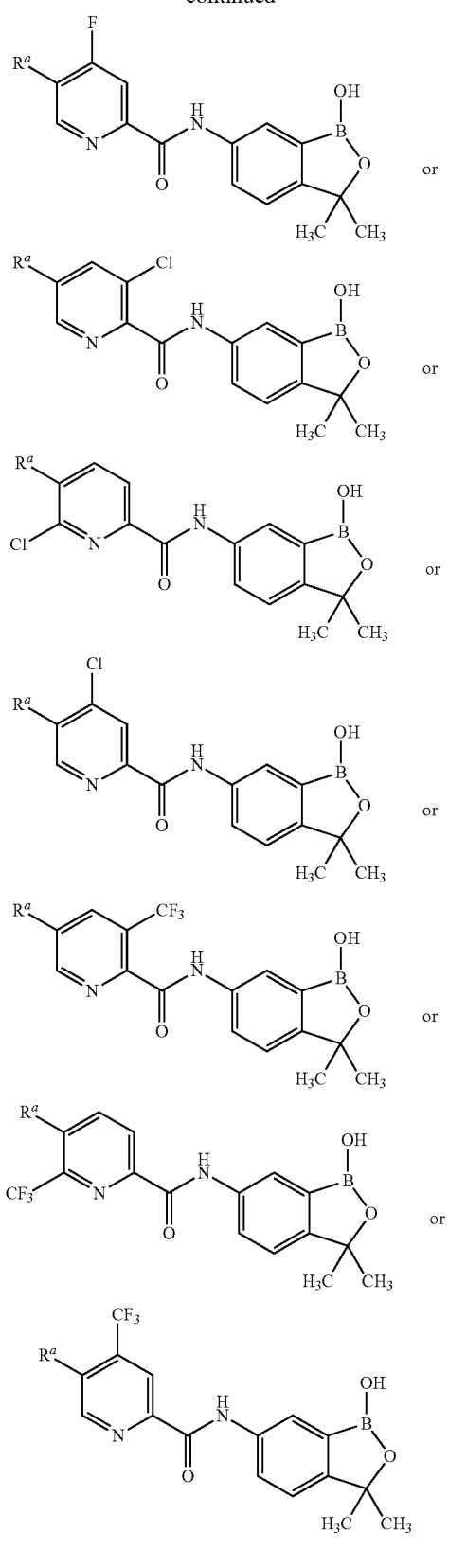
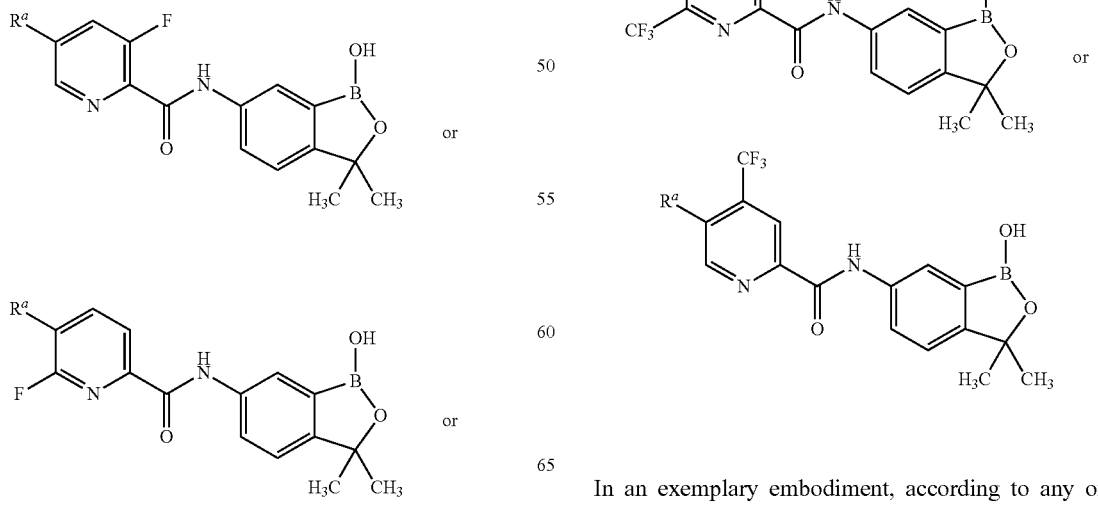
In an exemplary embodiment, according to any of the above paragraphs, the compound, or a salt thereof, which is:

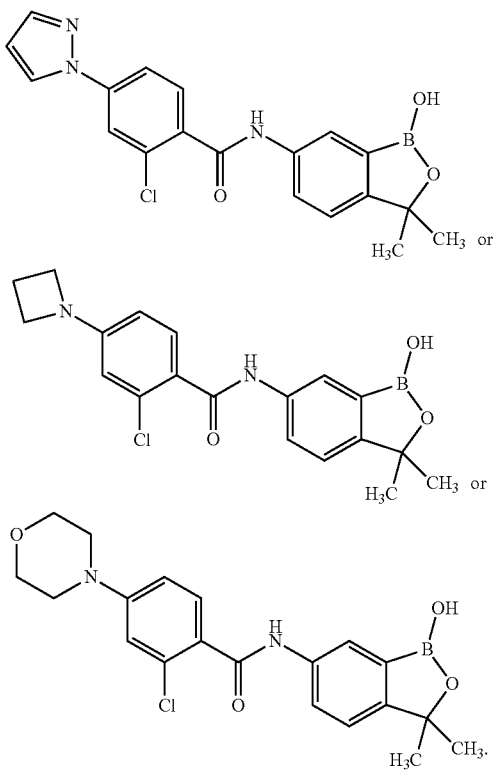

In an exemplary embodiment, the invention provides a combination comprising the compound according to any of the above paragraphs, together with at least one other therapeutically active agent.

In an exemplary embodiment, the invention provides a pharmaceutical formulation comprising: a) the compound according to any of the above paragraphs, or a salt thereof; and b) a pharmaceutically acceptable excipient.

In an exemplary embodiment, according to any of the above paragraphs, the pharmaceutical formulation is a unit dosage form.

In an exemplary embodiment, according to any of the above paragraphs, the salt of the compound according to any of the above paragraphs is a pharmaceutically acceptable salt.

In an exemplary embodiment, the invention provides a method of killing and/or preventing the growth of a protozoa, comprising: contacting the protozoa with a compound of the invention, thereby killing and/or preventing the growth of the protozoa.

In an exemplary embodiment, according to any of the above paragraphs, wherein an effective amount of the compound of the invention contacts the protozoa.

In an exemplary embodiment, according to any of the above paragraphs, the compound has a structure described herein.

In an exemplary embodiment, according to any of the above paragraphs, the protozoa is a member of the trypanosome genus.

In an exemplary embodiment, according to any of the above paragraphs, the protozoa is *Trypanosoma brucei*.

In an exemplary embodiment, according to any of the above paragraphs, the *Trypanosoma brucei* is selected from the group consisting of *Trypanosoma brucei brucei*, *Trypanosoma brucei gambiense* and *Trypanosoma brucei rhodesiense*.

In an exemplary embodiment, according to any of the above paragraphs, the protozoa is *Trypanosoma congolense*.

In an exemplary embodiment, the invention provides a method of treating and/or preventing a disease in an animal, comprising: administering to the animal a therapeutically effective amount of the compound of the invention, thereby treating and/or preventing the disease.

In an exemplary embodiment, according to any of the above paragraphs, the compound has a structure described herein.

In an exemplary embodiment, according to any of the above paragraphs, the disease is African animal trypanosomiasis.

In an exemplary embodiment, according to any of the above paragraphs, the animal is cattle.

In an exemplary embodiment, according to any of the above paragraphs, the animal is a cow.

In an exemplary embodiment, according to any of the above paragraphs, the animal is a bull.

In an exemplary embodiment, according to any of the above paragraphs, the invention is a use of a compound of the invention or a combination of the invention in the manufacture of a medicament for the treatment and/or prophylaxis of protozoal infection.

The invention is further illustrated by the Examples that follow. The Examples are not intended to define or limit the scope of the invention.

EXAMPLES

The following Examples illustrate the synthesis of representative compounds used in the invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the invention are possible in view of the teachings herein and, therefore, are within the scope of the invention.

All temperatures are given in degrees Centigrade. Room temperature means 20 to 25° C. Reagents were purchased from commercial sources or prepared following standard literature procedures. Unless otherwise noted, reactions were carried out under a positive pressure of nitrogen. Reaction vessels were sealed with either rubber septa or Teflon screw caps. Nitrogen was introduced through Tygon tubing, fitted with a large bore syringe needle. Concentration under vacuum refers to the removal of solvent on a Bilchi Rotary Evaporator.

Analytical HPLC was performed using a Supelco discovery $C_{18}$ 15 cm×4.6 mm/5 µm column coupled with an Agilent 1050 series VWD UV detector at 210 nm. Conditions: Solvent A: $H_2O$/1% acetonitrile/0.1% $HCO_2H$; Solvent B: methanol.

Proton magnetic resonance ($^1H$ NMR) spectra were recorded on a Varian INOVA NMR spectrometer [400 MHz ($^1H$) or 500 MHz ($^1H$)] or Varian 400-MR [400 MHz (1H)]. All spectra were determined in the solvents indicated. Although chemical shifts are reported in ppm downfield of tetramethylsilane, they are referenced to the residual proton peak of the respective solvent peak for $^1H$ NMR. Interproton coupling constants are reported in Hertz (Hz).

LCMS spectra were obtained using a ThermoFinnigan AQA MS ESI instrument utilizing a Phenomenex Aqua 5 micron $C_{18}$ 125 Å50×4.60 mm column. The spray setting for the MS probe was at 350 µL/min with a cone voltage at 25 mV and a probe temperature at 450° C. The spectra were recorded using ELS and UV (254 nm) detection. Alternatively, LCMS spectra were obtained using an Agilent 1200SL HPLC equipped with a 6130 mass spectrometer or Agilent 1200 series with a 6140 mass spectrometer operating with electrospray ionization.

Silica gel chromatography was carried out on either a Teledyne ISCO CombiFlash Companion or Companion Rf Flash Chromatography System with a variable flow rate from 5-100 mL/min. The columns used were Teledyne ISCO RediSep Disposable Flash Columns (4, 12, 40, 80, or 120 g prepacked silica gel), which were run with a maximum capacity of 1 g crude sample per 10 g silica gel. Samples were preloaded on Celite in Analogix Sample Loading Cartridges with frits (1/in, 1/out). The eluent was 0-100% EtOAc in heptane or 0-10% MeOH in $CH_2Cl_2$ as a linear gradient over the length of the run (14-20 minutes). Peaks were detected by variable wavelength UV absorption (200-360 nm). The resulting fractions were analyzed, combined as appropriate, and evaporated under reduced pressure to provide purified material.

Example 1

1. 2-Chloro-N-(1-hydroxy-3,3-dimethyl-1,3-Dihydro-benzo[c][1,2]oxaborol-6-yl-4-pyrazol-1-yl-benzamide

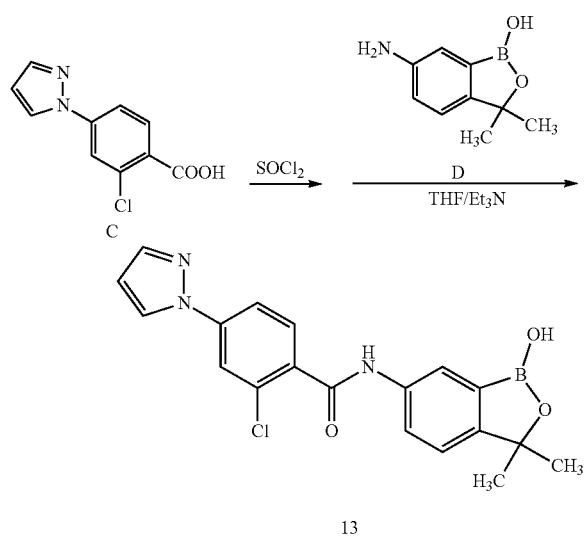

13

To a stirred solution of C (100 g, 0.45 mol) in $SOCl_2$ (200 mL) was added 0.5 mL of DMF, and the resulting mixture was heated at reflux for 3 hours. The reaction was then cooled to room temperature. The excess of $SOCl_2$ was removed by evaporation. The residue was diluted with THF (1.5 L) and added dropwise to a solution of D (79.7 g, 0.45 mol) and $Et_3N$ (136 g, 1.35 mol) in THF (4.5 L) at 0° C. After stirring at room temperature for 2 h, the mixture was poured into cold ice-water, and neutralized with 2 N aq. HCl acid. The aqueous solution was extracted twice with ethyl acetate. The combined organic phases were washed with water and brine, dried over $Na_2SO_4$, filtered, and concentrated in vacuo to give crude product 115 g. 110 g of crude product was dissolved in acetone (4 L), and slowly added to 5 L of distilled water, white solid precipitated from the mixture. The solid was filtered and dried under reduced pressure (oil pump) to give 105 g desired product as white solid. After one night of vacuum-dry at 40° C., the desired product was obtained as white powder (100.25 g, 58%).

LCMS (M/Z): 382 (M+H); $^1$H NMR (400 MHz, DMSO-d6) δ ppm 1.45 (s, 6H) 6.59-6.64 (m, 1H) 7.39 (d, J=8.2 Hz, 1H) 7.66-7.75 (m, 2H) 7.83 (d, J=1.6 Hz, 1H) 7.96 (dd, J=8.4, 2.1 Hz, 1H) 8.08 (dd, J=5.6, 1.9 Hz, 2H) 8.68 (d, J=2.6 Hz, 1H) 9.09 (s, 1H) 10.55 (s, 1H).

2. 2-Chloro-N-(1-hydroxy-1,3-dihydro-benzo[c][1,2]oxaborol-6-yl)-4-pyrrolidin-1-yl-benzamide

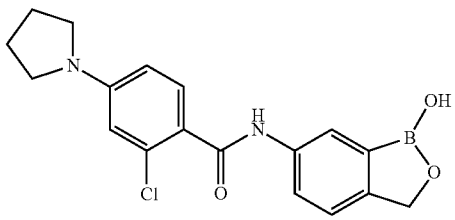 [SMILES: O=C(Nc1ccc2c(c1)B(O)OC2)c1ccc(N2CCCC2)cc1Cl]

The compound was prepared in a manner similar to AAT-13 replacing C with 2-chloro-4-(pyrrolidin-1-yl)benzoic acid and D with 6-aminobenzo[c][1,2]oxaborol-1(3H)-ol.

LCMS (M/Z): 357 (M+H); $^1$H NMR (400 MHz, DMSO-d6) δ ppm 1.88-2.00 (m, 4H) 3.20-3.26 (m, 4H) 4.91 (s, 2H) 6.49-6.53 (m, 1H) 6.53-6.55 (m, 1H) 7.31 (d, J=8.8 Hz, 1H) 7.38 (d, J=8.5 Hz, 1H) 7.67 (dd J=8.2, 1.8 Hz, 1H) 8.09 (s, 1H) 9.17 (s, 1H) 10.10 (s, 1H).

3. 2-Chloro-N-(1-hydroxy-1,3-dihydro-benzo[c][1,2]oxaborol-6-yl)-4-(3-methyl-pyrazol-1-yl)-benzamide

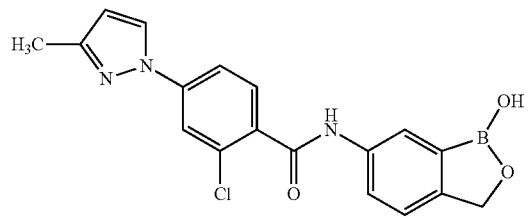 [SMILES: Cc1ccn(-c2ccc(C(=O)Nc3ccc4c(c3)B(O)OC4)c(Cl)c2)n1]

The compound was prepared in a manner similar to AAT-13 replacing C with 2-chloro-4-(3-methyl-1H-pyrazol-1-yl)benzoic acid and D with 6-aminobenzo[c][1,2]oxaborol-1(3H)-ol.

LCMS (M/Z): 368 (M+H); $^1$H NMR (400 MHz, DMSO-d6) δ ppm 2.29 (s, 3H) 4.97 (s, 2H) 6.41 (d, J=2.4 Hz, 1H) 7.39 (d, J=8.3 Hz, 1H) 7.72 (dd, J=8.2, 2.0 Hz, 2H) 7.90 (dd, J=8.4, 2.1 Hz, 1H) 8.01 (d, J=2.1 Hz, 1H) 8.17 (s, 1H) 8.54 (d, J=2.4 Hz, 1H) 9.25 (s, 1H) 10.55 (s, 1H).

4. 2-Chloro-4-(4-chloro-iyrazol-1-yl)-N-(1-hydroxy-1,3-dihydro-benzo[c][1,2]oxaborol-6-yl)-benzamide

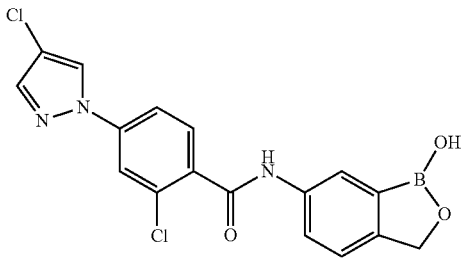 [SMILES: O=C(Nc1ccc2c(c1)B(O)OC2)c1ccc(-n2cc(Cl)cn2)cc1Cl]

The compound was prepared in a manner similar to AAT-13 replacing C with 2-chloro-4-(4-chloro-1H-pyrazol-1-yl)benzoic acid and D with 6-aminobenzo[c][1,2]oxaborol-1(3H)-ol.

LCMS (M/Z): 388 (M+H); $^1$H NMR (400 MHz, DMSO-d6) δ ppm 4.97 (s, 2H) 7.39 (d, J=8.3 Hz, 1H) 7.72 (dd, J=8.3, 2.0 Hz, 1H) 7.77 (d, J=8.4 Hz, 1H) 7.93 (dd, J=8.4, 2.2 Hz, 1H) 7.98 (s, 1H) 8.06 (d, J=2.1 Hz, 1H) 8.17 (d, J=1.7 Hz, 1H) 8.97 (s, 1H) 9.25 (s, 1H) 10.58 (s, 1H).

5. 2-Chloro-4-(3-chloro-pyrrolo[2,3-b]pyridin-1-yl)-N-(1-hydroxy-1,3-dihydro-benzo[c][1,2]oxaborol-6-yl)-benzamide

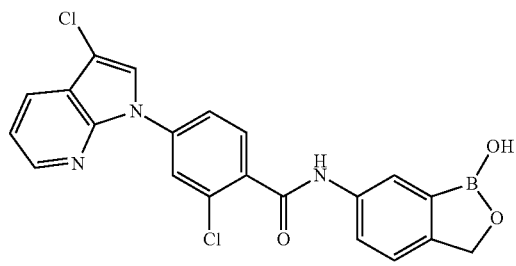 [SMILES: O=C(Nc1ccc2c(c1)B(O)OC2)c1ccc(-n2cc(Cl)c3cccnc32)cc1Cl]

The compound was prepared in a manner similar to AAT-13 replacing C with 2-chloro-4-(3-chloro-1H-pyrrolo[2,3-b]pyridin-1-yl)benzoic acid and D with 6-aminobenzo[c][1,2]oxaborol-1(3H)-ol.

LCMS (M/Z): 438 (M+H); $^1$H NMR (400 MHz, DMSO-d6) δ ppm 4.98 (s, 2H) 7.40 (dd, J=7.9, 4.6 Hz, 2H) 7.74 (dd, J=8.2, 2.0 Hz, 1H) 7.79 (d, J=8.3 Hz, 1H) 8.11 (td, J=8.0, 1.8 Hz, 2H) 8.19 (d, J=1.7 Hz, 1H) 8.29 (d, J=2.1 Hz, 1H) 8.42 (s, 1H) 8.50 (dd, J=4.7, 1.5 Hz, 1H) 9.26 (s, 1H) 10.62 (s, 1H).

6. 2-Chloro-N-(1-hydroxy-1,3-dihydrobenzo[c][1,2]oxaborol-6-yl)-4-(4-methylpiperazin-1-yl)benzamide hydrochloride

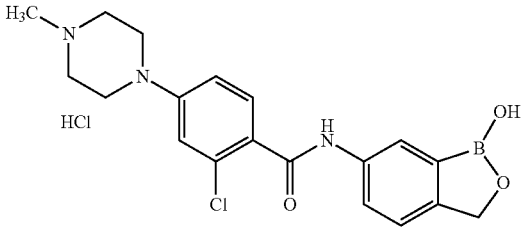 [SMILES: CN1CCN(c2ccc(C(=O)Nc3ccc4c(c3)B(O)OC4)c(Cl)c2)CC1 ; Cl]

The compound was prepared in a manner similar to AAT-13 replacing C with 2-chloro-4-(4-methylpiperazin-1-yl)benzoic acid and D with 6-aminobenzo[c][1,2]oxaborol-1(3H)-ol.

LCMS (M/Z): 386 (M+H); $^1$H NMR (400 MHz, DMSO-d6) δ10.86 (s, 1H), 10.33 (s, 1H), 9.24 (s, 1H), 8.15 (s, 1H), 7.71 (d, 1H, J=8.0 Hz), 7.50 (d, 1H, J=8.4 Hz), 7.37 (d, 1H, J=8.4 Hz), 7.15 (s, 1H), 7.06 (d, 1H, J=8.4 Hz), 4.97 (s, 1H), 4.00 (d, 2H, J=12.4 Hz), 3.49 (d, 2H, J=11.6 Hz), 3.23-3.12 (m, 4H), 2.82 (s, 3H).

7. 2-Chloro-N-(1-hydroxy-1,3-dihydro-benzo[c][1,2]oxaborol-6-yl)-4-morpholin-4-yl-benzamide

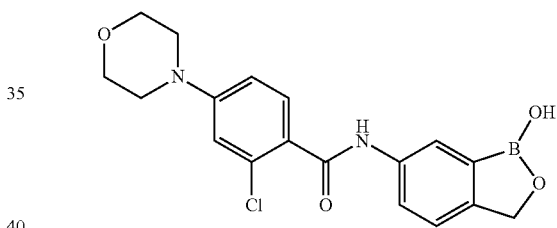

The compound was prepared in a manner similar to AAT-13 replacing C with 2-chloro-4-morpholinobenzoic acid and D with 6-aminobenzo[c][1,2]oxaborol-1(3H)-ol.

LCMS (M/Z): 373 (M+H); $^1$H NMR (400 MHz, DMSO-d6) δ ppm 3.14-3.21 (m, 4H) 3.66-3.73 (m, 4H) 4.92 (s, 2H) 6.95 (dd, J=8.6, 2.4 Hz, 1H) 7.00 (d, J=2.3 Hz, 1H) 7.32 (d, J=8.5 Hz, 1H) 7.41 (d, J=8.7 Hz, 1H) 7.66 (d, J=7.8 Hz, 1H) 8.10 (s, 1H) 9.18 (s, 1H) 10.24 (s, 1H).

8. 4-Azeidin-1-yl-2-chloro-N-(1-hydroxy-3,3-dimethyl-1,3-dihydro-benzo[c][1,2]oxaborol-6-yl)-benzamide

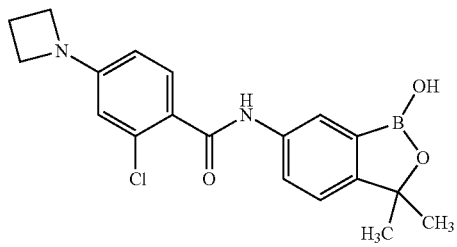 [SMILES: CC1(C)OB(O)c2cc(NC(=O)c3ccc(N4CCC4)cc3Cl)ccc21]

The compound was prepared in a manner similar to AAT-13 replacing C with 4-(azetidin-1-yl)-2-chlorobenzoic acid.

LCMS (M/Z): 371 (M+H); ¹H NMR (400 MHz, acetone) δ ppm 1.49 (s, 6H) 2.41 (quin, J=7.3 Hz, 2H) 3.96 (t, J=7.3 Hz, 4H) 6.39 (d, J=2.1 Hz, 1H) 6.40-6.43 (m, 1H) 7.36 (d, J=8.2 Hz, 1H) 7.48 (d, J=8.2 Hz, 1H) 7.80 (dd, J=8.2, 2.0 Hz, 1H) 8.13 (d, J=1.8 Hz, 1H) 9.23 (br. s., 1H).

9. 6-Azetidin-1-yl-N-(1-hydroxy-3,3-dimethyl-1,3-dihydro-benzo[c][1,2]oxaborol-6-yl)-4-trifluoromethyl-nicotinamide

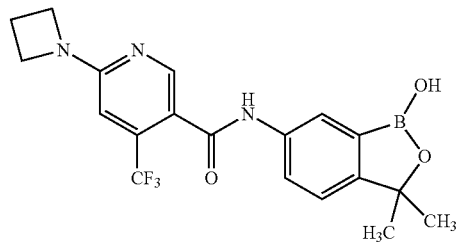 [SMILES: CC1(C)OB(O)c2cc(NC(=O)c3cnc(N4CCC4)cc3C(F)(F)F)ccc21]

The compound was prepared in a manner similar to AAT-13 replacing C with 6-(azetidin-1-yl)-4-(trifluoromethyl)nicotinic acid.

LCMS (M/Z): 406 (M+H); ¹H NMR (400 MHz, DMSO-d6) δ ppm 1.43 (s, 6H) 2.38 (quin, J=7.47 Hz, 2H) 4.09 (t, J=7.52 Hz, 4H) 6.65 (s, 1H) 7.36 (d, J=8.20 Hz, 1H) 7.64 (dd, J=8.20, 1.95 Hz, 1H) 8.03 (s, 1H) 8.42 (s, 1H) 9.06 (s, 1H) 10.43 (s, 1H).

10. 6-Azeidin-1-yl-N-(1-hydroxy-3,3-dimethyl-1,3-dihydro-benzo[c][1,2]oxaborol-6-yl)-2-trifluoromethyl-nicotinamide

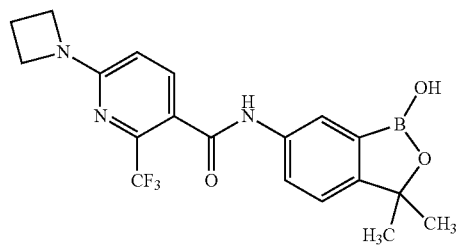 [SMILES: CC1(C)OB(O)c2cc(NC(=O)c3ccc(N4CCC4)nc3C(F)(F)F)ccc21]

The compound was prepared in a manner similar to AAT-13 replacing C with 6-(azetidin-1-yl)-2-(trifluoromethyl)nicotinic acid.

LCMS (M/Z): 406 (M+H); ¹H NMR (400 MHz, DMSO-d6) δ ppm 1.44 (s, 6H) 3.57-3.60 (m, 4H) 3.71 (d, J=5.2 Hz, 4H) 3.73 (br. s., 1H) 7.18 (d, J=8.8 Hz, 1H) 7.37 (d, J=8.2 Hz, 1H) 7.63 (dd, J=8.3, 1.9 Hz, 1H) 7.86 (d, J=8.8 Hz, 1H) 8.00 (d, J=1.7 Hz, 1H) 9.07 (s, 1H) 10.41 (s, 1H).

11. 2-Chloro-N-(1-hydroxy-3,3-dimethyl-1,3-dihydro-benzo[c][1,2]oxaborol-6-yl)-4-pyrrolidin-1-yl-benzamide

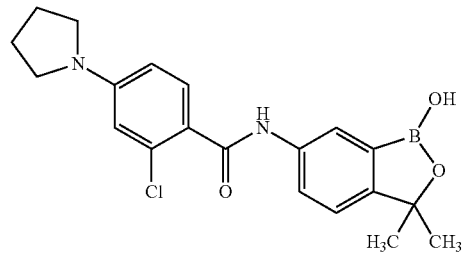 [SMILES: CC1(C)OB(O)c2cc(NC(=O)c3ccc(N4CCCC4)cc3Cl)ccc21]

The compound was prepared in a manner similar to AAT-13 replacing C with 2-chloro-4-(pyrrolidin-1-yl)benzoic acid.

LCMS (M/Z): 385 (M+H); ¹H NMR (400 MHz, DMSO-d6) δ ppm 1.44 (s, 6H) 1.94-2.00 (m, 4H) 3.27 (t, J=6.5 Hz, 5H) 6.52-6.60 (m, 2H) 7.34 (d, J=8.2 Hz, 1H) 7.41 (d, J=8.5 Hz, 1H) 7.68 (d, J=8.2 Hz, 1H) 8.03 (s, 1H) 9.05 (br. s., 1H) 10.13 (s, 1H).

12. N-(1-Hydroxy-3,3-dimethyl-1,3-dihydro-benzo[c][1,2]oxaborol-6-yl)-4-pyrrolidin-1-yl-2-trifluoromethyl-benzamide

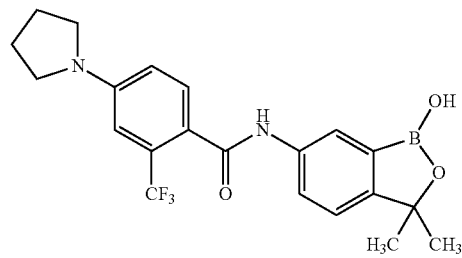 [SMILES: CC1(C)OB(O)c2cc(NC(=O)c3ccc(N4CCCC4)cc3C(F)(F)F)ccc21]

The compound was prepared in a manner similar to AAT-13 replacing C with 4-(pyrrolidin-1-yl)-2-(trifluoromethyl)benzoic acid.

LCMS (M/Z): 419 (M+H); ¹H NMR (400 MHz, DMSO-d6) δ ppm 1.44 (s, 6H) 1.99 (ddd, J=6.4, 3.5, 3.3 Hz, 4H) 3.31-3.35 (m, 4H) 6.78-6.83 (m, 2H) 7.35 (d, J=8.3 Hz, 1H) 7.49 (d, J=9.2 Hz, 1H) 7.64 (dd, J=8.1, 1.9 Hz, 1H) 8.04 (d, J=1.4 Hz, 1H) 9.05 (s, 1H) 10.26 (s, 1H).

13. 2-Chloro-N-(1-hydroxy-3,3-dimenthyl-1,3-dihydro-benzo[c][1,2]oxaborol-6-yl)-4-(2-oxo-pyrrolidin-1-yl)-benzamide

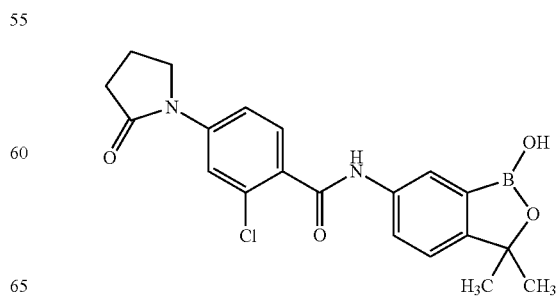

The compound was prepared in a manner similar to AAT-13 replacing C with 2-chloro-4-(2-oxopyrrolidin-1-yl)benzoic acid.

LCMS (M/Z): 399 (M+H); ¹H NMR (400 MHz, DMSO-d6) δ ppm 1.41 (s, 6H) 2.01-2.10 (m, 2H) 2.52 (t, J=8.1 Hz, 2H) 3.84 (t, J=7.1 Hz, 2H) 7.34 (d, J=8.4 Hz, 1H) 7.53-7.59 (m, 1H) 7.61-7.68 (m, 2H) 7.92 (d, J=2.0 Hz, 1H) 8.01 (d, J=1.8 Hz, 1H) 9.04 (s, 1H) 10.41 (s, 1H).

14. N-(1-Hydroxy-3,3-dimethyl-1,3-dihydro-benzo[c][1,2]oxaborol-6-yl)-4-(2-oxo-pyrrolidin-1-yl)-2-trifluoromethyl-benzamide

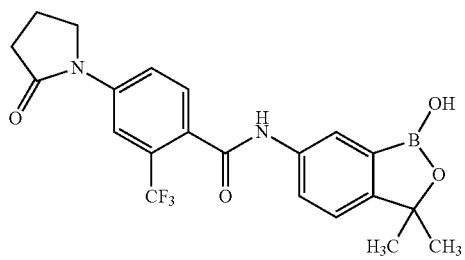 [SMILES: CC1(C)OB(O)c2cc(NC(=O)c3ccc(N4CCCC4=O)cc3C(F)(F)F)ccc21]

The compound was prepared in a manner similar to AAT-13 replacing C with 4-(2-oxopyrrolidin-1-yl)-2-(trifluoromethyl)benzoic acid.

LCMS (M/Z): 433 (M+H); ¹H NMR (400 MHz, DMSO-d6) δ ppm 1.40 (s, 6H) 2.08 (s, 2H) 2.54 (t, J=8.1 Hz, 2H) 3.89 (t, J=6.9 Hz, 2H) 7.34 (d, J=8.2 Hz, 1H) 7.61 (dd, J=8.3, 2.0 Hz, 1H) 7.68 (d, J=8.4 Hz, 1H) 7.84 (d, J=2.0 Hz, 1H) 8.00 (d, J=1.8 Hz, 1H) 8.26 (d, J=2.1 Hz, 1H) 9.04 (s, 1H) 10.49 (s, 1H).

15. N-(1-Hydroxy-3,3-dimethyl-1,3-dihydro-benzo[c][1,2]oxaborol-6-yl)-4-pyrazol-1-yl-2-trifluoromethyl-benzamide

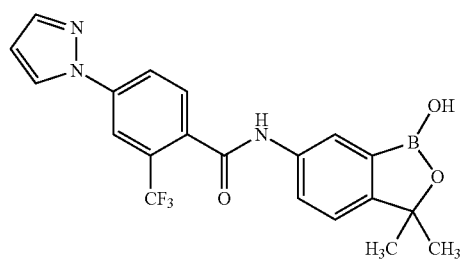 [SMILES: CC1(C)OB(O)c2cc(NC(=O)c3ccc(-n4cccn4)cc3C(F)(F)F)ccc21]

The compound was prepared in a manner similar to AAT-13 replacing C with 4-(1H-pyrazol-1-yl)-2-(trifluoromethyl)benzoic acid.

LCMS (M/Z): 416 (M+H); ¹H NMR (400 MHz, DMSO-d6) δ ppm 1.41 (s, 6H) 6.58-6.64 (m, 1H) 7.36 (d, J=8.4 Hz, 1H) 7.62 (dd, J=8.2, 2.0 Hz, 1H) 7.78-7.86 (m, 2H) 8.02 (d, J=2.0 Hz, 1H) 8.20-8.28 (m, 2H) 8.73 (d, J=2.5 Hz, 1H) 9.06 (s, 1H) 10.58 (s, 1H).

16. N-(1-Hydroxy-3,3-dimethyl-1,3-dihydro-benzo[c][1,2]oxaborol-6-yl)-6-pyrazol-1-yl-4-trifluoromethyl-nicotinamide

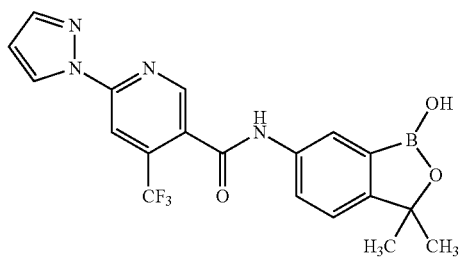 [SMILES: CC1(C)OB(O)c2cc(NC(=O)c3cnc(-n4cccn4)cc3C(F)(F)F)ccc21]

The compound was prepared in a manner similar to AAT-13 replacing C with 6-(1H-pyrazol-1-yl)-4-(trifluoromethyl)nicotinic acid.

LCMS (M/Z): 417 (M+H); ¹H NMR (400 MHz, DMSO-d6) δ ppm 1.45 (s, 6H) 6.70 (dd, J=2.6, 1.7 Hz, 1H) 7.42 (d, J=8.2 Hz, 1H) 7.67 (dd, J=8.2, 2.0 Hz, 1H) 7.97 (d, J=1.6 Hz, 1H) 8.06 (d, J=2.0 Hz, 1H) 8.22 (s, 1H) 8.72-8.77 (m, 1H) 8.94 (s, 1H) 9.12 (s, 1H) 10.79 (s, 1H).

17. 2-Chloro-N-(1-hydroxy-3,3-dimethyl-1,3-dihydro-benzo[c][1,2]oxaborol-6-yl)-4-(3-methyl-pyrazol-1-yl)-benzamide

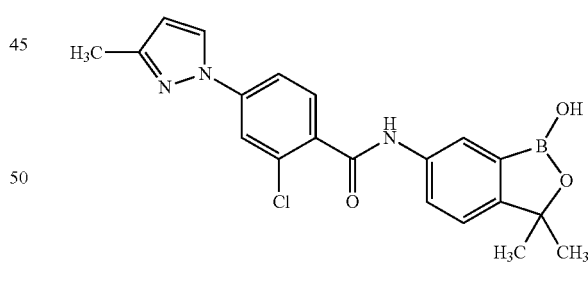

The compound was prepared in a manner similar to AAT-13 replacing C with 2-chloro-4-(3-methyl-1H-pyrazol-1-yl)benzoic acid.

LCMS (M/Z): 396 (M+H); ¹H NMR (400 MHz, DMSO-d6) δ ppm 1.45 (s, 6H) 2.29 (s, 3H) 6.41 (d, J=2.4 Hz, 1H) 7.39 (d, J=8.2 Hz, 1H) 7.66-7.73 (m, 2H) 7.90 (d, J=8.4 Hz, 1H) 8.01 (d, J=2.0 Hz, 2H) 8.54 (s, 1H) 9.09 (s, 1H) 10.53 (s, 1H).

18. 2-Chloro-4-(4-chloro-pyrazol-1-yl)-N-(1-hydroxy-3,3-dimethyl-1,3-dihydro-benzo[c][1,2]oxaborol-6-yl)-benzamide

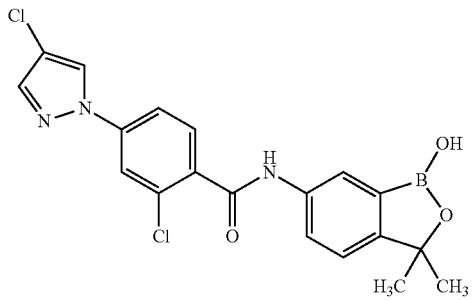 [SMILES: CC1(C)OB(O)c2cc(NC(=O)c3ccc(-n4cc(Cl)cn4)cc3Cl)ccc21]

The compound was prepared in a manner similar to AAT-13 replacing C with 2-chloro-4-(4-chloro-1H-pyrazol-1-yl)benzoic acid.

LCMS (M/Z): 416 (M+H); ¹H NMR (400 MHz, DMSO-d6) δ ppm 1.45 (s, 6H) 7.39 (d, J=8.2 Hz, 1H) 7.69 (dd, J=8.2, 2.0 Hz, 1H) 7.75 (d, J=8.4 Hz, 1H) 7.93 (dd, J=8.4, 2.2 Hz, 1H) 7.97 (s, 1H) 8.06 (t, J=2.0 Hz, 2H) 8.97 (s, 1H) 9.09 (s, 1H) 10.56 (s, 1H).

19. 2-Chloro-N-(1-hydroxy-3,3-dimethyl-1,3-dihydro-benzo[c][1,2]oxaborol-6-yl)-4-imidazol-1-yl-benzamide

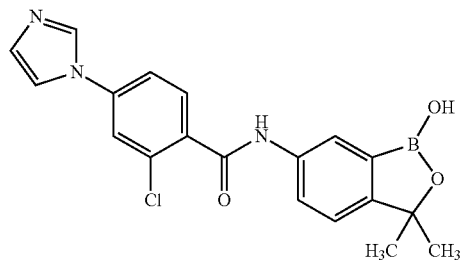 [SMILES: CC1(C)OB(O)c2cc(NC(=O)c3ccc(-n4ccnc4)cc3Cl)ccc21]

The compound was prepared in a manner similar to AAT-13 replacing C with 2-chloro-4-(1H-imidazol-1-yl)benzoic acid.

LCMS (M/Z): 382 (M+H); ¹H NMR (400 MHz, DMSO-d6) δ ppm 1.45 (s, 6H) 7.15 (s, 1H) 7.39 (d, J=8.2 Hz, 1H) 7.70 (dd, J=8.2, 1.9 Hz, 1H) 7.72-7.75 (m, 1H) 7.78-7.83 (m, 1H) 7.92 (s, 1H) 8.01 (d, J=2.1 Hz, 1H) 8.06 (d, J=1.9 Hz, 1H) 8.44 (s, 1H) 9.09 (s, 1H) 10.56 (s, 1H).

20. N-(1-Hydroxy-3,3-dimethyl-1,3-dihydro-benzo[c][1,2]oxaborol-6-yl)-6-imidazol-1-yl-2-trifluoromethyl-nicotinamide

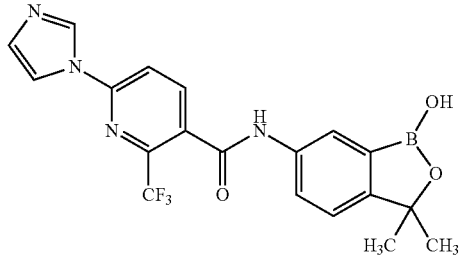 [SMILES: CC1(C)OB(O)c2cc(NC(=O)c3ccc(-n4ccnc4)nc3C(F)(F)F)ccc21]

The compound was prepared in a manner similar to AAT-13 replacing C with 6-(1H-imidazol-1-yl)-2-(trifluoromethyl)nicotinic acid.

LCMS (M/Z): 417 (M+H); ¹H NMR (400 MHz, DMSO-d6) δ ppm 1.46 (s, 6H) 7.21 (d, J=0.8 Hz, 1H) 7.43 (d, J=8.2 Hz, 1H) 7.66 (dd, J=8.2, 2.0 Hz, 1H) 8.01-8.07 (m, 2H) 8.30 (d, J=8.5 Hz, 1H) 8.49 (d, J=8.4 Hz, 1H) 8.66 (s, 1H) 9.12 (s, 1H) 10.74 (s, 1H).

21. N-(1-Hydroxy-3,3-dimethyl-1,3-dihydro-benzo[c][1,2]oxaborol-6-yl)-6-imidazo-1-yl-4-trifluoromethyl-nicotinamide

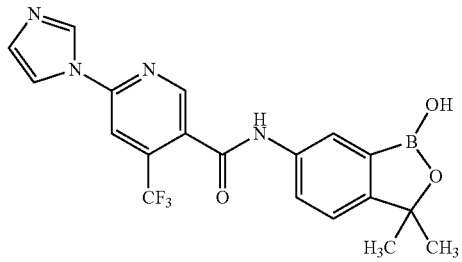 [SMILES: CC1(C)OB(O)c2cc(NC(=O)c3cnc(-n4ccnc4)cc3C(F)(F)F)ccc21]

The compound was prepared in a manner similar to AAT-13 replacing C with 6-(1H-imidazol-1-yl)-4-(trifluoromethyl)nicotinic acid.

LCMS (M/Z): 417 (M+H); ¹H NMR (400 MHz, DMSO-d6) δ ppm 1.45 (s, 6H) 7.20 (s, 1H) 7.41 (d, J=8.2 Hz, 1H) 7.66 (dd, J=8.3, 2.1 Hz, 1H) 8.04 (d, J=1.8 Hz, 1H) 8.16 (t, J=1.4 Hz, 1H) 8.33 (s, 1H) 8.75 (s, 1H) 8.93 (s, 1H) 9.11 (s, 1H) 10.79 (s, 1H).

22. 2-Chloro-N-(1-hydroxyl-3,3-dimethyl-1,3-dihydro-benzo[c][1,2]oxaborol-6-yl)-4-[1,2,4]triazol-1-yl-benzamide

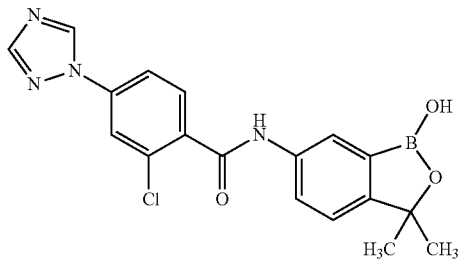 [SMILES: CC1(C)OB(O)c2cc(NC(=O)c3ccc(-n4cncn4)cc3Cl)ccc21]

The compound was prepared in a manner similar to AAT-13 replacing C with 2-chloro-4-(1H-1,2,4-triazol-1-yl)benzoic acid.

LCMS (M/Z): 414 (M+H); LCMS (M/Z): 383 (M+H); $^1$H NMR (400 MHz, DMSO-d6) δ ppm 1.45 (s, 6H) 7.40 (d, J=8.2 Hz, 1H) 7.70 (dd, J=8.3, 2.0 Hz, 1H) 7.80 (d, J=8.3 Hz, 1H) 7.98 (dd, J=8.3, 2.1 Hz, 1H) 8.07 (d, J=1.9 Hz, 1H) 8.15 (d, J=2.0 Hz, 1H) 8.32 (s, 1H) 9.10 (s, 1H) 9.46 (s, 1H) 10.60 (s, 1H).

23. 2-Chloro-N-(1-hydroxy-3,3-dimethyl-1,3-dihydrobenzo[c][1,2]oxaborol-6-yl)-4-(4H-1,2,4-triazol-4-yl)benzamide

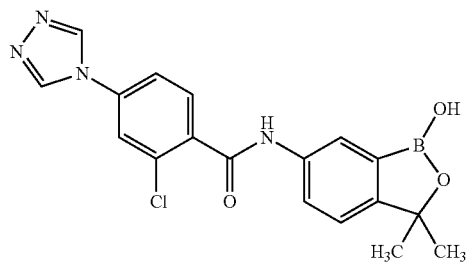 [SMILES: CC1(C)OB(O)c2cc(NC(=O)c3ccc(-n4cnnc4)cc3Cl)ccc21]

The compound was prepared in a manner similar to AAT-13 replacing C with 2-chloro-4-(4H-1,2,4-triazol-4-yl)benzoic acid.

LCMS (M/Z): 383 (M+H); $^1$H NMR (400 MHz, DMSO-d6) δ ppm 1.44 (s, 6H) 7.40 (d, J=8.0 Hz, 1H) 7.73 (dd, J=8.0, 1.5 Hz, 1H) 7.79 (d, J=8.2 Hz, 1H) 7.84 (dd, J=8.2, 2.0 Hz, 1H) 8.06 (d, J=2.5 Hz, 1H) 8.09 (d, J=2.0 Hz, 1H) 9.13 (s, 1H) 9.28 (s, 2H) 9.46 (s, 1H) 10.62 (s, 1H).

24. 2-Chloro-4-(3-chloro-pyrrolo[2,3-b]pyridin-1-yl)-N-(1-hydroxy-3,3-dimethyl-1,3-dihydro-benzo[c][1,2]oxaborol-6-yl)-benzamide

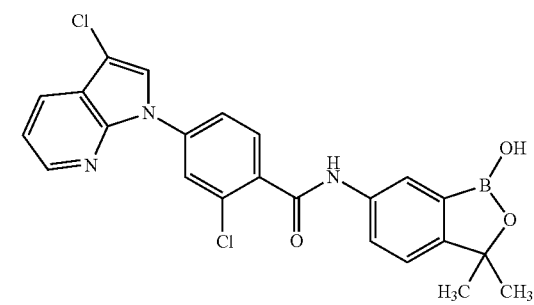 [SMILES: CC1(C)OB(O)c2cc(NC(=O)c3ccc(-n4cc(Cl)c5cccnc54)cc3Cl)ccc21]

The compound was prepared in a manner similar to AAT-13 replacing C with 2-chloro-4-(3-chloro-1H-pyrrolo[2,3-b]pyridin-1-yl)benzoic acid.

LCMS (M/Z): 466 (M+H); $^1$H NMR (400 MHz, DMSO-d6) δ ppm 1.45 (s, 6H) 7.41 (dd, J=4.2, 3.7 Hz, 2H) 7.72 (dd, J=8.2, 2.0 Hz, 1H) 7.78 (d, J=8.4 Hz, 1H) 8.10 (dd, J=11.1, 1.5 Hz, 3H) 8.29 (d, J=2.1 Hz, 1H) 8.42 (s, 1H) 8.49 (d, J=1.5 Hz, 1H) 9.10 (s, 1H) 10.60 (s, 1H).

25. 2-Chloro-N-(1-hydroxy-3,3-dimethyl-1,3-dihydro-benzo[c][1,2]oxaborol-6-yl)-4-piperidin-1-yl-benzamide

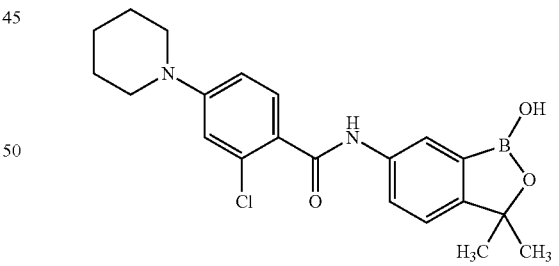

The compound was prepared in a manner similar to AAT-13 replacing C with 2-chloro-4-(piperidin-1-yl)benzoic acid.

LCMS (M/Z): 399 (M+H); $^1$H NMR (400 MHz, acetone) δ ppm 1.49 (s, 6H) 1.60-1.72 (m, 6H) 3.25-3.39 (m, 5H) 6.89-6.96 (m, 2H) 7.36 (d, J=8.2 Hz, 1H) 7.50 (d, J=9.4 Hz, 1H) 7.81 (dd, J=8.3, 2.1 Hz, 1H) 8.14 (d, J=1.8 Hz, 1H) 9.26 (br. s., 1H).

26. 2-Chloro-4-(4,4-dimethyl-piperidin-1-yl)-N-(1-hydroxy-3,3-dimethyl-1,3-dihydro-benzo[c][1,2]oxaborol-6-yl)-benzamide

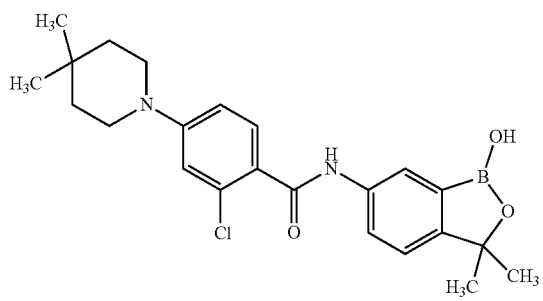

The compound was prepared in a manner similar to AAT-13 replacing C with 2-chloro-4-(4,4-dimethylpiperidin-1-yl)benzoic acid.

LCMS (M/Z): 427 (M+H); $^1$H NMR (400 MHz, acetone) δ ppm 1.01 (s, 6H) 1.49 (s, 10H) 3.32-3.38 (m, 4H) 6.91-6.98 (m, 2H) 7.37 (d, J=8.2 Hz, 1H) 7.50 (d, J=9.4 Hz, 1H) 7.81 (dd, J=8.3, 2.0 Hz, 1H) 8.14 (d, J=1.8 Hz, 1H) 9.25 (br. s., 1H).

27. 2-Chloro-N-(1-hydroxy-3,3-dimethyl-1,3-dihydrobenzo[c][1,2]oxaborol-6-yl)-4-(4-methylpiperazin-1-yl)benzamide hydrochloride

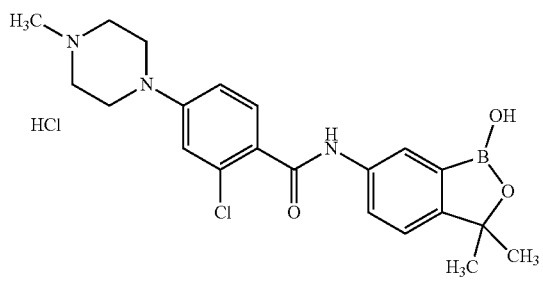

The compound was prepared in a manner similar to AAT-13 replacing C with 2-chloro-4-(4-methylpiperazin-1-yl)benzoic acid.

$^1$H NMR (400 MHz, DMSO-d6) δ ppm 11.05 (s, 1H), 10.29 (s, 1H), 8.02 (s, 1H), 7.65 (d, 1H, J=8.4 Hz), 7.46 (d, 1H, J=8.4 Hz), 7.35-7.334 (d, 1H, J=8.4 Hz), 7.12 (s, 1H), 7.03 (d, 1H, J=8.4 Hz), 3.96 (d, 2H, J=12.8 Hz), 3.45 (d, 2H, J=12.8 Hz), 3.22-3.08 (m, 4H), 2.78 (s, 3H), 1.42 (s, 6H).

28. 2-Chloro-N-(1-hydroxy-3,3-dimethyl-1,3-dihydro-benzo[c][1,2]oxaborol-6-yl)-4-morpholin-4-yl-benzamide

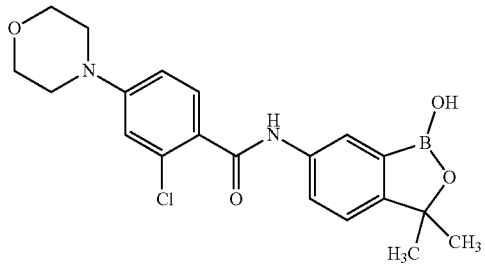

The compound was prepared in a manner similar to AAT-13 replacing C with 2-chloro-4-morpholinobenzoic acid.

LCMS (M/Z): 401 (M+H); $^1$H NMR (400 MHz, DMSO-d6) δ ppm 1.44 (s, 6H) 3.17-3.25 (m, 4H) 3.74 (dd, J=5.8, 4.0 Hz, 4H) 6.99 (dd, J=8.6, 2.3 Hz, 1H) 7.03 (d, J=2.3 Hz, 1H) 7.36 (d, J=8.2 Hz, 1H) 7.44 (d, J=8.6 Hz, 1H) 7.68 (dd, J=8.3, 1.7 Hz, 1H) 8.04 (s, 1H) 9.05 (s, 1H) 10.26 (s, 1H).

29. N-(1-Hydroxy-3,3-dimethyl-1,3-dihydro-benzo[c][1,2]oxaborol-6-yl)-4-morpholin-4-yl-2-trifluoromethyl-benzamide

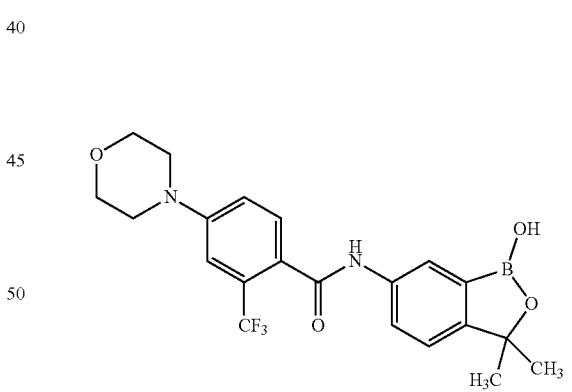

The compound was prepared in a manner similar to AAT-13 replacing C with 4-morpholino-2-(trifluoromethyl)benzoic acid.

LCMS (M/Z): 335 (M+H); $^1$H NMR (400 MHz, DMSO-d6) δ ppm 1.40 (s, 6H) 3.20-3.25 (m, 4H) 3.70-3.75 (m, 4H) 7.19-7.26 (m, 2H) 7.32 (d, J=8.2 Hz, 1H) 7.50 (d, J=8.0 Hz, 1H) 7.60 (dd, J=8.2, 2.0 Hz, 1H) 8.00 (d, J=1.4 Hz, 1H) 9.02 (s, 1H) 10.32 (s, 1H).

30. N-(1-Hydroxy-3,3-dimethyl-1,3-dihydro-benzo[c][1,2]oxaborol-6-yl)-6-morpholin-4-yl-4-trifluoromethyl-nicotinamide

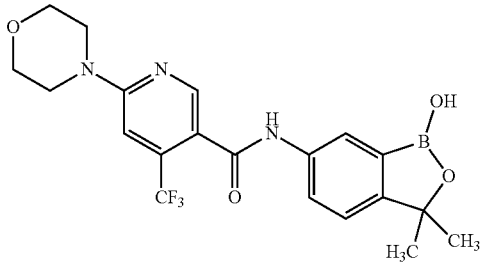 [SMILES: CC1(C)OB(O)c2cc(NC(=O)c3cnc(N4CCOCC4)cc3C(F)(F)F)ccc21]

The compound was prepared in a manner similar to AAT-13 replacing C with 6-morpholino-4-(trifluoromethyl)nicotinic acid.

LCMS (M/Z): 436 (M+H); $^1$H NMR (400 MHz, DMSO-d6) δ ppm 1.44 (s, 7H) 1.45-1.46 (m, 1H) 3.62-3.73 (m, 11H) 7.16 (s, 1H) 7.35-7.39 (m, 1H) 8.02-8.05 (m, 1H) 8.48-8.50 (m, 1H) 10.45 (s, 1H).

31. N-(1-Hydroxy-3,3-dimethyl-1,3-dihydro-benzo[c][1,2]oxaborol-6-yl)-6-morpholin-4-yl-2-trifluoromethyl-nicotinamide

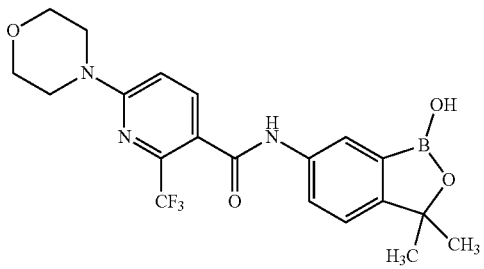 [SMILES: CC1(C)OB(O)c2cc(NC(=O)c3ccc(N4CCOCC4)nc3C(F)(F)F)ccc21]

The compound was prepared in a manner similar to AAT-13 replacing C with 6-morpholino-2-(trifluoromethyl)nicotinic acid.

LCMS (M/Z): 436 (M+H); $^1$H NMR (400 MHz, DMSO-d6) δ ppm 1.44 (s, 6H) 2.38 (t, J=7.6 Hz, 2H) 4.05 (t, J=7.5 Hz, 4H) 6.66 (d, J=8.6 Hz, 1H) 7.36 (d, J=8.2 Hz, 1H) 7.62 (dd, J=8.2, 1.9 Hz, 1H) 7.78 (d, J=8.6 Hz, 1H) 8.00 (d, J=1.7 Hz, 1H) 9.06 (s, 1H) 10.39 (s, 1H).

32. N-(1-Hydroxy-3,3-dimethyl-1,3-dihydro-benzo[c][1,2]oxaborol-6-yl)-4-(6-oxo-6H-pyridazin-1-yl)-2-trifluoromethyl-benzamide

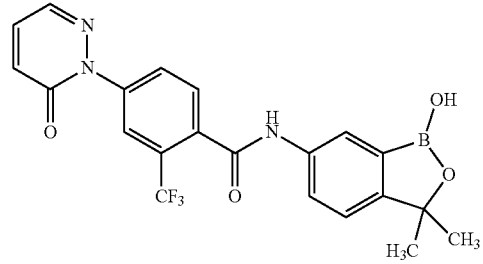 [SMILES: CC1(C)OB(O)c2cc(NC(=O)c3ccc(-n4ncccc4=O)cc3C(F)(F)F)ccc21]

The compound was prepared in a manner similar to AAT-13 replacing C with 4-(6-oxopyridazin-1 (6H)-yl)-2-(trifluoromethyl)benzoic acid.

LCMS (M/Z): 444 (M+H); $^1$H NMR (400 MHz, DMSO-d6) δ ppm 1.41 (s, 6H) 7.10 (dd, J=9.5, 1.7 Hz, 1H) 7.33-7.39 (m, 1H) 7.51 (dd, J=9.6, 3.7 Hz, 1H) 7.62 (dd, J=8.1, 2.0 Hz, 1H) 7.81 (d, J=8.0 Hz, 1H) 7.97-8.04 (m, 2H) 8.06 (d, J=1.8 Hz, 1H) 8.11 (dd, J=3.8, 1.5 Hz, 1H) 9.06 (s, 1H) 10.64 (s, 1H).

33. 6-Azetidin-1-yl-N-(1-hydroxy-3,4-dihydro-1H-benzo[c][1,2]oxaborinin-7-yl)-4-trifluoromethyl-nicotinamide

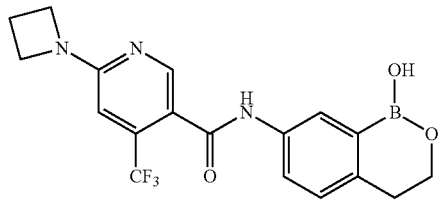 [SMILES: O=C(Nc1ccc2c(c1)B(O)OCC2)c1cnc(N2CCC2)cc1C(F)(F)F]

The compound was prepared in a manner similar to AAT-13 replacing C with 6-(azetidin-1-yl)-4-(trifluoromethyl)nicotinic acid and D with 7-amino-3,4-dihydro-1H-benzo[c][1,2]oxaborinin-1-ol.

LCMS (M/Z): 392 (M+H); $^1$H NMR (400 MHz, DMSO-d6) δ ppm 2.38 (quin, J=7.5 Hz, 2H) 2.83 (t, J=5.9 Hz, 2H) 4.04-4.11 (m, 6H) 6.64 (s, 1H) 7.17 (d, J=8.2 Hz, 1H) 7.67 (dd, J=8.0, 2.3 Hz, 1H) 7.92 (d, J=2.1 Hz, 1H) 8.40 (s, 1H) 8.42 (s, 1H) 10.33 (s, 1H).

34. 2-Chloro-N-(1-hydroxy-3,4-dihydro-1H-benzo[c][1,2]oxaborin-7-yl)-4-pyrazol-1-yl-benzamide

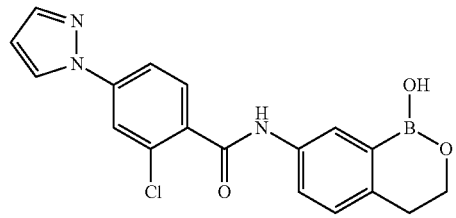 [SMILES: O=C(Nc1ccc2c(c1)B(O)OCC2)c1ccc(-n2cccn2)cc1Cl]

The compound was prepared in a manner similar to AAT-13 replacing C with 2-chloro-4-(1H-pyrazol-1-yl)benzoic acid and D with 7-amino-3,4-dihydro-1H-benzo[c][1,2]oxaborinin-1-ol.

LCMS (M/Z): 368 (M+H); ¹H NMR (400 MHz, DMSO-d6) δ ppm 2.77-2.93 (m, 2H) 4.01-4.12 (m, 1H) 4.17 (t, J=6.0 Hz, 1H) 6.53-6.65 (m, 1H) 7.13-7.27 (m, 1H) 7.63-7.77 (m, 2H) 7.83 (s, 1H) 7.89-8.11 (m, 3H) 8.44 (s, 1H) 8.67 (d, J=2.5 Hz, 1H) 10.45 (s, 1H).

35. 2-Chloro-N-(1-hydroxy-3,4-dihydro-1H-benzo[c][1,2]oxaborin-7-yl)-4-(3-methyl-pyrazol-1-yl)-benzamide

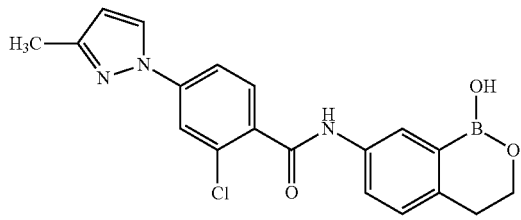 [SMILES: Cc1ccn(-c2ccc(C(=O)Nc3ccc4c(c3)B(O)OCC4)c(Cl)c2)n1]

The compound was prepared in a manner similar to AAT-13 replacing C with 2-chloro-4-(3-methyl-1H-pyrazol-1-yl)benzoic acid and D with 7-amino-3,4-dihydro-1H-benzo[c][1,2]oxaborinin-1-ol.

LCMS (M/Z): 382 (M+H); ¹H NMR (400 MHz, DMSO-d6) δ ppm 2.29 (s, 3H) 2.84 (t, J=5.8 Hz, 2H) 4.07 (t, J=5.9 Hz, 2H) 6.41 (d, J=2.4 Hz, 1H) 7.20 (d, J=8.2 Hz, 1H) 7.68 (d, J=8.4 Hz, 1H) 7.72 (dd, J=8.2, 2.3 Hz, 1H) 7.88 (dd, J=8.4, 2.1 Hz, 1H) 7.99 (dd, J=10.3, 2.2 Hz, 2H) 8.43 (s, 1H) 8.54 (d, J=2.4 Hz, 1H) 10.43 (s, 1H).

36. 2-Chloro-4-(4-chloro-pyrazol-1-yl)-N-(1-hydroxy-3,4-dihydro-1H-benzo[c][1,2]oxaborinin-7-yl)-benzamide

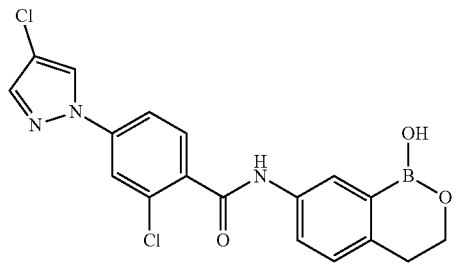 [SMILES: O=C(Nc1ccc2c(c1)B(O)OCC2)c1ccc(-n2cc(Cl)cn2)cc1Cl]

The compound was prepared in a manner similar to AAT-13 replacing C with 2-chloro-4-(4-chloro-1H-pyrazol-1-yl)benzoic acid and D with 7-amino-3,4-dihydro-1H-benzo[c][1,2]oxaborinin-1-ol.

LCMS (M/Z): 402 (M+H); ¹H NMR (400 MHz, DMSO-d6) δ ppm 2.84 (t, J=5.8 Hz, 2H) 4.07 (t, J=5.9 Hz, 2H) 7.20 (d, J=8.2 Hz, 1H) 7.70-7.76 (m, 2H) 7.92 (dd, J=8.4, 2.2 Hz, 1H) 7.96-7.99 (m, 2H) 8.05 (d, J=2.1 Hz, 1H) 8.44 (s, 1H) 8.96 (s, 1H) 10.46 (s, 1H).

37. 2-Chloro-4-(3-chloro-pyrrolo[2,3-b]pyridin-1-yl)-N-(1-hydroxy-3,4-dihydro-1H benzo[c][1,2]oxaborinin-7-yl)-benzamide

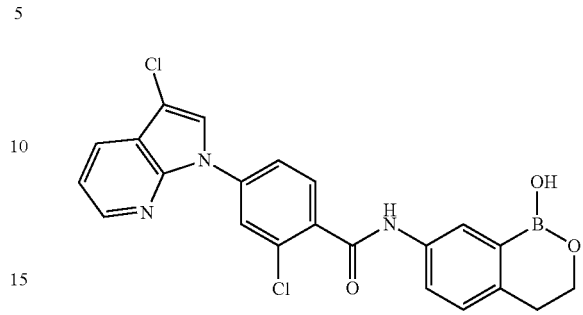

The compound was prepared in a manner similar to AAT-13 replacing C with 2-chloro-4-(3-chloro-1H-pyrrolo[2,3-b]pyridin-1-yl)benzoic acid and D with 7-amino-3,4-dihydro-1H-benzo[c][1,2]oxaborinin-1-ol.

LCMS (M/Z): 452 (M+H); ¹H NMR (400 MHz, DMSO-d6) δ ppm 2.81 (t, J=5.8 Hz, 2H) 4.04 (t, J=5.6 Hz, 2H) 7.17 (d, J=8.2 Hz, 1H) 7.36 (dd, J=7.9, 4.7 Hz, 1H) 7.70 (dd, J=8.2, 2.2 Hz, 2H) 7.96 (d, J=2.2 Hz, 1H) 8.07 (ddd, J=10.4, 8.3, 1.8 Hz, 2H) 8.25 (d, J=2.1 Hz, 1H) 8.37-8.42 (m, 2H) 8.46 (dd, J=4.7, 1.5 Hz, 1H) 10.46 (s, 1H).

38. 2-Chloro-N-(1-hydroxy-3,4-dihydro-1H-benzo[c][1,2]oxaborinin-7-yl)-4-(4-methylpiperazin-1-yl)benzamide hydrochloride

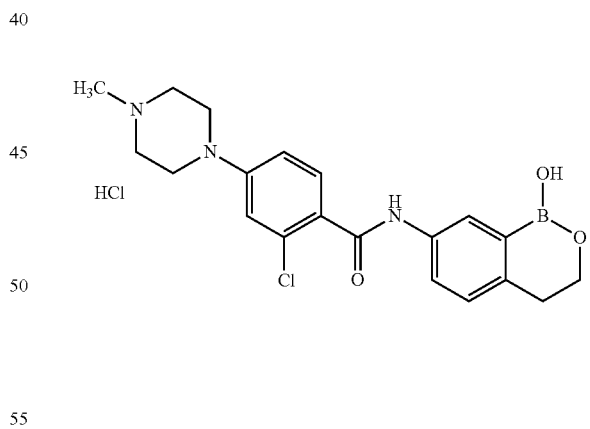

The compound was prepared in a manner similar to AAT-13 replacing C with 2-chloro-4-(4-methylpiperazin-1-yl)benzoic acid and D with 7-amino-3,4-dihydro-1H-benzo[c][1,2]oxaborinin-1-ol.

LCMS (M/Z): 400 (M+H); ¹H NMR (400 MHz, DMSO-d6) δ ppm 611.23 (s, 1H), 10.22 (s, 1H), 7.97 (s, 1H), 7.72 (d, 1H, J=8.4 Hz), 7.47 (d, 1H, J=8.4 Hz), 7.17 (d, 1H, J=8.4 Hz), 7.14 (s, 1H), 7.05 (d, 1H, J=8.4 Hz), 4.07 (t, 2H, J=6.0 Hz), 4.00 (d, 1H, J=13.2 Hz), 3.47 (d, 2H, J=11.6 Hz), 3.21 (t, 2H, J=12.0 Hz), 3.11 (q, 2H, J=11.6 Hz), 2.83 (t, 2H, J=6.0 Hz), 2.80 (s, 3H).

39. 2-Chloro-N-(1-hydroxy-3,4-dihydro-1H-benzo[c][1,2]oxaborin-7-yl)-4-morpholin-4-yl-benzamide

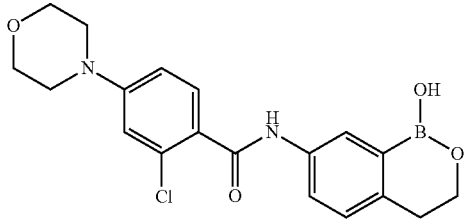 [SMILES: O=C(Nc1ccc2c(c1)B(O)OCC2)c1ccc(N2CCOCC2)cc1Cl]

The compound was prepared in a manner similar to AAT-13 replacing C with 2-chloro-4-morpholinobenzoic acid and D with 7-amino-3,4-dihydro-1H-benzo[c][1,2]oxaborinin-1-ol.

LCMS (M/Z): 387 (M+H); $^1$H NMR (400 MHz, DMSO-d6) δ ppm 2.75-2.92 (m, 2H) 3.18-3.27 (m, 4H) 3.68-3.79 (m, 4H) 4.01-4.12 (m, 1H) 4.17 (t, J=5.9 Hz, 1H) 6.98 (dd, J=8.8, 2.3 Hz, 1H) 7.03 (d, J=2.3 Hz, 1H) 7.17 (dd, J=8.1, 6.0 Hz, 1H) 7.44 (d, J=8.6 Hz, 1H) 7.70 (d, J=8.2 Hz, 1H) 7.96 (br. s., 1H) 8.41 (s, 1H) 10.16 (s, 1H).

40. N-(1-Hydroxy-3,4-dihydro-1H-benzo[c][1,2]oxaborinin-7-yl)-6-morpholin-4-yl-4-trifluoromethyl-nicotinamide

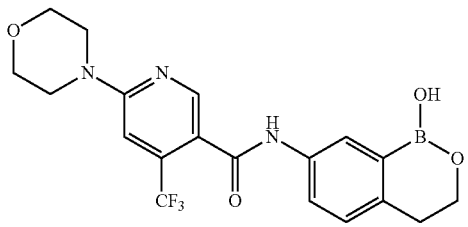 [SMILES: O=C(Nc1ccc2c(c1)B(O)OCC2)c1cnc(N2CCOCC2)cc1C(F)(F)F]

The compound was prepared in a manner similar to AAT-13 replacing C with 6-morpholino-4-(trifluoromethyl)nicotinic acid and D with 7-amino-3,4-dihydro-1H-benzo[c][1,2]oxaborinin-1-ol.

LCMS (M/Z): 422 (M+H); $^1$H NMR (400 MHz, DMSO-d6) δ ppm 2.84 (t, J=5.8 Hz, 2H) 3.65 (t, J=5.2 Hz, 4H) 3.71 (t, J=5.2 Hz, 4H) 4.07 (t, J=5.9 Hz, 2H) 7.16 (s, 1H) 7.18 (d, J=8.2 Hz, 1H) 7.68 (dd, J=8.2, 2.0 Hz, 1H) 7.94 (d, J=1.9 Hz, 1H) 8.43 (s, 1H) 8.48 (s, 1H) 10.36 (s, 1H).

Example 2

*Trypanosoma brucei brucei* or *Trypanosoma congolense* High-Throughput Screening Assay Procedure All experiments were conducted with the bloodstream-form trypanosome [*T. brucei brucei* 427 strain obtained from Seattle Biomedical Research Institute (Seattle, Wash.) and *T. congolense* IL3000 strain]. Parasites were cultured in T-25 vented cap flasks and kept in humidified incubators at 37° C. and 5% $CO_2$. The parasite culture media was complete HMI-9 medium (c.f. Hirumi, Journal of Parasitology 1989, Volume 75, page 985 et seq) containing 10% FBS, 10% Serum Plus medium and penicillin/streptomycin. To ensure log growth phase, trypanosomes were sub-cultured at appropriate dilutions every 2-3 days.

In Vitro Drug Sensitivity Assays

Approximately 50 microliters of log phase cultures were diluted 1:10 in HMI-9 and 10 uL of the diluted culture was removed and counted using a hemocytometer to determine parasite concentration. Parasites were diluted by addition of an appropriate volume of HMI-9 to achieve a final parasite concentration of $2 \times 10^5$/mL. Compounds to be tested were serially diluted in DMSO and 0.5 uL added to 49.5 uL HMI-9 in triplicate 96-well plates using a Biomek NX liquid handler. Parasites from the diluted stock were added to each well (50 uL) using a Multidrop 384 dispenser to give a final concentration of $1.0 \times 10^5$/mL parasites in 0.4% for DMSO. Trypanosomes were incubated with compounds for 72 hrs at 37° C. with 5% $CO_2$. Resazurin (20 uL of 12.5 mg/ml stock) from Sigma-Aldrich was added to each well and plates were incubated for an additional 2-4 hrs. Assay plates were read using an EnVision plate reader at an excitation wavelength of 544 nm and emission of 590 nm. Triplicate data points were averaged to generate sigmoidal dose response curve and determine $IC_{50}$ values using XLfit curve fitting software from IDBS (Guildford, UK).

Biological data for exemplary compounds of the invention is provided in FIG. 1A-B.

Example 3

Activity Against *T. cruzi*

Rat skeletal myoblasts (L-6 cells) can be seeded in 96-well microtitre plates at 2000 cells/well in 100 μL RPMI 1640 medium with 10% FBS and 2 mM l-glutamine. After 24 h the medium can be removed and replaced by 100 μl per well containing 5000 trypomastigote forms of *T. cruzi* Tulahuen strain C2C4 containing the β-galactosidase (Lac Z) gene (Buckner et al. (1996) Efficient technique for screening drugs for activity against *Trypanosoma cruzi* using parasites expressing beta-galactosidase, p. 2592-2597, vol. 40). After 48 h the medium can be removed from the wells and replaced by 100 μl fresh medium with or without a serial drug dilution of seven 3-fold dilution steps covering a range from 90 to 0.123 μg/ml. After 96 h of incubation the plates can be inspected under an inverted microscope to assure growth of the controls and sterility. Then the substrate CPRG/Nonidet (50 μl) can be added to all wells. A color reaction can be within 2-6 h and can be read photometrically at 540 nm. Data can be transferred into the graphic programme Softmax Pro (Molecular Devices), to calculated $IC_{50}$ values.

Example 4

Acute Murine Model of *T. congolense* Infection

Female NMRI mice were inoculated with 10,000 parasites of the STIB 736/IL 1180 strain of *T. congolense*. Seven days post-infection, treatment was initiated QD for 1 day with 10 mg/kg or 4 days with 1, 3, 10 mg/kg intraperitoneally (IP), N=4 mice/group. Mice were monitored for 60 days for survival. The control group of mice (receiving no drug treatment) and the group of mice receiving only the vehicle (no drug included) both had an average survival of 11 days, whilst parasitaemia was seen present in all infected mice, before the respective drug doses were given, starting on day 7 post-infection.

Biological data for exemplary compounds of the invention is provided in FIG. 2.

Example 5

Protocol for Cattle Efficacy Study

Friesian-Holstein cattle were infected with *T. congolense* and treated with a single 10 mg/kg injection of 1 or 2 injections of 5 mg/kg 1. Parasitemia was assessed after 7 days and cattle were required to remain parasite-free for 100 days to be considered cured.

*T. congolense* (KNOT 2/151 or KONT 2/23) was obtained from Prof Vincent Delespaux, Institute of Tropical Medicine, Antwerp, Belgium. Inclusion criteria for cattle into this study required that they were >4 mo of age, weaned for at least 2 mo, and had originated from a Tsetse- and *Trypanosoma*-free area. The body weight range was approximately 70-250 kg. Castrated male calves were preferred but females could be used. Animals were acclimatized for at least 28 days in an inset proof facility prior to infection with pathogen. *T. congolense*-infected fresh heparinized bovine blood from a cow with an active infection was used to infect study calves. *T. congolense* was administered intravenously, approximately 100,000 parasites/calf in a single dose.

Formulations of the compound were prepared 48 h prior to dosing administration in the following formulation: 60:20:20 Pyrrolidinone:PEG300:water. Control calves were injected with sterile saline. Calves were injected with 1 or saline at first peak parasitemia (parasitemia score >4, and reduction in pre-infection packed cell volume of 0.25 to 0.40), either with a single dose of 10 mg/kg or 2 doses of 5 mg/kg, with a 12 h interval between doses. 1 was administered intramuscularly into the middle of the neck muscle mass, using up to 4 injections of 10 mL volume. N=6 animals per treatment group. An uninfected, untreated control group of 6 animals was included.

Blood was sampled for parasitemia and packed cell volume (PCV) daily until Day +22 post treatment. Daily clinical observations were performed on Day +5 until +22. After 2 negative venous specimens, the absence of parasites was confirmed by examining a buffy coat from a marginal ear vein on the following working day. Body weights were measured on Days T29 and 30 (twice), T59 and 60, and T99 and 100. The study ended on Day 100.

Example 6

Method for Estimation of Kinetic Solubility of Compounds of the Invention

The kinetic solubilities of compounds were estimated using a nephelometric (light scattering) method. Briefly, compounds were serially diluted in DMSO, followed by dilution in PBS pH 7.4. After incubation, the amount of light scattered by a compound at each concentration was measured. Clear solutions of soluble compounds do not scatter a light beam passed through the sample well and produce no signal. At concentrations above the solubility limit, the compound precipitates and the precipitant in the well scatters the light, generating a signal. Higher levels of precipitant in a well scatter more light and produce a stronger signal.

A stock solution of compound (25 mM in DMSO) was prepared, and was serially diluted in DMSO in two-fold increments in a row of a 96 well plate to a lowest concentration of 24 µM. A duplicate plate was prepared by transfer of half of the volume of each well to a new plate. Each well containing DMSO solution of the test compound was then diluted further (1:100) with phosphate buffered saline (pH 7.4) to provide aqueous solutions of compound at the following final concentrations: 250, 125, 62.5, 31.3, 15.6, 7.8, 3.9, 2.0, 1.0, 0.5 and 0.2 JIM. All liquid handling stages were performed on a Beckman Coulter Biomek NX Laboratory Automation Workstation. Each compound was diluted and tested in duplicate, providing four separate wells at each test concentration.

The test solutions of compound were incubated at room temperature for 90 minutes and then analyzed using a Thermoskan Ascent nephelometric plate reader. The nephelometer protocol included two steps: first, the plate was shaken for 60 seconds at 1200 rpm, then each well of the plate was read in succession with an 800 ms settling delay between measurements. The total measurement time for a single plate was less than 4 minutes.

The four values (in nephelometric units) obtained for each compound at each concentration were averaged and plotted on a log scale versus concentration. The concentration at which the nephelometric signal is >110% of the value obtained for a DMSO/PBS blank is reported as the limit of solubility.

Aqueous solubility of 1 in phosphate buffered saline at pH 7.4 is 50 µM. 4-fluoro-N-(1-hydroxy-3,3-dimethyl-1,3-dihydrobenzo[c][1,2]oxaborol-6-yl)-2-(trifluoromethyl)benzamide, disclosed in WO2011/019618, has a much lower solubility, 25 µM, under these conditions. The increased solubility of compounds of the invention, such as 1, can lower the volume of compound that needs to be administered to the animal. For a compound that is part of an injectable formulation, this can result in a lower number of injections to be administered to the animal.

Example 7

L929 Cells and Cultivation

For evaluation of compound effects on mammalian cells, L929 mouse fibroblast cells were used. Cells were maintained as adherent cultures in T-25 vented cap flasks in a humidified incubator at 37° C. in the presence of 5% $CO_2$. Culture media was D-MEM supplemented with 10% fetal bovine serum and 1% penicillin/streptomycin. L929 cells were maintained below confluent levels by sub-culturing at 1:10 dilution twice weekly using 0.05% trypsin for detachment.

Cytotoxicity Evaluation

Sub-confluent L929 cells were trypsinized, resuspended in fresh media and 10 uL was counted using hemocytometer to determine cell concentration. Cells were diluted to $1 \times 10^4$/mL in DMEM, dispensed (100 uL) into 96-well plates using a Multidrop 384 dispenser and allowed to attach overnight. Spent media was replaced with 99.5 uL fresh D-MEM and compounds to be tested were serially diluted in DMSO and 0.5 uL added using a Biomek NX liquid handler. Plates were incubated with compounds for 72 hrs at 37° C. with 5% $CO_2$. Resazurin (20 uL of 12.5 mg/ml stock) from Sigma-Aldrich was added to each well and plates were incubated for an additional 3-4 hrs. Assay plates were read using an EnVision plate reader at an excitation wavelength of 544 nm and emission of 590 nm. Single data points were used to generate sigmoidal dose response curves and determine $IC_{50}$ values using XLfit curve fitting software from IDBS (Guildford, UK).

Biological data for exemplary compounds of the invention is provided in FIG. 1A-B.

Example 8

*Leishmania donovani* Strain and Cultivation

All experiments were conducted with the axenic amastigote-form of the following parasite: *Leishmania donovani* strain 1S-CL2D from Sudan, World Health Organization (WHO) designation: (MHOM/SD/62/1S-CL2D). Parasites were cultured in T-25 vented cap flasks and kept in humidified incubators at 37° C. and 5% CO2. The axenic parasite culture media was RPMI-1640/MES/pH 5.5 formulated and prepared as described by Debrabant et. al. (International Journal for Parasitology 2004, Volume 34, page 205-217). To ensure log growth phase, axenic amastigotes were subcultured at appropriate dilutions every 2-3 days.

In Vitro Drug Sensitivity Assays

Cultures of axenic amastigotes growing in the log phase were passed through a 22 gauge blunt needle to break up the clumps, diluted 1:10 in RPMI-1640/MES medium and counted using hemocytometer to determine parasite concentration. Amastigotes were diluted to $2\times10^5$/mL in RPMI-1640/MES medium to generate a 2-fold working concentration for assay. Compounds to be tested were serially diluted in DMSO and 0.5 µL added to 50 µL HMI-9 in triplicate 96-well plates using a Biomek NX liquid handler. Parasites from the diluted stock were added to each well (50 µL) using a Multidrop 384 dispenser to give a final concentration of $1.0\times10^5$/ml parasites in 0.5% for DMSO. Amastigotes were incubated with compounds for 72 hrs at 37° C. with 5% $CO_2$. Resazurin (10 µL of 12.5 mg/ml stock) from Sigma-Aldrich was added to each well and plates were incubated for an additional 2-3 hrs. Assay plates were read using an EnVision plate reader at an excitation wavelength of 544 nm and emission of 590 nm. Triplicate data points were averaged to generate sigmoidal dose response curve and determine $IC_{50}$ values using XLfit curve fitting software from IDBS (Guildford, UK).

Biological data for exemplary compounds of the invention is provided in FIG. 1A-B.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of killing and/or preventing the growth of a protozoa, comprising contacting the protozoa with an effective amount of 2-chloro-N-(1-hydroxy-3,3-dimethyl-1,3-dihydrobenzo[c][1,2]oxaborol-6-yl)-4-(1H-pyrazol-1-yl)benzamide, or a pharmaceutically acceptable salt thereof, thereby killing and/or preventing the growth of the protozoa.

2. A method of killing and/or preventing the growth of a protozoa in a human, comprising administering to the human, in need of such treatment, a therapeutically effective amount of 2-chloro-N-(1-hydroxy-3,3-dimethyl-1,3-dihydrobenzo[c][1,2]oxaborol-6-yl)-4-(1H-pyrazol-1-yl)benzamide, or a pharmaceutically acceptable salt thereof, thereby killing and/or preventing the growth of the protozoa.

3. A method of killing and/or preventing the growth of a parasite in a human, comprising administering to the human, in need of such treatment, a therapeutically effective amount of 2-chloro-N-(1-hydroxy-3,3-dimethyl-1,3-dihydrobenzo[c][1,2]oxaborol-6-yl)-4-(1H-pyrazol-1-yl)benzamide, or a pharmaceutically acceptable salt thereof, thereby killing and/or preventing the growth of the parasite.

* * * * *